(12) United States Patent
Smith et al.

(10) Patent No.: US 9,701,940 B2
(45) Date of Patent: *Jul. 11, 2017

(54) CELL-SUPPORT MATRIX HAVING NARROWLY DEFINED UNIFORMLY VERTICALLY AND NON-RANDOMLY ORGANIZED POROSITY AND PORE DENSITY AND A METHOD FOR PREPARATION THEREOF

(71) Applicant: Histogenics Corporation, Waltham, MA (US)

(72) Inventors: R. Lane Smith, Palo Alto, CA (US); Laurence J. B. Tarrant, Easthampton, MA (US); Akihiko Kusanagi, Brookline, MA (US); Hans P. I. Claesson, Wayland, MA (US)

(73) Assignee: Histogenics Corporation, Waltham, MA (US)

( * ) Notice: Subject to any disclaimer, the term of this patent is extended or adjusted under 35 U.S.C. 154(b) by 229 days.

This patent is subject to a terminal disclaimer.

(21) Appl. No.: 14/577,610

(22) Filed: Dec. 19, 2014

(65) Prior Publication Data

US 2015/0104872 A1 Apr. 16, 2015

Related U.S. Application Data

(63) Continuation of application No. 11/523,833, filed on Sep. 19, 2006, now Pat. No. 8,921,109.
(Continued)

(51) Int. Cl.
*C12N 5/00* (2006.01)
*A61L 27/24* (2006.01)
(Continued)

(52) U.S. Cl.
CPC ............ *C12N 5/0068* (2013.01); *A61L 27/24* (2013.01); *A61L 27/3817* (2013.01);
(Continued)

(58) Field of Classification Search
None
See application file for complete search history.

(56) References Cited

U.S. PATENT DOCUMENTS 3,400,199 A 9/1968 Balassa
3,476,855 A 11/1969 Balassa
(Continued)

FOREIGN PATENT DOCUMENTS

EP 0068149 A2 1/1983
EP 0075444 A2 3/1983
(Continued)

OTHER PUBLICATIONS

Li JL, Cai JL, Guo JL, Fuh JYH, Sun J, Hong GS, Lam RN, Wong YS, Wang W, Tay BY, Thian ES. 2014. Fabrication of three-dimensional porous scaffolds with controlled filament orientation and large pore size via an improved E-jetting technique. J Biomed Mater Res Part B 2014:102B(4), pp. 651-658. doi/10.1002/jbm.b.33043/epdf.*
(Continued)

*Primary Examiner* — Chris R Tate
*Assistant Examiner* — Aaron J Kosar
(74) *Attorney, Agent, or Firm* — Brown Rudnick LLP; Thomas C. Meyers

(57) ABSTRACT

A cell-support matrix having narrowly defined uniformly vertically and non-randomly organized porosity and pore density and a method for preparation thereof. The matrix suitable for preparation of cellular or acellular implants for growth and de novo formation of an articular hyaline-like cartilage. A gel-matrix composite system comprising colla-
(Continued)

gen-based matrix having a narrowly defined porosity capable of inducing hyaline-like cartilage production from chondrocytes in vivo and in vitro.

19 Claims, 16 Drawing Sheets

Related U.S. Application Data

(60) Provisional application No. 60/718,714, filed on Sep. 19, 2005.

(51) Int. Cl.
*A61L 27/38* (2006.01)
*A61L 27/56* (2006.01)
*C12N 5/077* (2010.01)
*A61F 2/08* (2006.01)
*A61F 2/30* (2006.01)
*A61F 2/38* (2006.01)

(52) U.S. Cl.
CPC .......... *A61L 27/3843* (2013.01); *A61L 27/56* (2013.01); *C12N 5/0655* (2013.01); *A61F 2/08* (2013.01); *A61F 2/30756* (2013.01); *A61F 2/3872* (2013.01); *A61F 2002/30062* (2013.01); *A61F 2210/0004* (2013.01); *A61F 2310/00365* (2013.01); *A61L 2400/18* (2013.01); *A61L 2430/06* (2013.01); *A61L 2430/10* (2013.01); *C12N 2533/54* (2013.01); *C12N 2535/00* (2013.01)

(56) References Cited

U.S. PATENT DOCUMENTS

| | | |
|---|---|---|
| 3,478,146 A | 11/1969 | Balassa |
| 3,551,560 A | 12/1970 | Thiele |
| 3,772,432 A | 11/1973 | Balassa |
| 3,867,728 A | 2/1975 | Stubstad et al. |
| 3,966,908 A | 6/1976 | Balassa |
| 4,060,081 A | 11/1977 | Yannas et al. |
| 4,172,128 A | 10/1979 | Thiele et al. |
| 4,182,655 A | 1/1980 | Hartmeier |
| 4,201,845 A | 5/1980 | Feder et al. |
| 4,280,954 A | 7/1981 | Yannas et al. |
| 4,296,100 A | 10/1981 | Franco |
| 4,350,629 A | 9/1982 | Yannas et al. |
| 4,378,347 A | 3/1983 | Franco |
| 4,394,370 A | 7/1983 | Jefferies |
| 4,400,833 A | 8/1983 | Kurland |
| 4,442,655 A | 4/1984 | Stroetmann |
| 4,448,718 A | 5/1984 | Yannas et al. |
| 4,458,678 A | 7/1984 | Yannas et al. |
| 4,479,271 A | 10/1984 | Bolesky et al. |
| 4,501,269 A | 2/1985 | Bagby |
| 4,505,266 A | 3/1985 | Yannas et al. |
| 4,522,753 A | 6/1985 | Yannas et al. |
| 4,522,811 A | 6/1985 | Eppstein et al. |
| 4,582,865 A | 4/1986 | Balazs et al. |
| 4,600,574 A | 7/1986 | Lindner et al. |
| 4,609,551 A | 9/1986 | Caplan et al. |
| 4,627,853 A | 12/1986 | Campbell et al. |
| 4,642,120 A | 2/1987 | Nevo et al. |
| 4,656,137 A | 4/1987 | Balassa |
| 4,681,763 A | 7/1987 | Nathanson et al. |
| 4,683,195 A | 7/1987 | Mullis et al. |
| 4,683,202 A | 7/1987 | Mullis |
| 4,713,448 A | 12/1987 | Balazs et al. |
| 4,736,866 A | 4/1988 | Leder et al. |
| 4,757,017 A | 7/1988 | Cheung |
| 4,776,173 A | 10/1988 | Kamarei et al. |
| 4,776,853 A | 10/1988 | Klement et al. |
| 4,795,467 A | 1/1989 | Piez et al. |
| 4,801,299 A | 1/1989 | Brendel et al. |
| 4,837,379 A | 6/1989 | Weinberg |
| 4,846,835 A | 7/1989 | Grande |
| 4,851,354 A | 7/1989 | Winston et al. |
| 4,870,009 A | 9/1989 | Evans et al. |
| 4,873,191 A | 10/1989 | Wagner et al. |
| 4,873,192 A | 10/1989 | Kunkel |
| 4,880,429 A | 11/1989 | Stone |
| 4,880,610 A | 11/1989 | Constantz |
| 4,902,508 A | 2/1990 | Badylak et al. |
| 4,904,259 A | 2/1990 | Itay |
| 4,912,032 A | 3/1990 | Hoffman et al. |
| 4,932,973 A | 6/1990 | Gendler |
| 4,950,296 A | 8/1990 | McIntyre |
| 4,950,483 A | 8/1990 | Ksander et al. |
| 4,955,911 A | 9/1990 | Frey et al. |
| 4,963,146 A | 10/1990 | Li |
| 4,963,489 A | 10/1990 | Naughton et al. |
| 4,965,188 A | 10/1990 | Mullis et al. |
| 4,971,954 A | 11/1990 | Brodsky et al. |
| 4,976,738 A | 12/1990 | Frey et al. |
| 4,978,355 A | 12/1990 | Frey et al. |
| 4,981,783 A | 1/1991 | Augenlicht |
| 4,994,559 A | 2/1991 | Moscatelli et al. |
| 5,002,071 A | 3/1991 | Harrell |
| 5,002,583 A | 3/1991 | Pitaru et al. |
| 5,007,934 A | 4/1991 | Stone |
| 5,010,892 A | 4/1991 | Colvin et al. |
| 5,032,508 A | 7/1991 | Naughton et al. |
| 5,041,138 A | 8/1991 | Vacanti et al. |
| 5,053,049 A | 10/1991 | Campbell |
| 5,053,050 A | 10/1991 | Itay |
| 5,067,963 A | 11/1991 | Khouri et al. |
| 5,067,964 A | 11/1991 | Richmond et al. |
| 5,071,436 A | 12/1991 | Huc et al. |
| 5,073,373 A | 12/1991 | O'Leary et al. |
| 5,084,051 A | 1/1992 | Tormala et al. |
| 5,087,963 A | 2/1992 | Kaneda et al. |
| 5,092,867 A | 3/1992 | Harms et al. |
| 5,092,887 A | 3/1992 | Gendler |
| 5,118,512 A | 6/1992 | O'Leary et al. |
| 5,152,791 A | 10/1992 | Hakamatsuka et al. |
| 5,155,214 A | 10/1992 | Baird et al. |
| 5,191,067 A | 3/1993 | Lappi et al. |
| 5,195,892 A | 3/1993 | Gersberg |
| 5,206,023 A | 4/1993 | Hunziker |
| 5,206,028 A | 4/1993 | Li |
| 5,226,914 A | 7/1993 | Caplan et al. |
| 5,227,147 A | 7/1993 | Yoshimura et al. |
| 5,236,456 A | 8/1993 | O'Leary et al. |
| 5,256,140 A | 10/1993 | Fallick |
| 5,256,476 A | 10/1993 | Tanaka et al. |
| 5,260,420 A | 11/1993 | Burnouf-Radosevich et al. |
| 5,270,197 A | 12/1993 | Yayon et al. |
| 5,270,300 A | 12/1993 | Hunziker |
| 5,275,826 A | 1/1994 | Badylak et al. |
| 5,281,265 A | 1/1994 | Liu |
| 5,281,422 A | 1/1994 | Badylak et al. |
| 5,284,155 A | 2/1994 | Treadwell et al. |
| 5,290,558 A | 3/1994 | O'Leary et al. |
| 5,298,254 A | 3/1994 | Prewett et al. |
| 5,302,702 A | 4/1994 | Seddon et al. |
| 5,306,304 A | 4/1994 | Gendler |
| 5,306,311 A | 4/1994 | Stone et al. |
| 5,306,500 A | 4/1994 | Rhee et al. |
| 5,310,883 A | 5/1994 | Seddon et al. |
| 5,314,476 A | 5/1994 | Prewett et al. |
| 5,326,357 A | 7/1994 | Kandel |
| 5,329,846 A | 7/1994 | Bonutti |
| 5,336,616 A | 8/1994 | Livesey et al. |
| 5,338,772 A | 8/1994 | Bauer et al. |
| 5,352,463 A | 10/1994 | Badylak et al. |
| 5,352,589 A | 10/1994 | Bergonzoni et al. |
| 5,354,557 A | 10/1994 | Oppermann et al. |
| 5,356,629 A | 10/1994 | Sander et al. |
| 5,356,883 A | 10/1994 | Kuo et al. |
| 5,368,858 A | 11/1994 | Hunziker |
| 5,372,821 A | 12/1994 | Badylak et al. |
| 5,380,328 A | 1/1995 | Morgan |

(56) References Cited

U.S. PATENT DOCUMENTS

| | | | |
|---|---|---|---|
| 5,410,016 | A | 4/1995 | Hubbell et al. |
| 5,411,885 | A | 5/1995 | Marx |
| 5,425,769 | A | 6/1995 | Snyders, Jr. |
| 5,439,684 | A | 8/1995 | Prewett et al. |
| 5,439,818 | A | 8/1995 | Fiddes et al. |
| 5,443,950 | A | 8/1995 | Naughton et al. |
| 5,445,833 | A | 8/1995 | Badylak et al. |
| 5,464,439 | A | 11/1995 | Gendler |
| 5,466,462 | A | 11/1995 | Rosenthal et al. |
| 5,471,893 | A | 12/1995 | Newbigging |
| 5,474,987 | A | 12/1995 | Cohen et al. |
| 5,475,052 | A | 12/1995 | Rhee et al. |
| 5,491,220 | A | 2/1996 | Seddon et al. |
| 5,496,722 | A | 3/1996 | Goodwin et al. |
| 5,507,813 | A | 4/1996 | Dowd et al. |
| 5,510,396 | A | 4/1996 | Prewett et al. |
| 5,512,460 | A | 4/1996 | Nauro et al. |
| 5,513,662 | A | 5/1996 | Morse et al. |
| 5,516,532 | A | 5/1996 | Atala et al. |
| 5,516,533 | A | 5/1996 | Badylak et al. |
| 5,522,753 | A | 6/1996 | McGraw |
| 5,545,222 | A | 8/1996 | Bonutti |
| 5,549,904 | A | 8/1996 | Juergensen et al. |
| 5,554,389 | A | 9/1996 | Badylak et al. |
| 5,556,430 | A | 9/1996 | Gendler |
| 5,565,519 | A | 10/1996 | Rhee et al. |
| 5,569,272 | A | 10/1996 | Reed et al. |
| 5,569,584 | A | 10/1996 | Augenlicht |
| 5,571,895 | A | 11/1996 | Kurokawa et al. |
| 5,576,288 | A | 11/1996 | Lappi et al. |
| 5,604,293 | A | 2/1997 | Fiddes et al. |
| 5,606,793 | A | 3/1997 | Gross et al. |
| 5,607,474 | A | 3/1997 | Athanasiou et al. |
| 5,614,496 | A | 3/1997 | Dunstan et al. |
| 5,614,587 | A | 3/1997 | Rhee et al. |
| 5,616,568 | A | 4/1997 | Pouyani et al. |
| 5,618,551 | A | 4/1997 | Tardy et al. |
| 5,618,925 | A | 4/1997 | Dupont et al. |
| 5,622,928 | A | 4/1997 | Naruo et al. |
| 5,624,463 | A | 4/1997 | Stone et al. |
| 5,629,191 | A | 5/1997 | Cahn |
| 5,630,842 | A | 5/1997 | Brodniewicz |
| 5,630,982 | A | 5/1997 | Boring |
| 5,631,011 | A | 5/1997 | Wadstrom |
| 5,632,745 | A | 5/1997 | Schwartz |
| 5,650,176 | A | 7/1997 | Lee et al. |
| 5,653,730 | A | 8/1997 | Hammerslag |
| 5,656,492 | A | 8/1997 | Glowacki et al. |
| 5,656,598 | A | 8/1997 | Dunstan et al. |
| 5,662,710 | A | 9/1997 | Bonutti |
| 5,676,976 | A | 10/1997 | Lee et al. |
| 5,679,637 | A | 10/1997 | Lappi et al. |
| 5,681,353 | A | 10/1997 | Li et al. |
| 5,683,461 | A | 11/1997 | Lee et al. |
| 5,686,431 | A | 11/1997 | Cohen et al. |
| 5,695,998 | A | 12/1997 | Badylak et al. |
| 5,700,476 | A | 12/1997 | Rosenthal et al. |
| 5,700,774 | A | 12/1997 | Hattersley et al. |
| 5,707,962 | A | 1/1998 | Chen et al. |
| 5,713,374 | A | 2/1998 | Pachence et al. |
| 5,716,413 | A | 2/1998 | Walter et al. |
| 5,723,331 | A | 3/1998 | Tubo et al. |
| 5,728,159 | A | 3/1998 | Stroever et al. |
| 5,733,337 | A | 3/1998 | Carr, Jr. et al. |
| 5,733,564 | A | 3/1998 | Lehtinen |
| 5,736,132 | A | 4/1998 | Juergensen et al. |
| 5,736,372 | A | 4/1998 | Vacanti et al. |
| 5,736,396 | A | 4/1998 | Bruder et al. |
| 5,749,874 | A | 5/1998 | Schwartz |
| 5,755,791 | A | 5/1998 | Whitson et al. |
| 5,759,190 | A | 6/1998 | Vibe-Hansen et al. |
| 5,763,416 | A | 6/1998 | Bonadio et al. |
| 5,769,899 | A | 6/1998 | Schwartz et al. |
| 5,770,229 | A | 6/1998 | Tanihara et al. |
| 5,770,417 | A | 6/1998 | Vacanti et al. |
| 5,782,835 | A | 7/1998 | Hart et al. |
| 5,782,915 | A | 7/1998 | Stone |
| 5,786,217 | A | 7/1998 | Tubo et al. |
| 5,788,625 | A | 8/1998 | Plouhar et al. |
| 5,800,537 | A | 9/1998 | Bell |
| 5,814,084 | A | 9/1998 | Grivas et al. |
| 5,824,055 | A | 10/1998 | Spiridigliozzi et al. |
| 5,830,493 | A | 11/1998 | Yokota et al. |
| 5,837,458 | A | 11/1998 | Minshull et al. |
| 5,837,534 | A | 11/1998 | Olson et al. |
| 5,842,477 | A | 12/1998 | Naughton et al. |
| 5,846,931 | A | 12/1998 | Hattersley et al. |
| 5,853,746 | A | 12/1998 | Hunziker |
| 5,855,620 | A | 1/1999 | Bishopric et al. |
| 5,859,208 | A | 1/1999 | Fiddes et al. |
| 5,863,296 | A | 1/1999 | Orton |
| 5,863,297 | A | 1/1999 | Walter et al. |
| 5,866,415 | A | 2/1999 | Villeneuve |
| 5,874,417 | A | 2/1999 | Prestwich et al. |
| 5,876,444 | A | 3/1999 | Lai |
| 5,876,452 | A | 3/1999 | Athanasiou et al. |
| 5,881,733 | A | 3/1999 | Stone |
| 5,888,219 | A | 3/1999 | Bonutti |
| 5,893,888 | A | 4/1999 | Bell |
| 5,899,936 | A | 5/1999 | Goldstein |
| 5,899,939 | A | 5/1999 | Boyce et al. |
| 5,902,741 | A | 5/1999 | Purchio et al. |
| 5,904,716 | A | 5/1999 | Gendler |
| 5,906,827 | A | 5/1999 | Khouri et al. |
| 5,908,837 | A | 6/1999 | Cohen et al. |
| 5,908,924 | A | 6/1999 | Burdette et al. |
| 5,910,315 | A | 6/1999 | Stevenson et al. |
| 5,916,265 | A | 6/1999 | Hu |
| 5,916,557 | A | 6/1999 | Berlowitz-Tarrant et al. |
| 5,922,028 | A | 7/1999 | Plouhar et al. |
| 5,928,945 | A | 7/1999 | Seliktar et al. |
| 5,942,496 | A | 8/1999 | Bonadio et al. |
| 5,948,429 | A | 9/1999 | Bell et al. |
| 5,949,252 | A | 9/1999 | Taguchi |
| 5,955,438 | A | 9/1999 | Pitaru et al. |
| 5,964,805 | A | 10/1999 | Stone |
| 5,965,125 | A | 10/1999 | Mineau-Hanschke |
| 5,972,368 | A | 10/1999 | McKay |
| 5,972,385 | A | 10/1999 | Liu et al. |
| 5,974,663 | A | 11/1999 | Ikeda et al. |
| 5,976,524 | A | 11/1999 | Hammerman |
| 5,989,269 | A | 11/1999 | Vibe-Hansen et al. |
| 5,989,289 | A | 11/1999 | Coates et al. |
| 5,989,866 | A | 11/1999 | Deisher et al. |
| 5,998,170 | A | 12/1999 | Arakawa et al. |
| 6,001,352 | A | 12/1999 | Boyan et al. |
| 6,005,161 | A | 12/1999 | Brekke et al. |
| 6,013,853 | A | 1/2000 | Athanasiou et al. |
| 6,015,711 | A | 1/2000 | Olson et al. |
| 6,017,348 | A | 1/2000 | Hart et al. |
| 6,022,744 | A | 2/2000 | Tetteroo et al. |
| 6,025,334 | A | 2/2000 | Dupont et al. |
| 6,025,538 | A | 2/2000 | Yaccarino, III |
| 6,027,742 | A | 2/2000 | Lee et al. |
| 6,027,743 | A | 2/2000 | Khouri et al. |
| 6,027,744 | A | 2/2000 | Vacanti et al. |
| 6,030,635 | A | 2/2000 | Gertzman et al. |
| 6,037,171 | A | 3/2000 | Larsson |
| 6,039,762 | A | 3/2000 | McKay |
| 6,042,610 | A | 3/2000 | Li et al. |
| 6,056,777 | A | 5/2000 | McDowell |
| 6,060,640 | A | 5/2000 | Pauley et al. |
| 6,074,663 | A | 6/2000 | Delmotte et al. |
| 6,080,194 | A | 6/2000 | Pachence et al. |
| 6,090,996 | A | 7/2000 | Li |
| 6,090,998 | A | 7/2000 | Grooms et al. |
| 6,096,081 | A | 8/2000 | Grivas et al. |
| 6,096,347 | A | 8/2000 | Geddes et al. |
| 6,103,255 | A | 8/2000 | Levene et al. |
| 6,110,209 | A | 8/2000 | Stone |
| 6,110,482 | A | 8/2000 | Khouri et al. |
| 6,110,746 | A | 8/2000 | Cohen et al. |
| 6,118,043 | A | 9/2000 | Nies et al. |
| 6,123,731 | A | 9/2000 | Boyce et al. |

(56) References Cited

U.S. PATENT DOCUMENTS

| | | |
|---|---|---|
| 6,132,472 A | 10/2000 | Bonutti |
| 6,140,087 A | 10/2000 | Graham et al. |
| 6,143,293 A | 11/2000 | Weiss et al. |
| 6,146,385 A | 11/2000 | Torrie et al. |
| 6,150,163 A | 11/2000 | McPherson et al. |
| 6,156,068 A | 12/2000 | Walter et al. |
| 6,156,572 A | 12/2000 | Bellamkonda et al. |
| 6,159,179 A | 12/2000 | Simonson |
| 6,165,487 A | 12/2000 | Ashkar et al. |
| 6,171,610 B1 | 1/2001 | Vacanti et al. |
| 6,174,333 B1 | 1/2001 | Kadiyala et al. |
| 6,176,880 B1 | 1/2001 | Plouhar et al. |
| 6,180,605 B1 | 1/2001 | Chen et al. |
| 6,183,737 B1 | 2/2001 | Zaleske et al. |
| 6,189,537 B1 | 2/2001 | Wolfinbarger, Jr. |
| 6,197,061 B1 | 3/2001 | Masuda et al. |
| 6,197,586 B1 | 3/2001 | Bhatnagar et al. |
| 6,200,347 B1 | 3/2001 | Anderson et al. |
| 6,201,165 B1 | 3/2001 | Grant et al. |
| 6,214,368 B1 | 4/2001 | Lee et al. |
| 6,221,854 B1 | 4/2001 | Radomsky |
| 6,231,607 B1 | 5/2001 | Ben-Bassat et al. |
| 6,231,879 B1 | 5/2001 | Li et al. |
| 6,235,316 B1 | 5/2001 | Adkisson |
| 6,242,247 B1 | 6/2001 | Rieser et al. |
| 6,251,143 B1 | 6/2001 | Schwartz et al. |
| 6,258,778 B1 | 7/2001 | Rodgers et al. |
| 6,261,586 B1 | 7/2001 | McKay |
| 6,267,786 B1 | 7/2001 | Stone |
| 6,270,528 B1 | 8/2001 | McKay |
| 6,274,090 B1 | 8/2001 | Coelho et al. |
| 6,274,663 B1 | 8/2001 | Hosokawa et al. |
| 6,274,712 B1 | 8/2001 | Springer et al. |
| 6,280,473 B1 | 8/2001 | Lemperle et al. |
| 6,281,195 B1 | 8/2001 | Rueger et al. |
| 6,283,980 B1 | 9/2001 | Vibe-Hansen et al. |
| 6,288,043 B1 | 9/2001 | Spiro et al. |
| 6,293,970 B1 | 9/2001 | Wolfinbarger, Jr. et al. |
| 6,294,187 B1 | 9/2001 | Boyce et al. |
| 6,294,202 B1 | 9/2001 | Burns et al. |
| 6,294,359 B1 | 9/2001 | Fiddes et al. |
| 6,303,585 B1 | 10/2001 | Spiro et al. |
| 6,305,379 B1 | 10/2001 | Wolfinbarger, Jr. |
| 6,306,169 B1 | 10/2001 | Lee et al. |
| 6,306,174 B1 | 10/2001 | Gie et al. |
| 6,306,424 B1 | 10/2001 | Vyakarnam et al. |
| 6,310,267 B1 | 10/2001 | Rapp |
| 6,312,725 B1 | 11/2001 | Wallace et al. |
| 6,315,992 B1 | 11/2001 | Noh et al. |
| 6,319,712 B1 | 11/2001 | Meenen et al. |
| 6,322,563 B1 | 11/2001 | Cummings et al. |
| 6,331,312 B1 | 12/2001 | Lee et al. |
| 6,333,029 B1 | 12/2001 | Vyakarnam et al. |
| 6,334,968 B1 | 1/2002 | Shapiro et al. |
| 6,337,198 B1 | 1/2002 | Levene et al. |
| 6,346,515 B1 | 2/2002 | Pitaru et al. |
| 6,352,558 B1 | 3/2002 | Spector |
| 6,352,971 B1 | 3/2002 | Deisher et al. |
| 6,361,565 B1 | 3/2002 | Bonutti |
| 6,371,958 B1 | 4/2002 | Overaker |
| 6,375,935 B1 | 4/2002 | Constantz |
| 6,376,244 B1 | 4/2002 | Atala |
| 6,378,527 B1 | 4/2002 | Hungerford et al. |
| 6,379,367 B1 | 4/2002 | Vibe-Hansen et al. |
| 6,379,385 B1 | 4/2002 | Kalas et al. |
| 6,383,221 B1 | 5/2002 | Scarborough et al. |
| 6,387,693 B2 | 5/2002 | Rieser et al. |
| 6,398,811 B1 | 6/2002 | McKay |
| 6,398,816 B1 | 6/2002 | Breitbart et al. |
| 6,398,972 B1 | 6/2002 | Blasetti et al. |
| 6,406,476 B1 | 6/2002 | Kirwan, Jr. et al. |
| 6,417,247 B1 | 7/2002 | Armstrong et al. |
| 6,425,918 B1 | 7/2002 | Shapiro et al. |
| 6,432,436 B1 | 8/2002 | Gertzman et al. |
| 6,432,713 B2 | 8/2002 | Takagi et al. |
| 6,437,018 B1 | 8/2002 | Gertzman et al. |
| 6,440,141 B1 | 8/2002 | Philippon |
| 6,440,427 B1 | 8/2002 | Wadstrom |
| 6,440,444 B2 | 8/2002 | Boyce et al. |
| 6,440,934 B1 | 8/2002 | Whitehouse |
| 6,443,988 B2 | 9/2002 | Felt et al. |
| 6,444,222 B1 | 9/2002 | Asculai et al. |
| 6,447,701 B1 | 9/2002 | Heschel et al. |
| 6,451,060 B2 | 9/2002 | Masuda et al. |
| 6,454,811 B1 | 9/2002 | Sherwood et al. |
| 6,458,144 B1 | 10/2002 | Morris et al. |
| 6,458,158 B1 | 10/2002 | Anderson et al. |
| 6,458,375 B1 | 10/2002 | Gertzman et al. |
| 6,468,314 B2 | 10/2002 | Schwartz et al. |
| 6,475,175 B1 | 11/2002 | Rivera et al. |
| 6,486,377 B2 | 11/2002 | Rapp |
| 6,488,033 B1 | 12/2002 | Cerundolo |
| 6,489,165 B2 | 12/2002 | Bhatnagar et al. |
| 6,489,455 B2 | 12/2002 | Chenchik et al. |
| 6,497,726 B1 | 12/2002 | Carter et al. |
| 6,503,277 B2 | 1/2003 | Bonutti |
| 6,504,079 B2 | 1/2003 | Tucker et al. |
| 6,511,511 B1 | 1/2003 | Slivka et al. |
| 6,511,958 B1 | 1/2003 | Atkinson et al. |
| 6,514,514 B1 | 2/2003 | Atkinson et al. |
| 6,517,872 B1 | 2/2003 | Yayon et al. |
| 6,520,964 B2 | 2/2003 | Tallarida et al. |
| 6,528,052 B1 | 3/2003 | Smith et al. |
| 6,530,956 B1 | 3/2003 | Mansmann |
| 6,533,821 B1 | 3/2003 | Lally |
| 6,534,084 B1 | 3/2003 | Vyakarnam et al. |
| 6,541,024 B1 | 4/2003 | Kadiyala et al. |
| 6,548,729 B1 | 4/2003 | Seelich et al. |
| 6,551,784 B2 | 4/2003 | Fodor et al. |
| 6,569,172 B2 | 5/2003 | Asculai et al. |
| 6,576,015 B2 | 6/2003 | Geistlich et al. |
| 6,576,265 B1 | 6/2003 | Spievack |
| 6,576,285 B1 | 6/2003 | Bader et al. |
| 6,579,538 B1 | 6/2003 | Spievack |
| 6,582,960 B1 | 6/2003 | Martin et al. |
| 6,591,581 B2 | 7/2003 | Schmieding |
| 6,592,598 B2 | 7/2003 | Vibe-Hansen et al. |
| 6,592,599 B2 | 7/2003 | Vibe-Hansen et al. |
| 6,599,300 B2 | 7/2003 | Vibe-Hansen et al. |
| 6,599,301 B2 | 7/2003 | Vibe-Hansen et al. |
| 6,599,515 B1 | 7/2003 | Delmotte |
| 6,607,879 B1 | 8/2003 | Cocks et al. |
| 6,623,963 B1 | 9/2003 | Muller et al. |
| 6,624,245 B2 | 9/2003 | Wallace et al. |
| 6,626,950 B2 | 9/2003 | Brown et al. |
| 6,630,000 B1 | 10/2003 | Bonutti |
| 6,630,457 B1 | 10/2003 | Aeschlimann et al. |
| 6,632,247 B2 | 10/2003 | Boyer, II et al. |
| 6,632,651 B1 | 10/2003 | Nevo et al. |
| 6,645,727 B2 | 11/2003 | Thomas et al. |
| 6,645,764 B1 | 11/2003 | Adkisson |
| 6,652,592 B1 | 11/2003 | Grooms et al. |
| 6,652,593 B2 | 11/2003 | Boyer, II et al. |
| 6,652,872 B2 | 11/2003 | Nevo et al. |
| 6,662,805 B2 | 12/2003 | Frondoza et al. |
| 6,666,892 B2 | 12/2003 | Hiles et al. |
| 6,673,286 B2 | 1/2004 | Shih et al. |
| 6,686,184 B1 | 2/2004 | Anderson et al. |
| 6,689,747 B2 | 2/2004 | Filvaroff et al. |
| 6,696,073 B2 | 2/2004 | Boyce et al. |
| 6,712,851 B1 | 3/2004 | Lemperle et al. |
| 6,727,224 B1 | 4/2004 | Zhang et al. |
| 6,730,314 B2 | 5/2004 | Jeschke et al. |
| 6,734,018 B2 | 5/2004 | Wolfinbarger, Jr. et al. |
| 6,737,072 B1 | 5/2004 | Angele et al. |
| 6,743,232 B2 | 6/2004 | Overaker et al. |
| 6,752,834 B2 | 6/2004 | Geistlich et al. |
| 6,753,311 B2 | 6/2004 | Fertala et al. |
| 6,761,739 B2 | 7/2004 | Shepard |
| 6,761,887 B1 | 7/2004 | Kavalkovich et al. |
| 6,764,517 B2 | 7/2004 | Yamamoto et al. |
| 6,767,369 B2 | 7/2004 | Boyer, II et al. |
| 6,773,723 B1 | 8/2004 | Spiro et al. |
| 6,776,800 B2 | 8/2004 | Boyer, II et al. |

(56) References Cited

U.S. PATENT DOCUMENTS

| | | |
|---|---|---|
| 6,783,712 B2 | 8/2004 | Slivka et al. |
| 6,790,454 B1 | 9/2004 | Abdul Malak et al. |
| 6,803,234 B2 | 10/2004 | Havenga et al. |
| 6,808,585 B2 | 10/2004 | Boyce et al. |
| 6,815,416 B2 | 11/2004 | Carney et al. |
| 6,838,440 B2 | 1/2005 | Stiles |
| 6,841,150 B2 | 1/2005 | Halvorsen et al. |
| 6,852,114 B2 | 2/2005 | Cerundolo |
| 6,852,125 B2 | 2/2005 | Simon et al. |
| 6,852,331 B2 | 2/2005 | Lai et al. |
| 6,855,167 B2 | 2/2005 | Shimp et al. |
| 6,855,169 B2 | 2/2005 | Boyer, II et al. |
| 6,855,189 B2 | 2/2005 | Edlinger |
| 6,858,042 B2 | 2/2005 | Nadler et al. |
| 6,866,668 B2 | 3/2005 | Giannetti et al. |
| 6,875,442 B2 | 4/2005 | Holy et al. |
| 6,884,428 B2 | 4/2005 | Binette et al. |
| 6,890,354 B2 | 5/2005 | Steiner et al. |
| 6,893,462 B2 | 5/2005 | Buskirk et al. |
| 6,893,466 B2 | 5/2005 | Trieu |
| 6,896,904 B2 | 5/2005 | Spiro et al. |
| 6,902,578 B1 | 6/2005 | Anderson et al. |
| 6,902,584 B2 | 6/2005 | Kwan et al. |
| 6,911,212 B2 | 6/2005 | Gertzman et al. |
| 6,932,977 B2 | 8/2005 | Heidaran et al. |
| 6,933,326 B1 | 8/2005 | Griffey et al. |
| 6,939,562 B2 | 9/2005 | Spiro et al. |
| 6,949,252 B2 | 9/2005 | Mizuno et al. |
| 6,962,814 B2 | 11/2005 | Mitchell et al. |
| 6,989,034 B2 | 1/2006 | Hammer et al. |
| 6,991,652 B2 | 1/2006 | Burg |
| 6,993,328 B1 | 1/2006 | Oommen |
| 6,995,013 B2 | 2/2006 | Connelly et al. |
| 7,009,039 B2 | 3/2006 | Yayon et al. |
| 7,018,416 B2 | 3/2006 | Hanson et al. |
| 7,025,916 B2 | 4/2006 | Bachrach |
| 7,033,587 B2 | 4/2006 | Halvorsen et al. |
| 7,041,641 B2 | 5/2006 | Rueger et al. |
| 7,044,968 B1 | 5/2006 | Yaccarino, III et al. |
| 7,045,141 B2 | 5/2006 | Merboth et al. |
| 7,048,750 B2 | 5/2006 | Vibe-Hansen et al. |
| 7,048,762 B1 | 5/2006 | Sander et al. |
| 7,048,765 B1 | 5/2006 | Grooms et al. |
| 7,067,123 B2 | 6/2006 | Gomes et al. |
| 7,070,942 B2 | 7/2006 | Heidaran et al. |
| 7,078,232 B2 | 7/2006 | Konkle et al. |
| 7,087,082 B2 | 8/2006 | Paul et al. |
| 7,108,721 B2 | 9/2006 | Huckle et al. |
| RE39,321 E | 10/2006 | MacPhee et al. |
| 7,115,146 B2 | 10/2006 | Boyer, II et al. |
| 7,125,423 B2 | 10/2006 | Hazebrouck |
| 7,125,569 B2 | 10/2006 | Nur et al. |
| 7,132,110 B2 | 11/2006 | Kay et al. |
| 7,137,989 B2 | 11/2006 | Asculai et al. |
| 7,141,072 B2 | 11/2006 | Geistlich et al. |
| 7,148,209 B2 | 12/2006 | Hoemann et al. |
| 7,156,880 B2 | 1/2007 | Evans et al. |
| 7,157,428 B2 | 1/2007 | Kusanagi et al. |
| 7,163,563 B2 | 1/2007 | Schwartz et al. |
| 7,166,133 B2 | 1/2007 | Evans et al. |
| 7,169,610 B2 | 1/2007 | Brown |
| 7,175,852 B2 | 2/2007 | Simmoteit et al. |
| 7,179,299 B2 | 2/2007 | Edwards et al. |
| 7,182,781 B1 | 2/2007 | Bianchi et al. |
| 7,192,604 B2 | 3/2007 | Brown et al. |
| 7,201,917 B2 | 4/2007 | Malaviya et al. |
| 7,208,177 B2 | 4/2007 | Geistlich et al. |
| 7,217,294 B2 | 5/2007 | Kusanagi et al. |
| 7,220,558 B2 | 5/2007 | Luyten et al. |
| 7,226,482 B2 | 6/2007 | Messerli et al. |
| 7,241,316 B2 | 7/2007 | Evans et al. |
| 7,252,987 B2 | 8/2007 | Bachalo et al. |
| 7,264,634 B2 | 9/2007 | Schmieding |
| 7,288,406 B2 | 10/2007 | Bogin et al. |
| 7,291,169 B2 | 11/2007 | Hodorek |
| 7,297,161 B2 | 11/2007 | Fell |
| 7,299,805 B2 | 11/2007 | Bonutti |
| 7,309,232 B2 | 12/2007 | Rutherford et al. |
| 7,316,822 B2 | 1/2008 | Binette et al. |
| 7,323,011 B2 | 1/2008 | Shepard et al. |
| 7,323,445 B2 | 1/2008 | Zhang et al. |
| 7,326,571 B2 | 2/2008 | Freyman |
| 7,335,508 B2 | 2/2008 | Yayon et al. |
| 7,338,492 B2 | 3/2008 | Singhatat et al. |
| 7,338,524 B2 | 3/2008 | Fell et al. |
| 7,358,284 B2 | 4/2008 | Griffey et al. |
| 7,361,195 B2 | 4/2008 | Schwartz et al. |
| 7,365,051 B2 | 4/2008 | Paulista et al. |
| 7,371,400 B2 | 5/2008 | Borenstein et al. |
| 7,452,677 B2 | 11/2008 | Lundgren-Akerlund |
| 7,468,075 B2 | 12/2008 | Lang et al. |
| 7,468,192 B2 | 12/2008 | Mizuno et al. |
| 7,476,257 B2 | 1/2009 | Sah et al. |
| 7,479,160 B2 | 1/2009 | Branch et al. |
| 7,485,310 B2 | 2/2009 | Luyten et al. |
| 7,488,348 B2 | 2/2009 | Truncale et al. |
| 7,507,286 B2 | 3/2009 | Edidin et al. |
| 7,513,910 B2 | 4/2009 | Buskirk et al. |
| 7,524,513 B2 | 4/2009 | Hai-Quan et al. |
| 7,531,000 B2 | 5/2009 | Hodorek |
| 7,531,503 B2 | 5/2009 | Atala et al. |
| 7,537,617 B2 | 5/2009 | Bindsell et al. |
| 7,537,780 B2 | 5/2009 | Mizuno et al. |
| 7,550,007 B2 | 6/2009 | Malinin |
| 7,560,432 B2 | 7/2009 | Kusanagi et al. |
| 7,563,455 B2 | 7/2009 | McKay |
| 7,563,769 B2 | 7/2009 | Bogin et al. |
| 7,595,062 B2 | 9/2009 | Pedrozo et al. |
| 7,601,173 B2 | 10/2009 | Messerli et al. |
| 7,608,113 B2 | 10/2009 | Boyer, II et al. |
| 7,618,646 B2 | 11/2009 | Goerne et al. |
| 7,621,963 B2 | 11/2009 | Simon et al. |
| 7,622,438 B1 | 11/2009 | Lazarov et al. |
| 7,622,562 B2 | 11/2009 | Thorne et al. |
| 7,625,581 B2 | 12/2009 | Laredo et al. |
| 7,628,851 B2 | 12/2009 | Armitage et al. |
| 7,632,311 B2 | 12/2009 | Seedhom et al. |
| 7,635,592 B2 | 12/2009 | West et al. |
| 7,638,486 B2 | 12/2009 | Lazarov et al. |
| 7,642,092 B2 | 1/2010 | Maor |
| 7,648,700 B2 | 1/2010 | Vignery et al. |
| 7,648,965 B2 | 1/2010 | Vignery et al. |
| 7,658,768 B2 | 2/2010 | Miller et al. |
| 7,662,184 B2 | 2/2010 | Edwards et al. |
| 7,666,230 B2 | 2/2010 | Orban et al. |
| 7,731,756 B2 | 6/2010 | Maspero et al. |
| 7,763,272 B2 | 7/2010 | Offermann et al. |
| 7,767,806 B2 | 8/2010 | Hirakura et al. |
| 7,824,701 B2 | 11/2010 | Binette et al. |
| 7,837,740 B2 | 11/2010 | Semler et al. |
| 7,846,466 B2 | 12/2010 | Shea et al. |
| 7,875,296 B2 | 1/2011 | Binette et al. |
| 7,892,799 B2 | 2/2011 | Smith et al. |
| RE42,208 E | 3/2011 | Truncale et al. |
| 7,901,457 B2 | 3/2011 | Truncale et al. |
| 7,901,461 B2 | 3/2011 | Harmon et al. |
| 7,931,687 B2 | 4/2011 | Masuda et al. |
| 8,029,992 B2 | 10/2011 | Rapko et al. |
| 8,030,361 B2 | 10/2011 | Aso et al. |
| 8,039,258 B2 | 10/2011 | Harris et al. |
| 8,043,627 B2 | 10/2011 | Scharnweber et al. |
| 8,062,655 B2 | 11/2011 | Johnson et al. |
| 8,105,380 B2 | 1/2012 | Kharazi et al. |
| RE43,208 E | 2/2012 | Yang et al. |
| 8,110,007 B2 | 2/2012 | Borden |
| 8,119,783 B2 | 2/2012 | Bogin et al. |
| 8,147,862 B2 | 4/2012 | McKay |
| 8,185,485 B2 | 5/2012 | Keith et al. |
| 8,292,968 B2 | 10/2012 | Truncale et al. |
| 8,420,858 B2 | 4/2013 | Hwang et al. |
| 8,469,980 B2 | 6/2013 | Sengun et al. |
| 8,685,107 B2 | 4/2014 | Claesson et al. |
| 8,921,109 B2 * | 12/2014 | Smith .................. A61L 27/24 424/422 |

(56) References Cited

U.S. PATENT DOCUMENTS

| | | |
|---|---|---|
| 2001/0005592 A1 | 6/2001 | Bhatnagar et al. |
| 2001/0006634 A1 | 7/2001 | Zaleske et al. |
| 2001/0010023 A1 | 7/2001 | Schwartz et al. |
| 2001/0011131 A1 | 8/2001 | Luyten et al. |
| 2001/0011170 A1 | 8/2001 | Davison et al. |
| 2001/0016646 A1 | 8/2001 | Rueger et al. |
| 2001/0018619 A1 | 8/2001 | Enzerink et al. |
| 2001/0020188 A1 | 9/2001 | Sander |
| 2001/0021529 A1 | 9/2001 | Takagi |
| 2001/0021875 A1 | 9/2001 | Enzerink et al. |
| 2001/0031254 A1 | 10/2001 | Bianchi et al. |
| 2001/0039457 A1 | 11/2001 | Boyer et al. |
| 2001/0039458 A1 | 11/2001 | Boyer et al. |
| 2001/0041941 A1 | 11/2001 | Boyer et al. |
| 2001/0043940 A1 | 11/2001 | Boyce et al. |
| 2001/0051834 A1 | 12/2001 | Frondoza et al. |
| 2001/0055615 A1 | 12/2001 | Wallace et al. |
| 2002/0009805 A1 | 1/2002 | Nevo et al. |
| 2002/0016592 A1 | 2/2002 | Branch et al. |
| 2002/0022884 A1 | 2/2002 | Mansmann |
| 2002/0035401 A1 | 3/2002 | Boyce et al. |
| 2002/0042373 A1 | 4/2002 | Carney et al. |
| 2002/0045940 A1 | 4/2002 | Giannetti et al. |
| 2002/0055783 A1 | 5/2002 | Tallarida et al. |
| 2002/0062152 A1 | 5/2002 | Dauner et al. |
| 2002/0072806 A1 | 6/2002 | Buskirk et al. |
| 2002/0082220 A1 | 6/2002 | Hoemann et al. |
| 2002/0082623 A1 | 6/2002 | Osther et al. |
| 2002/0082704 A1 | 6/2002 | Cerundolo |
| 2002/0099448 A1 | 7/2002 | Hiles et al. |
| 2002/0106393 A1 | 8/2002 | Bianchi et al. |
| 2002/0106625 A1 | 8/2002 | Hung et al. |
| 2002/0111695 A1 | 8/2002 | Kandel |
| 2002/0120274 A1 | 8/2002 | Overaker et al. |
| 2002/0138143 A1 | 9/2002 | Grooms et al. |
| 2002/0177224 A1 | 11/2002 | Madry et al. |
| 2002/0177859 A1 | 11/2002 | Monassevitch et al. |
| 2002/0192263 A1 | 12/2002 | Merboth et al. |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0039695 A1 | 2/2003 | Geistlich et al. |
| 2003/0040113 A1 | 2/2003 | Mizuno et al. |
| 2003/0044444 A1 | 3/2003 | Malaviya et al. |
| 2003/0049299 A1 | 3/2003 | Malaviya et al. |
| 2003/0050709 A1 | 3/2003 | Noth et al. |
| 2003/0055502 A1 | 3/2003 | Lang et al. |
| 2003/0078617 A1 | 4/2003 | Schwartz et al. |
| 2003/0095993 A1 | 5/2003 | Bentz et al. |
| 2003/0099620 A1 | 5/2003 | Zaleske et al. |
| 2003/0144743 A1 | 7/2003 | Edwards et al. |
| 2003/0198628 A1 | 10/2003 | Hammerman |
| 2003/0225355 A1 | 12/2003 | Butler |
| 2003/0229400 A1 | 12/2003 | Masuda et al. |
| 2003/0236573 A1 | 12/2003 | Evans et al. |
| 2004/0028717 A1 | 2/2004 | Sittinger et al. |
| 2004/0033212 A1 | 2/2004 | Thomson et al. |
| 2004/0039447 A1 | 2/2004 | Simon et al. |
| 2004/0044408 A1 | 3/2004 | Hungerford et al. |
| 2004/0062753 A1 | 4/2004 | Rezania et al. |
| 2004/0078090 A1 | 4/2004 | Binette et al. |
| 2004/0082064 A1 | 4/2004 | Reisner et al. |
| 2004/0102850 A1 | 5/2004 | Shepard |
| 2004/0107003 A1 | 6/2004 | Boyer et al. |
| 2004/0115172 A1 | 6/2004 | Bianchi et al. |
| 2004/0134502 A1 | 7/2004 | Mizuno et al. |
| 2004/0138748 A1 | 7/2004 | Boyer et al. |
| 2004/0143344 A1 | 7/2004 | Malaviya et al. |
| 2004/0151705 A1 | 8/2004 | Mizuno et al. |
| 2004/0166169 A1 | 8/2004 | Malaviya et al. |
| 2004/0170610 A1 | 9/2004 | Slavin et al. |
| 2004/0175826 A1 | 9/2004 | Maor |
| 2004/0192605 A1 | 9/2004 | Zhang et al. |
| 2004/0193154 A1 | 9/2004 | Leatherbury et al. |
| 2004/0193268 A1 | 9/2004 | Hazebrouck |
| 2004/0197311 A1 | 10/2004 | Brekke et al. |
| 2004/0197367 A1 | 10/2004 | Rezania et al. |
| 2004/0197373 A1 | 10/2004 | Gertzman et al. |
| 2004/0197375 A1 | 10/2004 | Rezania et al. |
| 2004/0219182 A1 | 11/2004 | Gomes et al. |
| 2004/0220574 A1 | 11/2004 | Pelo et al. |
| 2004/0230303 A1 | 11/2004 | Gomes et al. |
| 2004/0234549 A1 | 11/2004 | Chiang et al. |
| 2004/0243242 A1 | 12/2004 | Sybert et al. |
| 2004/0267277 A1 | 12/2004 | Zannis et al. |
| 2005/0004672 A1 | 1/2005 | Pafford et al. |
| 2005/0027307 A1 | 2/2005 | Schwartz et al. |
| 2005/0038520 A1 | 2/2005 | Binette et al. |
| 2005/0042254 A1 | 2/2005 | Freyman et al. |
| 2005/0043814 A1 | 2/2005 | Kusanagi et al. |
| 2005/0064042 A1 | 3/2005 | Vunjak-Novakovic et al. |
| 2005/0074476 A1 | 4/2005 | Gendler et al. |
| 2005/0074481 A1 | 4/2005 | Brekke et al. |
| 2005/0089544 A1 | 4/2005 | Khouri et al. |
| 2005/0101957 A1 | 5/2005 | Buskirk et al. |
| 2005/0112761 A1 | 5/2005 | Halvorsen et al. |
| 2005/0125077 A1 | 6/2005 | Harmon et al. |
| 2005/0129668 A1 | 6/2005 | Giannetti et al. |
| 2005/0152882 A1 | 7/2005 | Kizer et al. |
| 2005/0159820 A1 | 7/2005 | Yoshikawa et al. |
| 2005/0159822 A1 | 7/2005 | Griffey et al. |
| 2005/0161857 A1 | 7/2005 | Coombes et al. |
| 2005/0191248 A1 | 9/2005 | Hunter et al. |
| 2005/0196460 A1 | 9/2005 | Malinin |
| 2005/0209705 A1 | 9/2005 | Niederauer et al. |
| 2005/0222687 A1 | 10/2005 | Vunjak-Novakovic et al. |
| 2005/0228498 A1 | 10/2005 | Andres |
| 2005/0240281 A1 | 10/2005 | Slivka et al. |
| 2005/0251268 A1 | 11/2005 | Truncale |
| 2005/0255458 A1 | 11/2005 | Polansky |
| 2005/0260612 A1 | 11/2005 | Padmini et al. |
| 2005/0261681 A9 | 11/2005 | Branch et al. |
| 2005/0261767 A1 | 11/2005 | Anderson et al. |
| 2005/0288796 A1 | 12/2005 | Awad et al. |
| 2006/0030948 A1 | 2/2006 | Manrique et al. |
| 2006/0060209 A1 | 3/2006 | Shepard |
| 2006/0099234 A1 | 5/2006 | Winkler |
| 2006/0105015 A1 | 5/2006 | Perla et al. |
| 2006/0111778 A1 | 5/2006 | Michalow |
| 2006/0167483 A1 | 7/2006 | Asculai et al. |
| 2006/0178748 A1 | 8/2006 | Dinger et al. |
| 2006/0200166 A1 | 9/2006 | Hanson et al. |
| 2006/0204445 A1 | 9/2006 | Atala et al. |
| 2006/0210643 A1 | 9/2006 | Truncale et al. |
| 2006/0216323 A1 | 9/2006 | Knaack et al. |
| 2006/0216822 A1 | 9/2006 | Mizuno et al. |
| 2006/0235534 A1 | 10/2006 | Gertzman et al. |
| 2006/0247790 A1 | 11/2006 | McKay |
| 2006/0247791 A1 | 11/2006 | McKay et al. |
| 2006/0251631 A1 | 11/2006 | Adkisson et al. |
| 2006/0276907 A1 | 12/2006 | Boyer et al. |
| 2006/0286144 A1 | 12/2006 | Yang et al. |
| 2007/0009610 A1 | 1/2007 | Syring |
| 2007/0014867 A1 | 1/2007 | Kusanagi et al. |
| 2007/0026030 A1 | 2/2007 | Gill et al. |
| 2007/0036834 A1 | 2/2007 | Pauletti et al. |
| 2007/0041950 A1 | 2/2007 | Leatherbury et al. |
| 2007/0043376 A1 | 2/2007 | Leatherbury et al. |
| 2007/0055377 A1 | 3/2007 | Hanson et al. |
| 2007/0057175 A1 | 3/2007 | Mordehai et al. |
| 2007/0065943 A1 | 3/2007 | Smith et al. |
| 2007/0067032 A1 | 3/2007 | Felt et al. |
| 2007/0083266 A1 | 4/2007 | Lang |
| 2007/0093896 A1 | 4/2007 | Malinin |
| 2007/0093912 A1 | 4/2007 | Borden |
| 2007/0098759 A1 | 5/2007 | Malinin |
| 2007/0100450 A1 | 5/2007 | Hodorek |
| 2007/0113951 A1 | 5/2007 | Huang |
| 2007/0128155 A1 | 6/2007 | Seyedin et al. |
| 2007/0134291 A1 | 6/2007 | Ting et al. |

(56) References Cited

U.S. PATENT DOCUMENTS

| | | |
|---|---|---|
| 2007/0135917 A1 | 6/2007 | Malinin |
| 2007/0135918 A1 | 6/2007 | Malinin |
| 2007/0135928 A1 | 6/2007 | Malinin |
| 2007/0148242 A1 | 6/2007 | Vilei et al. |
| 2007/0162121 A1 | 7/2007 | Tarrant et al. |
| 2007/0168030 A1 | 7/2007 | Edwards et al. |
| 2007/0172506 A1 | 7/2007 | Nycz et al. |
| 2007/0178159 A1 | 8/2007 | Chen et al. |
| 2007/0179607 A1 | 8/2007 | Hodorek et al. |
| 2007/0185585 A1 | 8/2007 | Bracy et al. |
| 2007/0190030 A1 | 8/2007 | Pawliuk et al. |
| 2007/0202190 A1 | 8/2007 | Borden |
| 2007/0219497 A1 | 9/2007 | Johnson et al. |
| 2007/0276506 A1 | 11/2007 | Troxel |
| 2007/0299517 A1 | 12/2007 | Davisson et al. |
| 2007/0299519 A1 | 12/2007 | Schmieding |
| 2008/0015709 A1 | 1/2008 | Evans et al. |
| 2008/0027546 A1 | 1/2008 | Semler et al. |
| 2008/0031915 A1 | 2/2008 | Becerra Ratia et al. |
| 2008/0038314 A1 | 2/2008 | Hunziker |
| 2008/0039939 A1 | 2/2008 | Iwamoto et al. |
| 2008/0039954 A1 | 2/2008 | Long et al. |
| 2008/0039955 A1 | 2/2008 | Hunziker |
| 2008/0051889 A1 | 2/2008 | Hodorek |
| 2008/0065210 A1 | 3/2008 | McKay |
| 2008/0077251 A1 | 3/2008 | Chen et al. |
| 2008/0119947 A1 | 5/2008 | Huckle et al. |
| 2008/0125863 A1 | 5/2008 | McKay |
| 2008/0125868 A1 | 5/2008 | Branemark et al. |
| 2008/0133008 A1 | 6/2008 | Truncale et al. |
| 2008/0138414 A1 | 6/2008 | Huckle et al. |
| 2008/0153157 A1 | 6/2008 | Yao et al. |
| 2008/0154372 A1 | 6/2008 | Peckham |
| 2008/0166329 A1 | 7/2008 | Sung et al. |
| 2008/0167716 A1 | 7/2008 | Schwartz et al. |
| 2008/0183300 A1 | 7/2008 | Seedhom et al. |
| 2008/0220044 A1 | 9/2008 | Semler et al. |
| 2008/0255676 A1 | 10/2008 | Semler et al. |
| 2008/0260801 A1 | 10/2008 | Ahlers et al. |
| 2008/0274157 A1 | 11/2008 | Vunjak-Novakovic et al. |
| 2008/0287342 A1 | 11/2008 | Yu et al. |
| 2008/0305145 A1 | 12/2008 | Shelby et al. |
| 2008/0306408 A1 | 12/2008 | Lo |
| 2009/0001267 A1 | 1/2009 | Enyama et al. |
| 2009/0043389 A1 | 2/2009 | Vunjak-Novakovic et al. |
| 2009/0069901 A1 | 3/2009 | Truncale et al. |
| 2009/0069904 A1 | 3/2009 | Picha |
| 2009/0076624 A1 | 3/2009 | Rahaman et al. |
| 2009/0099661 A1 | 4/2009 | Bhattacharya et al. |
| 2009/0112119 A1 | 4/2009 | Kim |
| 2009/0117652 A1 | 5/2009 | Luyten et al. |
| 2009/0131986 A1 | 5/2009 | Lee et al. |
| 2009/0139045 A1 | 6/2009 | Cannon et al. |
| 2009/0143867 A1 | 6/2009 | Gage et al. |
| 2009/0149893 A1 | 6/2009 | Semler et al. |
| 2009/0210057 A1 | 8/2009 | Liao et al. |
| 2009/0226523 A1 | 9/2009 | Behnam et al. |
| 2009/0280179 A1 | 11/2009 | Neumann et al. |
| 2009/0291112 A1 | 11/2009 | Truncale et al. |
| 2009/0299475 A1 | 12/2009 | Yamamoto et al. |
| 2009/0312805 A1 | 12/2009 | Lang et al. |
| 2009/0312842 A1 | 12/2009 | Bursac et al. |
| 2009/0319051 A9 | 12/2009 | Nycz et al. |
| 2010/0015202 A1 | 1/2010 | Semler et al. |
| 2010/0021521 A1 | 1/2010 | Xu et al. |
| 2010/0036492 A1 | 2/2010 | Hung et al. |
| 2010/0036503 A1 | 2/2010 | Chen et al. |
| 2010/0241228 A1 | 9/2010 | Syring et al. |
| 2010/0274362 A1 | 10/2010 | Yayon et al. |
| 2010/0291181 A1 | 11/2010 | Uhrich et al. |
| 2011/0053841 A1 | 3/2011 | Yayon et al. |
| 2011/0070271 A1 | 3/2011 | Truncale et al. |
| 2011/0196508 A1 | 8/2011 | Truncale et al. |
| 2011/0224797 A1 | 9/2011 | Semler et al. |
| 2013/0273121 A1 | 10/2013 | Mizuno et al. |

FOREIGN PATENT DOCUMENTS

| | | |
|---|---|---|
| EP | 0517030 A2 | 12/1992 |
| EP | 0522569 A1 | 1/1993 |
| EP | 0608546 A2 | 8/1994 |
| EP | 0674908 A1 | 10/1995 |
| EP | 0677297 A1 | 10/1995 |
| EP | 0739631 A2 | 10/1996 |
| EP | 0784985 A1 | 7/1997 |
| EP | 1127581 A1 | 8/2001 |
| EP | 1181908 A1 | 2/2002 |
| EP | 1208850 A1 | 5/2002 |
| EP | 1234552 A1 | 8/2002 |
| EP | 1234555 A2 | 8/2002 |
| EP | 1264607 A1 | 12/2002 |
| EP | 1384452 A1 | 1/2004 |
| EP | 1452191 A2 | 9/2004 |
| EP | 1537883 A2 | 6/2005 |
| EP | 1561481 A2 | 8/2005 |
| EP | 1625832 A1 | 2/2006 |
| EP | 1719463 A1 | 11/2006 |
| EP | 1719531 A2 | 11/2006 |
| EP | 1719532 A2 | 11/2006 |
| EP | 1923457 A1 | 5/2008 |
| FR | 2657352 A1 | 7/1991 |
| GB | 2102811 A | 2/1983 |
| JP | 622744 | 2/1994 |
| WO | 90/01342 A1 | 2/1990 |
| WO | 90/11354 A1 | 10/1990 |
| WO | 91/01140 A1 | 2/1991 |
| WO | 91/09126 A1 | 6/1991 |
| WO | 93/04169 A1 | 3/1993 |
| WO | 93/16739 A1 | 9/1993 |
| WO | 93/20218 A1 | 10/1993 |
| WO | 94/03584 A1 | 2/1994 |
| WO | 94/29442 A2 | 12/1994 |
| WO | 95/25748 A1 | 9/1995 |
| WO | 95/33502 A1 | 12/1995 |
| WO | 96/01313 A1 | 1/1996 |
| WO | 96/03159 A1 | 2/1996 |
| WO | 96/15818 A1 | 5/1996 |
| WO | 96/24310 A1 | 8/1996 |
| WO | 96/40892 A1 | 12/1996 |
| WO | 97/07668 A1 | 3/1997 |
| WO | 97/07669 A1 | 3/1997 |
| WO | 97/29715 A1 | 8/1997 |
| WO | 97/40163 A1 | 10/1997 |
| WO | 98/14222 A1 | 4/1998 |
| WO | 98/41246 A2 | 9/1998 |
| WO | 98/43686 A1 | 10/1998 |
| WO | 98/44874 A1 | 10/1998 |
| WO | 99/09914 A1 | 3/1999 |
| WO | 99/11298 A2 | 3/1999 |
| WO | 99/15209 A2 | 4/1999 |
| WO | 99/21497 A1 | 5/1999 |
| WO | 99/22747 A1 | 5/1999 |
| WO | 99/48541 A1 | 9/1999 |
| WO | 99/52572 A1 | 10/1999 |
| WO | 99/56797 A1 | 11/1999 |
| WO | 00/40177 A1 | 7/2000 |
| WO | 00/44808 A1 | 8/2000 |
| WO | 00/47114 A1 | 8/2000 |
| WO | 00/47214 A1 | 8/2000 |
| WO | 01/02030 A2 | 1/2001 |
| WO | 01/07595 A2 | 2/2001 |
| WO | 01/38357 A2 | 5/2001 |
| WO | 01/39788 A2 | 6/2001 |
| WO | 01/43667 A2 | 6/2001 |
| WO | 01/46416 A1 | 6/2001 |
| WO | 02/18546 | 3/2002 |
| WO | 02/22779 A2 | 3/2002 |
| WO | 02/36732 A2 | 5/2002 |
| WO | 02/41877 A1 | 5/2002 |
| WO | 02/058484 A2 | 8/2002 |
| WO | 02/064180 A1 | 8/2002 |
| WO | 02/077199 A2 | 10/2002 |
| WO | 02/095019 A1 | 11/2002 |
| WO | 03/007805 A2 | 1/2003 |
| WO | 03/007873 A2 | 1/2003 |

(56) References Cited

FOREIGN PATENT DOCUMENTS

| | | | |
|---|---|---|---|
| WO | 03/007879 A2 | 1/2003 |
| WO | 03/012053 A2 | 2/2003 |
| WO | 03/035851 A1 | 5/2003 |
| WO | 03/040113 A1 | 5/2003 |
| WO | 03/049626 A1 | 6/2003 |
| WO | 03/079985 A2 | 10/2003 |
| WO | 03/087160 A1 | 10/2003 |
| WO | 03/094835 A2 | 11/2003 |
| WO | 2004/016276 A1 | 2/2004 |
| WO | 2004/060404 A1 | 7/2004 |
| WO | 2004/067704 A2 | 8/2004 |
| WO | 2004/069298 A1 | 8/2004 |
| WO | 2004/075940 A1 | 9/2004 |
| WO | 2004/096983 A2 | 11/2004 |
| WO | 2004/103224 A1 | 12/2004 |
| WO | 2005/023321 A2 | 3/2005 |
| WO | 2005/023906 A1 | 3/2005 |
| WO | 2005/058207 A1 | 6/2005 |
| WO | 2005/110278 A2 | 11/2005 |
| WO | 2006/001046 A1 | 1/2006 |
| WO | 2006/038287 A1 | 4/2006 |
| WO | 2006/042311 A2 | 4/2006 |
| WO | 2006/050213 A2 | 5/2006 |
| WO | 2006/113586 A2 | 10/2006 |
| WO | 2007/024238 A1 | 3/2007 |
| WO | 2007/035778 A2 | 3/2007 |
| WO | 2007/057175 A2 | 5/2007 |
| WO | 2008/013763 A2 | 1/2008 |
| WO | 2008/021127 A2 | 2/2008 |
| WO | 2008/038287 A2 | 4/2008 |
| WO | 2008/081463 A2 | 7/2008 |
| WO | 2008/106254 A2 | 9/2008 |
| WO | 2009/076164 A2 | 6/2009 |
| WO | 2009/111069 A1 | 9/2009 |
| WO | 2010/083051 A2 | 7/2010 |

OTHER PUBLICATIONS

Zhang et. al., 2004, Hyaline cartilage engineered by chondrocytes in pellet culture: histological., immunohistochemical and ultrastructural analysis in comparison with cartilage explants, J. Anat., 205(3):229-37.
Zhu et. al., 1995, GLU-96 of Basic Fibroblast Growth Factor is Essential for High Affinity Receptor Binding Journal of Biological Chemistry, American, Society of Biochemical Biologists, Birmingham US, 270(37):21869-21874.
Zhu et. al., 1997, Analysis of high-affinity binding determinants in the receptor binding epitope of basic fibroblast growth factor, Protein Engineering, 10:417-421.
Supplementary European Search Report for EP02753826 dated Jul. 17, 2009, 2 pages.
Supplementary European Search Report for EP08768602 dated Oct. 22, 2012, 6 pages.
Supplementary European Search Report for EP087983003.3 dated Oct. 18, 2012, 6 pages.
Taylor et. al., 2002, In vitro osteoclast resorption of bone substitute biomaterials used for implant site augmentation: a pilot study, Int J Oral Maxillofac Implants, 17(3):321-30.
Thomson et. al., 1995, Fabrication of Biodegradable Polymer Scaffolds to Engineer Trabecular Bones, J Biomater Sci Polymer Edn, 7(1) :23-38.
Thuerauf et. al., 1997, Differential Effects of Protein Kinase C, Ras, and Raf-1 Kinase on the Induction of the Cardiac B-type Natriuretic Peptide Gene through a Critical Promoter-proximal M-CAT Element, J Biol Chem., 272:7464-7472.
Tokuriki et. al., 2009, Stability effects of mutations and protein evolvability, Current Opinion in Structural Biology, 19:596-604.
Tozer et. al., 2005, Tendon and ligament: Development, repair and disease, Birth Defects Research Part C, 75(3):226-236.
Tsumaki et. al., 1999, Role of CDMP-1 in Skeletal Morphogenesis: Promotion of Mesenchymal Cell Recruitment and Chondrocyte Differentiation, J Cell Biol., 144(1):161-173.
Ui-Tei et. al., 2004, Guidelines for the selection of highly effective siRNA sequences for mammalian and chick RNA interference, NAR 32(3):936-48.
Vajo et. al., 2000, The Molecular and Genet.ic Basis of Fibroblast Growth Factor Receptor 3 Disorders: The Achondroplasia Family of Skelet.al Dysplasias Muenke Craniosynostosis, and Crouzon Syndrome with Acanthosis Nigricans, Endocrine Rev 21(1):23-39.
Venkatesan et. al., 2004, Stimulation of proteoglycan synthesis by glucuronosyltransferase-I gene delivery: a strategy to promote cartilage repair, PNAS,11(52):18087-92.
Verbruggen et. al., 1985, Repair Function in Organ Cultured Human Cartilage. Replacement of Enzymatically Removed Proteoglycans During Long term Organ Culture, The Journal of Rheumatology, 12(4):665-674.
Vidal et. al., 2005, Making sense of antisense, European Journal of Cancer, 41:2812-2818.
Vunjak-Novakovic et. al., 1999, Bioreactor Cultivation Conditions Modulate the Composition and Mechanical Properties of Tissue-Engineered Cartilage, Journal of Orthopaedic Research, 17:130-138.
Wada et. al., 1992, Codon usage tabulated from the GenBank genetic sequence data, Nucleic Acids Research, 20 (Supplement):2111-2118.
Walsh et. al., 2003, Multiple tissue-specific promoters control expression of the murine tartrate-resistant acid phosphatase gene, Gene, 307:111-123.
Wang et. al., 1999, Overexpression of protein kinase C-? in the epidermis of transgenic mice results in striking alterations in phorbol ester-induced inflammation and COX-2, MIP-2 and TNF-alpha expression but not tumor promotion, Journal of Cell Science, 112:3497-3506.
Wells et. al., 1990, Additivity of Mutational Effects in Proteins, Biochemistry, 29(37):8509.
Wilson et. al., 1977, Biological Properties of Polio Virus Encapsulated in Lipio Vesicles, Proc Natl Acad Sci, 74(8):3471-3475.
Winkler, 2013, Oligonucleotide conjugates for therapeutic applications, Ther Deliv., 4:791-809.
Wise et. al., 2002, American Surgeon, 68(6):553-end.
Wong et. al., 1995, Analysis of Putative Heparin-binding Domains of Fibroblast Growth Factor-1: Using Site-Directed Directed Mutagenesis and Peptide Analogues, The Journal of Biological Chemistry, 270(43):25805-25811.
Woods et. al., 2005, Effectiveness of three extraction techniques in the development of a decellularized bone-anterior cruciate ligament-bone graft, Biomaterials, 26:7339-7349.
Wu et. al., 2009, Multiple Synostoses Syndrome is Due to a Missense Mutation in Exon 2 of FGF9 Gene, The American Journal of Human Genetics, 85:53-63.
Yamashita et. al., 2000, Identification of a Novel Fibroblast Growth Factor, FGF-23, Preferentially Expressed in the Ventrolateral Thalamic Nucleus of the Brain, Biochemical and Biophysical Research Communications, 277:494-498.
Yang et. al., 1998, Improved fluorescence and dual color detection with enhanced blue and green variants of the green fluorescent protein, Journal of Biological Chemistry, 273:8212-6.
Yang et. al., 2000, Rac2 stimulates Akt activation affecting BAD/Bcl-XL expression while mediating survival and actin function in primary mast cells, Immunity, 12(5):557-568.
Yayon et. al., 1991, Cell Surface, Heparin-Like Molecules are Required for Binding of Basic Fibroblast Growth Factor to Its High Affinity Receptor, Cell, 64:841-848.
Yayon et. al., 1993, Isolation of peptides that inhibit binding of basic fibroblast growth factor to its receptor from a random phage-epitope library, Proc. Natl. Acad. Sci. USA, 90:10643-10647.
Yee et. al., 2000, Analysis of Fibroblast Growth Factor Receptor 3 S249C Mutation in Cervical Carcinoma, Journal of the National Cancer Institute, 92(22):1848-1849.
Young's Modulus, Entry on http://enwikipecliaorg accessed Oct, 27, 2005, 3 pages.
Zhang et. al., 1991, Three-dimensional structure of human basic fibroblast growth factor, a structural homology of interleukin 1 Beta, Proc. Natl. Acad. Sci. USA, 88(8):3446-3450.

(56) References Cited

OTHER PUBLICATIONS

Zhang et. al., 1997, Directed evolution of a fucosidase from a galactosidase by DNA shuffling and screening, Proc. Natl. Acad. Sci. USA, 94:4504-4509.
Phillips, 2001, The challenge of gene therapy and DNA delivery, Journal of Pharmacy and Pharmacology, 53:1169-1174.
Pillai et. al., 2001, Polymers in Drug Delivery, Current Opinion Chemical Biology, 5:447-451.
Plotnikov et. al., 1999, Structural Basis for FGF Receptor Dimerization and Activation, Cell, 98:641-650.
Plotnikov et. al., 2000, Crystal Structures of Two FGF-FGFR Complexes Reveal the Determinants of Ligand-Receptor Specificity, Cell 101:413-424.
Pollik et. al., 1995, J Oral Maxillofac Surg, 53(8):915-22.
Pouyani et. al., 1994, Functionalized Derivatives of Hyaluronic Acid Oligosaccharides: Drug Carriers and Novel Biomaterials, Bioconjugate Chem., 5:339-347.
Presta et. al., 1993, Subcellular Localization and Biological Activity of Mr 18,000 Basic Fibroblast Growth Factor: Site-Directed Directed Mutagenesis of a Putative Nuclear Translocation Sequence, Growth Factors, 9:269-278.
Prestwich et. al., 1998, Controlled chemical modification of hyaluronic acid: synthesis, applications, and biodegradation of hydrazide derivatives, Journal of Controlled Release, 53:93-103.
Rabie et. al., 1996, Ultrastructural identification of cells involved in the healing of intramembranous and endochondral bones, Int J Oral Maxillofac Surg, 25(5):383-388.
Raisz, 1999, Physiology and Pathophysiology of Bone Remodeling, Clinical Chemistry, 45(8):1353-1358.
Richardson et. al., 1999, Repair of human articular cartilage after implantation of autologous chondrocytes, Journal of Bone and Joint Surgery [Br], 81-B:1064-1068.
Riggs et. al., 1987, Luciferase reporter gene cassettes for plant gene expression studies, Nucleic Acid Res 15(19):8115.
Sahni et. al., 1999, FGF signaling inhibits chondrocyte proliferation and regulates bone development through the STAT-1 pathway Genes Dev., 13(11):1361-1386.
Santos-Ocampo et. al., 1996, Expression and Biological Activity of Mouse Fibroblast Growth Factor-9:, The Journal of Biological Chemistry, 271:1726-1731.
Schaefer et. al., 2002, Tissue Engineered Composites for the Repair of Large Osteochondral Defects, Arthritis & Rheumatism, 46(9):2524-2534.
Schlessinger et. al., 2000, Crystal Structure of a Ternary FGF-FGFR-Heparin Complex Reveals a Dual Role for Heparin in FGFR Binding and Dimerization, Molecular Cell, 6:743-750.
Schmal et. al., 2007, bFGF influences human articular chondrocyte differentiation, Cytotherapy, 9(2):184-193.
Schwartz et. al., 1991, A dominant positive and negative selectable gene for use in mammalian cells, Proc. Natl. Acad. Sci. USA, 88(23):10416-20.
Schwarz et. al., 2000, Quantitative small-animal surrogate to evaluate drug efficacy in preventing wear debris-induced osteolysis, J Orthop Res, 18:849-55.
Schwindt et. al., 2009, Effects of FGF-2 and EGF removal on the differentiation of mouse neural precursor cells, An Acad Bras Cienc, 81(3):443-452.
Seddon et. al., 1995, Engineering of Fibroblast Growth Factor: Alteration of Receptor Binding Specificity, Biochemistry, 34:741-736.
Shaklee et. al., 1984, Hydrazinolysis of heparin and other glycosaminoglycans, Biochem. J., 217:187-197.
Shao et. al., 2006, Effects of intramyocardial administration of slow-release basic fibroblast growth factor on angiogenesis and ventricular remodeling in a rat infarct model, Circ J, 70(4):471-477.
Shibata et. al., 2001, GM-CSF Regulates Alveolar Macrophage Differentiation and Innate Immunity in the Lung through PU.1, Immunity, 15(4):557-567.

Shu et. al., 2003, Attachment and spreading of fibroblasts on an RGD peptide-modified injectable hyaluronan hydrogel, Wiley periodicals.
Shu et. al., 2004, Attachment and spreading of fibroblasts on an RGD peptide-modified injectable hyaluronan hydrogel, J Biomed, Mater Res 68A:365-375.
Sims et al., 1998, Tissue Engineered Neocartilage Using Plasma Derived Polymer Substrates and Chondrocytes, Plastic & Recon Surg 101(6):1580-1585.
Skolnick et. al., 2000, From genes to protein structure and function: novel applications of computational approaches in the genomic era, Trends BioTechnol, 18(1):34-39.
Sleeman et. al., 2001, Identification of a new fibroblast growth factor receptor, FGFR5, Gene, 271(2): 171-182.
Smith et. al., 1996, In vitro stimulation of articular chondrocyte mRNA and extracellular matrix synthesis by hydrostatic pressure, Journal of Orthopaedic Research, John Wiley & Sons, Inc, 14(1):53-60.
Smith et. al., 1997, The challenges of genome sequence annotation or The devil is in the details, Nature Biotechnology, 15(12):1222-1223.
Soltes et. al., 2003, Molecular characterization of two host-guest associating hyaluronan derivatives, Biomedical Chromatography, 17;376-384.
Song et. al., 2002, Construction of DNA-Shuffled and Incrementally Truncated Libraries by a Mutagenic and Unidirectional Reassembly Method: Changing from a Substrate Specificity of Phospholipase to That of Lipase, Appl. Environ. Microbiol., 68(12):6146-6151.
Spangenberg et. al., 2002, Histomorphometric Analysis of a Cell-Based Model of Cartilage Repair, Tissue Engineering, 8(5):839-46.
Springer et. al., 1994, Identification and Concerted Function of Two Receptor:Binding Surfaces on Basic Fibroblast Growth Factor Required for Mitogenesis, The Journal of Biological Chemistry, 269(43):26879-26884.
Stauber et. al., 2000, Structural interactions of fibroblast growth factor receptor with its ligands, PNAS, 97(1):49-54.
Stemmer et. al., 1994, DNA shuffling by random fragmentation and reassembly: in vitro recombination for molecular evolution, Proc. Natl. Acad. Sci. USA, 91(22):10747-10751.
Stone et. al., 2006, Articular Cartilage Paste Grafting to Full-Thickness Articular Cartilage Knee Joint Lesions: A 2- to 12-Year Follow-up, Arthroscopy: The Journal of Arthroscopic and Related Surgery, 22(3):291-299.
Stone et. al., One-Step American Technique of Articular Cartilage Paste Grafting to Traumatic and Arthritic Defects in the Knee Joint (2-7 Years Follow-Up), downloaded from http:webarchive.Org/web/20041205005845/http://www.stoneclinic.com/onestepthm:published Dec. 5, 2004.
Sun et. al., 2001, Quantitative imaging of gene induction in living animals, Gene Therapy, 8:1572-1579.
Famdale et. al., 1982, A Direct Spectrophotometric Microassay for Sulfated Glycosaminoglycans in Cartilage Cultures, Connective Tissue Research, 9(4):247-248.
Feczko et. al., 2003, Experimental Results of Donor Site Filling for Autologous Osteochondral Mosaicplasty, Arthroscopy: The Journal of Arthroscopic and Related Surgery, 19(7):755-761.
Fingl et. al., 1975, The Pharmacological Basis of Therapeutics, Ch 1: I.
Foldynova-Trantirkova et. al., 2012, Sixteen years and counting: the current understanding of fibroblast growth factor receptor 3 (FGFR3) signaling in skeletal dysplasias, Human Mutation, 33:29-41.
Fujibayashi et. al., 2001, J Long Term Eff Med Implants:11:93-103.
Fujisato et. al., 1996, Effect of basic fibroblast growth factor on cartilage regeneration in chondrocyte-seeded collagen sponge scaffold, Biomaterials, 17:155-162.
Furth, et. al.,1994, Temporal control of gene expression in transgenic mice by a tetracycline-responsive promoter, Proc Natl Acad Sci USA, 91:9302-9306.
Gao et. al., 2002, Repair of Osteochondral Defect with Tissue-Engineered Two-Phase Composite Material of Injectable Calcium Phosphate and Hyaluronan Sponge, Tissue Engineering Part A 8(5):827-837.

(56) References Cited

OTHER PUBLICATIONS

Gargiulo et. al., 2002, Phenotypic modulation of human articular chondrocytes by bistratene A, Eur Cell Mater, 3:9-18.
Garofalo et. al., 1999, Skeletal Dysplasia and Defective Chondrocyte Differentiation by targeted Overexpression of Fibroblast Growth Factor 9 in Transgenic Mice, Journal of Bone and Mineral Research, 14(11):1909-1915.
George et. al., 2006, Differentiation of Mesenchymal Stem Cells Into Osteoblasts on Honeycomb Collagen Scaffolds, Artificial Organs, 25(3):180-186.
George et. al., 2008, Biodegradable honeycomb collagen scaffold for dermal tissue engineering, J Biomed Mater Res 87A:1103-1111.
Gertzman et. al., 2001, A pilot study evaluating sodium hyaluronate as a carrier for freeze-dried demineralized bone powder, Cell and Tissue Banking, 2:87-94.
Gilbert et. al., 2006, Decellularization of Tissues and Organs, Biomaterials, 27(19):3675-3683.
Givol et. al., 1992, Complexity of FGF receptors: genetic basis for structural diversity and functional specificity, FASEB J., 6:3362-3369.
Glowacki et. al., 2001, Engineered Cartilage, Bone, Joints and Menisci-Potential for Temporomandibular Joint Reconstruction, Cells Tissues Organs, 169(3):302-308.
Goldberg et. al., 2005, Intra-articular hyaluronans: the treatment of knee pain in osteoarthritis, Osteoarthritis Cartilage, 13(3):216-224.
Gooch et.al., 2001, IGF-I and Mechanical Environment Interact to Modulate Engineered Cartilage Development, Biochemical and Biophysical Research Communications, 286:909-915.
Gruber et. al., 2002, Platelets stimulate proliferation of bone cells: involvement of platelet.derived growth factor, microparticles and membranes, Clin Oral Implants Res., 13(5):529-535.
Guilak et. al., 2001, Functional tissue engineering: the role of biomechanics in articular cartilage repair. Clin Orthop Relat Res., (391 Suppl):S295-305.
Haisch et. al., 2000, Preparation of a pure autologous biodegradable fibrin matrix for tissue engineering, Cellular Engineering, Medical & Biological Engineering & Computing, 38:686-689.
Hayes et. al., 2002, Combining computational and experimental screening for rapid optimization of protein properties, Proc Natl Acad Sci U S A, 99:15926-31.
Hecht et. al., 2001, Structure of fibroblast growth factor 9 shows a symmetric dimer with unique receptor- and heparin-binding interfaces, Acta Crystallogr D Biol Crystallogr, 57:378-384.
Herrera-Estrella et. al., 1983, Chimeric genes as dominant selectable markers in plant cells, EMBO J., 2(6):987-995.
Hidaka et. al., 2003, Acceleration of cartilage repair by genetically modified chondrocytes overexpressing bone morphogenetic protein-7, J Orthop Res, 21(4):573-83.
Hille et. al., 1990, Bleomycin resistance: a new dominant selectable marker for plant cell transformation, Plant Molecular Biology, 7:171-176.
Hoffman, 2002, Hydrogels for Biomedical Applications, Advanced Drug Delivery Reviews, 54(1):3-12.
Hromas et. al., 1993, Hematopoietic lineage- and stage-restricted expression of the ETS oncogene family member PU.1, Blood 82:2998-3004.
Hunziker, 1992, Articular Cartilage Structure in Humans and Experimental Animals, Articular Cartilage and Osteoarthritis, Raven Press, ed:183-199.
Hunziker, 1999, Articular cartilage repair: are the intrinsic biological constraints undermining this process insuperable?, Osteoarthritis and Cartilage 7(1):15-28.
Hunziker, 2001, Articular Cartilage Repair: Basic Science and Clinical Progress a Review of the Current Status and Prospects, Osteoarthritis and Cartilage, 10(6):432-463.
Ikeda et. al., 2000, Ex vivo gene delivery using an adenovirus vector in treatment for cartilage defects, J Rheumatol, 27(4):990-6.
Imamura et. al., 1990, Recovery of Mitogenic Activity of a Growth Factor Mutant with a Nuclear Translocation Sequence, Science, 249:1567-1570.

International Preliminary Examination Report for PCT/US02/09001 dated Oct. 30, 2004, (7 pages).
International Preliminary Report on Patentability for PCT/US2008/073762 dated Feb. 24, 2010, (6 pages).
Bikfalvi et. al., 1997, Biological Roles of Fibroblast Growth Factor-2, Endocrine Reviews, 18(I):26-45.
Blessing et. al., 1993, Transgenic mice as a model to study the role of TGF-beta-related molecules in hair follicles, Genes Dev, 7:204-215.
Bolander, 1992, Regulation of fracture repair by growth factors, Proc Soc Exp Biol Med., 200(2):165-170.
Bork et. al., 1996, Go hunting in sequence databases but watch out for the traps, Trends in Genetics 12(10):425-427.
Bork, 2000, Powers and pitfalls in sequence analysis: The 70% hurdle, Genome Res 10(4):398-400.
Borok et. al., 2000, Differential regulation of rat aquaporin-5 promoter/enhancer activities in lung and salivary epithelial cells, J Biol Chem, 275:26507-14.
Bradford, 1976, A Rapid and Sensitive Method for the Quantitation of Micro-gram Quantities of Protein Utilizing the Principle of Protein-Dye Binding, Analytical Biochemistry, 72(1-2):248-254.
Bradley, 1987, Production and analysis of chimaeric mice. In Teratocarcinomas and Embryonic Stem Cells—A Practica Approach:113-152.
Breinan et. al., 1997, Effect of Cultured Autologous Chondrocytes on Repair of Chondral Defects in a Canine Model, Journal of Bone and Joint Surgery [Am], 79-A(10):1439-1451.
Breinan et. al., 2001, Autologous Chondrocyte Implantation in a Canine Model: Change in Composition of Reparative Tissue with Time, Journal of Orthopaedic Research, 19:482-492.
Brenner, 1999, Errors in genome annotation, Trends in Genetics 15(4):132-133.
Brittberg et. al., 1994, Treatment of Deep Cartilage Defects in the Knee with Autologous Chondrocyte Transplantation, New England Journal of Medicine, 331(14):889-895.
Brittberg et. al., 1996, Rabbit Articular Cartilage Defects Treated with Autologous Cultured Chondrocytes, Clinical Orthopaedics and Related Research, 326:270-283.
Brittberg et. al., 2001, Autologous Chondrocytes Used for Articular Cartilage Repair: An Update, Clinical Orthopaedics and Related Research, 391 Suppl: S337-S348.
Brown et. al., 2005, Hyaluronic acid: a unique topical vehicle for the localized delivery of drugs to the skin, JEADV, 19(3):308-318.
Buckwalter et. al., 1998, Articular Cartilage: Degeneration and Osteoarthritis, Repair, Regeneration, and Transplantation, AAOS Instructional Course Lectures, 47:487-504.
Bugbee, 2000, Fresh Osteochondral Allografting, Operative Techniques in Sports Medicine, 8(2):158-162.
Bujard, 1999, Controlling genes with tetracyclines, J Gene Med, 1:372-374.
Bulpitt et al., 1999, New strategy for chemical modification of hyaluronic acid: Preparation of functionalized derivatives and their use in the formation of novel biocompatible hydrogels, J Biomed Mater Res, 47:152-169.
Burdette et. al., 1996, Cloning and expression of the gene encoding the Thermoanaerobacter ethanolicus 39E secondary-alcohol dehydrogenase and biochemical characterization of the enzyme, Biochem J, 316:115-122.
Burger et. al., 2002, Fibroblast growth factor receptor-1 is expressed by endothelial progenitor cells, Blood, 100(10):3527-35.
Bursac, 2002, Collagen Network Contributions to Structure-Function Relationships in Cartilaginous Tissues in Compression (Dissertation), Boston University College of Engineering.
Bystricky et. al., 2001, Nonbiodegradable hyaluronan derivative prepared by reaction with a water-soluble carbodiimide Chem Paper, 1:49-52.
Cappellen et. al., 1999, Frequent Activating Mutations of FGFR3 in Human Bladder and Cervix Carcinomas, Nature Genetics, 23:18-20.
Carr, 1988, Fibrin formed in plasma is composed of fibers more massive than those formed from purified fibrinogen, Thromb Haemost., 59(3):535-539.

(56) References Cited

OTHER PUBLICATIONS

Chalfie et. al., 1994, Green fluorescent protein as a marker for gene expression, Science 263:802-805.
Charron et. al., 1999, Cooperative Interaction between GATA-4 and GATA-6 Regulates Myocardial Gene Expression, Molecular & Cellular Biology 19(6):4355-4365.
Chellaiah et. al., 1994, Fibroblast Growth Factor Receptor (FGFR) 3, The Journal of Biological Chemistry 269(15):11620-11627.
Chen et. al., 1999, Repair of Articular Cartilage Defects: Part I Basic Science of Cartilage Healing, The American Journal of Orthopedics:31-33.
Chole et. al., 2001, JARO 2:65-71.
Chusho et. al., 2001, Dwarfism and Early Death in Mice Lacking C-Type Natriuretic Peptide, PNAS, 98(7):4016-4021.
Coffin et. al., 1997, Retroviruses Cold Spring Harbor Laboratory Press:758-763.
Colombier et. al., 1999, Cells Tissues Organs 164:131-140.
Communication pursuant to Article 94(3) EPC for European Patent Application No. 06814983.0, dated Sep. 23, 2013, 6 pages.
Cook et. al., 2003, Biocompatibility of three-dimensional chondrocyte grafts in large tibial defects of rabbits, Am J Vet. Res 64(1):12-20.
Messner et. al., 1996, The Long-term Prognosis for Severe Damage to Weight-bearing Cartilage in the Knee: A 14-year Clinical and Radiographic Follow-up in 28 Young Athletes, Acta Orthopaedica Scandinavica, 67(2):165-168.
Mitani et. al., 1994, Generation of the AML1-EVI-1 fusion gene in the t(3;21)(q26;q22) causes blastic crisis in chronic myelocytic leukemia, EMBO J., 13(3):504-510.
Miyamoto et al., 1993, Molecular Cloning of Novel Cytokine cDNA Encoding the Ninth Member of the Fibroblast Growth Factor Family, Which has a Unique Secretion Property, Molecular and Cellular Biology, 13:4251-4259.
Miyazaki, 2002, Random DNA fragmentation with endonuclease V: application to DNA shuffling, Nucleic Acids Research, 30(24):E139.
Mohammadi et. al., 2005, Structural Basis for Fibroblast Growth Factor Receptor Activation, Cytokine & Growth Factor Rev., 16:107-137.
Morishita et. al., 1992, Activation of the EVI1 gene expression in human acute myelogenous leukemias by translocations spanning 300-400 kilobases on chromosome 3q26, Proc. Natl. Acad. Sci. USA, 89:3937-3941.
Morishita et. al., 1992, Expression of the Evi-1 zinc finger gene in 32Dc13 myeloid cells blocks granulocytic differentiation in response to granulocyte colony-stimulating factor, Mol Cell Biol., 12:183-189.
Mucenski et. al., 1988, Identification of a Common Ecotropic Viral Integration Site, Evi-1, in the DNA of AKXD Murine Myeloid Tumors, Molecular and Cellular Biology, 8:301-308.
Nakatake et. al., 2001, Identification of a Novel Fibroblast Growth Factor, FGF-22, Preferentially Expressed in the Inner Root Sheath of the Hair Follicle, Biochimica et. Biophysica Acta, 1517:460-463.
Naruo et. al., 1993, Novel Secretory Heparin-binding Factors from Human Glioma Cells (Glia-activating Factors) Involved in Glial Cell Growth, The Journal of Biological Chemistry, 268(4):2857-2864.
Needleman et. al., 1970, A General Method Applicable to the Search for Similarities in the Amino Acid Sequence of Two Proteins, J. Mol. Biol., 48:443-453.
Nehrer et. al., 1998, Chondrocyte-seeded Collagen Matrices Implanted in a Chondral Defect in a Canine Model, Biomaterials, 19:2313-2328.
Nettles et. al., 2004, in Situ Crosslinkable Hyaluronan for Articular Cartilage Repair, 50th Annual Meeting of the Orthopaedic Research Society, Paper No. 0202.
Nettles et. al., 2004, Photocrosslinkable Hyaluronan as a Scaffold for Articular Cartilage Repair, Annals of Biomedical Engineering, 32(3):391-397.
Neville-Webbe et al., 2002, The anti-tumour activity of bisphosphonates, Cancer Treatement Reviews 28(6):305-319.
Newman, 1998, Articular Cartilage Repair, American Journal of Sports Medicine, 26(2):309-324.
Ngo et. al., 1994, Computational complexity, protein structure prediction, and the Levinthal Paradox, In: The Protein Folding Problem and Tertiary Structure Prediction K Merz Jr and S Le Grand, Editors:433-506.
Nishimura et. al., 2000, Identification of a Novel FGF, FGF-21, Preferentially Expressed in the Liver, Biochimica et. Biophysica Acta, 1492:203-206.
Nixon et. al., 1999, Enhanced Repair of Extensive Articular Defects by Insulin-like Growth Factor-I-Laden Fibrin Composites, Journal of Orthopaedic Research, 17(4):475-487.
O'Gorman et. al., 1991, Recombinase-mediated gene activation and site-specific integration in mammalian cells, Science, 251:1351-1355.
Obradovic et. al., 2001, Integration of Engineered Cartilage, Journal of Orthopaedic Research, 19:1089-1097.
Ochi et. al., 2001, Current Concepts in Tissue Engineering Technique for Repair of Cartilage Defect, Artificial Organs, 25(3):172-179.
Office Action for Canadian Patent Application No. 2,623,106, dated Jul. 10, 2012, 3 pages.
Office Action for Canadian Patent Application No. 2,623,106, dated Oct. 6, 2011, 4 pages.
Oh et. al., 2003, Signaling Mechanisms Leading to the Regulation of Differentiation and Apoptosis of Articular Chondrocytes by Insulin-like Growth Factor-1, Journal of Biological Chemistry, 278(38):36563-36571.
Okada-Ban et. al., 2000, Molecules in focus, Fibroblast Growth Factor-2, The International Journal of Biochemistry & Cell Biology, 32:263-267.
Olsen et. al., 2003, Fibroblast Growth Factor (FGF) Homologous Factors Share Structural but not Functional Homology with FGFs, J. Biol. Chem., 278(36):34226-34236.
Olsen et. al., 2004, Insights into the Molecular Basis for Fibroblast Growth Factor Receptor Autoinhibition and Ligand-Binding Promiscuity, Proc. Natl. Acad. Sci., 101:935-940.
Ornitz et. al., 1992, Ligand Specificity and Heparin Dependence of Fibroblast Growth Factor Receptors 1 and 3, The Journal of Biological Chemistry, 267(23):16305-16311.
Ornitz et. al., 1996, Receptor Specificity of the Fibroblast Growth Factor Family*, The Journal of Biological Chemistry, 271(25):15292-15297.
Ornitz et. al., 2001, Protein Family Review, Fibroblast Growth Factors, Genome Biology, 2(3):30051-300512.
Ornitz, 2000, FGFs, heparan sulfate and FGFRs: complex interactions essential for development, Bioessays, 22(2):108-112.
Patent Examination Report No. 1 for Australian Patent Application No. 2006292224, dated Oct. 4, 2011, 3 pages.
Patent Examination Report No. 2 for Australian Patent Application No. 2006292224, dated Jul. 3, 2013, 4 pages.
Pearson et. al., 1988, Improved tools for biological sequence comparison, Proc. Natl. Acad. Sci. USA, 85(8):2444-2448.
Pei et. al., 2002, Bioreactors Mediate the Effectiveness of Tissue Engineering Scaffolds, The FASEB Journal., 16:1691-1694.
Pei et. al., 2002, Growth Factors for Sequential Cellular De- and Re-differentiation in Tissue Engineering, Biochemical and Biophysical Research Communications, 294:149-154.
Pellegrini et. al., 2000, Crystal Structure of Fibroblast Growth Factor Receptor Ectodomain Bound to Ligand and Heparin, Nature, 407:1029-1034.
Pereboeva et. al., 2003, Approaches to Utilize Mesenchymal Progenitor Cells as Cellular Vehicles, Stem Cells, 21:389-404.
Peretti et. al., 1998, Bonding of Cartilage Matrices with Cultured Chondrocytes: An Experiential Model, Journal of Orthopedic Research, 16(1):89-95.
Peretti et. al., 1999, Biomechanical Analysis of a Chondrocyte-Based Repair Model of Articular Cartilage, Tissue Engineering, 5(4):317-326.
Peretti et. al., 2000, Cell-based Tissue-Engineered Allogeneic Implant for Cartilage Repair, Tissue Engineering, 6(5):567-576.

(56) References Cited

OTHER PUBLICATIONS

Peretti et. al., 2001, A Biomedical Analysis of an Engineered Cell-Scaffold Implant for Cartilage Repair, Annals of Plastic Surgery, 46(5):533-537.
Peretti et. al., 2003, Cell-Based Bonding of Articular Cartilage: An Extended Study, Journal of Biomedical Materials Research, 64A:517-524.
Peretti et. al., 2007, In Vitro Bonding of Pre-seeded Chondrocyte, Sport Sciences for Health 2(1):29-33.
Peterson et. al., 2000, Two- to 9-year Outcome After Autologous Chondrocyte Transplantation of the Knee, Clinical Orthopaedics and Related Research, 374:212-234.
Peterson et. al., 2002, Autologous Chondrocyte Transplantation: Biomechanics and Long-term Durability, American Journal of Sports Medicine, 30(1):2-12.
International Search Report for PCT/US02/09001 dated Mar. 27, 2003, (2 pages).
Itoh et. al., 2001, A Honeycomb Collagen Carrier for Cell Culture as a Tissue Engineering Scaffold, Artificial Organs, 25(3):213-217.
Itokazu et. al., 1997, The Sustained Release of Antibiotic from Freeze-Dried Fibrin Antibiotic Compound and Efficacies in a Rat Model of Osteomyelitis, Infection, 25(6):359-363.
Iwamoto et. al., 1991, Reduction in Basic Fibroblast Growth Factor Receptor is Coupled with Terminal Differentiation of Chondrocytes, J Biol Chem 266(1):461-467.
Jackson et. al., 2001, Cartilage Substitute: Overview of Basic Science & Treatment Options, Journal of American Academy of Orthopaedic Surgeons, 9:37-52.
Jacobi et. al., 2011, MACI—a new era?, Arthroscopy, Rehabilitation, Therapy & Technology, http://www.smarttjournal.com/content/3/1/10.
James et. al., 2000, Genetic manipulation of the rabbit heart via transgenesis, Circulation, 101:1715-1721.
Johnson et. al., 1993, Structural and Functional Diversity in the FGF Receptor Multigene Family, Advances in Cancer Research, 60:1-41.
Karlin et. al., 1990, Methods for assessing the statistical significance of molecular sequence features by using general scoring schemes, Proc. Natl. Acad. Sci. USA, 87:2264-2268.
Karlin et. al., 1993, Applications and statistics for multiple high-scoring segments in molecular sequences, Proc. Natl. Acad. Sci. USA, 90:5873-5877.
Kastrup et. al., 1997, X-ray Structure of the 154- Amino-Acid Form of Recombinant Human Basic Fibroblast Growth Factor Comparison with the Truncated 146-Amino-Acid Form, Acta Crystallographica, Section D53:160-168.
Kato et. al., 1990, Fibroblast Growth Factor is an Inhibitor of Chondrocyte Terminal Differentiation, Journal of Biological Chemistry, 265(10):5903-5909.
Keegan et. al., 1991, Isolation of an additional member of the fibroblast growth factor receptor family, FGFR-3, Proc. Natl. Acad. Sci. USA, 88:1095-1099.
Kiewitz et. al., 2000, Transcriptional regulation of S100A1 and expression during mouse heart development, Biochim Biophys Acta, 1498:207-19.
Kim et. al., 2002, Alternative type I and I? turn conformations in the ?8/?9 ?-hairpin of human acidic fibroblast growth factor, Protein Science, 11(3):459-66.
Kirikoshi, 2000, Molecular Cloning and Characterization of Human FGF-20 on Chromosome 8p. 21.3-p. 22, Biochemical and Biophysical Research Communications, 274(2):337-343.
Kirker et. al., 2002, Glycosaminoglycan Hydrogel Films as Biointeractive Dressings for Wound Healing, Biomaterials, 23:3661-3671.
Kondo et. al., 2005, Effects of Administration of Exogenous Growth Factors on Biomechanical Properties of the Elongation-Type Anterior Cruciate Ligament Injury With Partial Laceration, The American Journal of Sports Medicine, 33:188-196.
Kunkel, 1985, Rapid and efficient site-specific mutagenesis without phenotypic selection, Proc. Natl. Acad. Sci. USA, 82:488-492.
Kuroda et. al., 1999, Anabolic Effect of Amino terminally Truncated Fibroblast Growth Factor 4 (FGF4) on Bone, Bone, 25(4):431-437.
Kurokawa et. al., 2000, The Evi-1 oncoprotein inhibits c-Jun N-terminal kinase and prevents stress-induced cell death, EMBO J., 19:2958-2968.
Kuroyanagi et. al., 2001, Tissue-Engineered Product: Allogeneic Cultured Dermal Substitute Composed of Spongy Collagen with Fibroblasts, Artificial Organs, 25(3):180-186.
Lakso et. al., 1992, Targeted oncogene activation by site-specific recombination in transgenic mice, Proc. Nail. Acad. Sci. USA, 89:6232-6236.
LaPointe et. al., 1996, Tissue-specific expresson of the human brain natriuretic peptide gene in cardiac myocytes, Hypertension, 27:715-722.
Lev et. al., 1992, Dimerization and Activation of the Kit Receptor by Monovalent and Bivalent Binding of the Stem Cell Factor, The Journal of Biological Chemistry, 267, 15970-15977.
Li et. al., 2004, Synthesis and biological evaluation of a cross-linked hyaluronan-mitomycin C hydrogel, Biomacromolecules, 5(3):895-902.
Loeser et. al., 2005, Basic Fibroblast Growth Factor Inhibits the Anabolic Activity of Insulin-like Growth Factor 1 and Osteogenic Protein 1 in Adult Human Articular Chondrocytes, Arthritis & Rheumatism, 52(12):3910-3917.
Lorget et. al., 2012, Evaluation of the Therapeutic Potential of a CNP Analog in a Fgfr3 Mouse Model Recapitulating Achondroplasia, Am J Hum Genet., 91(6):1108-1114.
Lu et. al., 2006, Minced Cartilage without Cell Culture Serves as an Effective Intraoperative Cell Source for Cartilage Repair, Journal of Orthopaedic Research, 24:1261-1270.
Luo et. al., 1999, Synthesis and selective cytotoxicity of a hyaluronic acid-antitumor bioconjugate, Bioconjugate Chemicals, 10(5):755-763.
Madry et. al., 2003, Sustained transgene expression in cartilage defects in vivo after transplantation of articular chondrocytes modified by lipid-mediated gene transfer in a gel suspension delivery system, J Gene Med, 5(6):502-9.
Madry et. al., 2000, Efficient lipid-mediated gene transfer to articular chondrocytes, Gene Ther 7(4):286-91.
Madry et. al., 2002, Gene Transfer of a Human Insulin-like Growth Factor I cDNA Enhances Tissue Engineering of Cartilage, Human Gene Therapy, 13:1621-1630.
Madry et. al., 2003, Recombinant adeno-associated virus vectors efficiently and persistently transduce chondrocytes in normal and osteoarthritic human articular cartilage, Hum Gene Ther, 14(4):393-402.
Marian et. al., 1999, A transgenic rabbit model for human hypertrophic cardiomyopathy, J Clin Invest., 104:1683-1692.
Matsuda et. al., 1995, In Vivo Chondrogenesis in Collagen Sponge Sandwiched by Perichondrium, J Biomater Sci Polymer Ed, 7(3):221-229.
Mazue et. al., 1991, Preclinical and Clinical Studies with Recombinant Human Basic Fibroblast Growth Factor, Annals New York Academy of Sciences:329-340.
Mbawuike et. al., 1989, a murine alveolar macrophage cell line: morphological, cytochemical, and functional characteristics, J Leukoc Biol., 46:119-127.
McKercher et. al., 1996, Targeted disruption of the PU.1 gene results in multiple hematopoietic abnormalities, EMBO J., 15:5647-5658.
McLeskey et. al., 1994, MDA-MB-134 Breast Carcinoma Cells Overexpress Fibroblast Growth Factor (FGF) Receptors and are Growth-Inhibited by FGF Ligands, Cancer Research 54(2):523-530.
Messner et. al., 1996, Cartilage Repair: A Critical Review, Acta Orthopaedica Scandinavica, 67(5):523-529.
Abbate et. al., 2001, Biotechniques 3 1:336-40.
Abraham et. al., 1996, Human Basic Fibroblast Growth Factor: Nucleotide Sequence and Genomic Organization, EMBO Journal., 5(10):2523-2528.
Agrawal et. al., 1991, Pharmacokinetics, Biodistribution, and Stability of Oligodeoxynucleotide Phosphorothioates in Mice, PNAS, 88:7595-7599.

(56) References Cited

OTHER PUBLICATIONS

Altschul et. al., 1990, Basic Local Alignment Search Tool, J Mol Biol 215:403-410.
Andres et. al., 2008, A Pro-Inflammatory Signature Mediates FGF2-induced Angiogenesis, Journal of Cellular and Molecular Medicine, 13(8B):2083-2108.
U.S. Appl. No. 11/190,387, Advisory Action, Dec. 16, 2008 (16 pages).
U.S. Appl. No. 11/190,387, Advisory Action, Feb. 11, 2009 (7 pages).
U.S. Appl. No. 11/190,387, Advisory Action, Jan. 14, 2008 (3 pages).
U.S. Appl. No. 11/190,387, Advisory Action, Oct. 31, 2008 (15 pages).
U.S. Appl. No. 11/190,387, Final Rejection, Aug. 26, 2008 (12 pages).
U.S. Appl. No. 11/190,387, Final Rejection, Aug. 6, 2007 (18 pages).
U.S. Appl. No. 11/190,387, Non-Final Rejection, Mar. 27, 2007 (21 pages).
U.S. Appl. No. 11/190,387, Non-Final Rejection, Mar. 27, 2008 (11 pages).
U.S. Appl. No. 11/190,387, Requirement for Restriction/Election, Sep. 7, 2006 (7 pages).
U.S. Appl. No. 12/731,356, Non-Final Rejection, Mar. 29, 2011 (14 pages).
U.S. Appl. No. 12/731,356, Requirement for Restriction/Election, Dec. 23, 2010 (6 pages).
Arai et. al., 2000, Gene delivery to human chondrocytes by an adeno associated virus vector J Rheumatol 27(4):979-82.
Arai et. al., 2004, Effect of adenovirus-mediated overexpression of bovine ADAMTS-4 and human ADAMTS-5 in primary bovine articular chondrocyte pellet culture system Osteoarthritis Cartilage, 8:599-613.
Arakawa et. al., 1993, Production and Characterization of an Analog of Acidic Fibroblast Growth Factor With Enhanced Stability and Biological Activity, Protein Engineering, 6(5):541-546.
Aston et. al., 1986, Repair of Articular Surfaces by Allografts of Articular and Growth-Plate Cartilage, Journal of Bone and Joint Surgery, 68-B(1):29-35.
Attwood, 2000, The Babel of bioinformatics, Science, 290:471-473.
Aviezer et. al., 1994, Differential Structural Requirements of Heparin and Heparan Sulfate Proteoglycans That Promote Binding of Basic Fibroblast Growth Factor to Its Receptor, The Journal of Biological Chemistry, 269(1):114-121.
Aviles et. al., 2003, Testing clinical therapeutic angiogenesis using basic fibroblast growth factor (FGF-2), British Journal of Pharmacology, 140:637-646.
Bailly et. al., 2000, Uncoupling of Cell Proliferation and Differentiation Activities of Basic Fibroblast Growth Factor, FASEB Journal., 14:333-344.
Baird, 1994, Fibroblast growth factors: activities and significance of non-neurotrophin neurotrophic growth factors, Current Opinions in Neurobiology, 4:78-86.
Bange et. al., 2002, Cancer Progression and Tumor Cell Motility are Associated with the FGFR4 Arg 388 Allele, Cancer Research, 62:840-846.
Baragi et. al., 1995, Transplantation of transduced chondrocytes protects articular cartilage from interleukin 1-induced extracellular matrix degradation, J. Clin. Invest. 96(5):2454-60.
Barralet et. al., 2000, Dissolution of dense carbonate apatite subcutaneously implanted in Wistar rats, J Biomed Mater Res, 49(2):176-82.
Bartholomew et. al., 1997, The Evi-1 proto-oncogene encodes a transcriptional repressor activity associated with transformation, Oncogene, 14:569-577.
Behr et. al., 2010, Fgf-9 is required for angiogenesis and osteogenesis in long bone repair, PNAS, 107(26):11853-11858.

Bellosta et. al., 2001, Identification of Receptor and Heparin Binding Sites in Fibroblast Growth Factor 4 by Structure-Based Mutagenesis, Molecular and Cellular Biology 21(17):5946-5957.
Ben-Bassat et. al., 2000, in Biomaterials Engineering and Devices: Human Applications v2:I55-169.
Berclaz et. al., 2002, regulates alveolar macrophage Fc?R-mediated phagocytosis and the IL-18/IFN?-mediated molecular connection between innate and adaptive immunity in the lung, Blood, 100:4193-4200.
Beynnon et. al., 2005, Treatment of Anterior Cruciate Ligament Injuries Part 2, The American Journal of Sports Medicine, 33(11):1751-1767.
Beynnon, et. al., 2005, Treatment of Anterior Cruciate Ligament Injuries Part 1, The American Journal of Sports Medicine, 33(10):1579-1602.
Corpet, 1988, Multiple sequence alignment with hierarchical clustering, Nucleic Acids Res, 16(22):10881-90.
Coughlin et. al., 1988, Acidic and Basic Fibroblast Growth Factors Stimulate Tyrosine Kinase Activity in Vivo, Journal of Biological Chemistry, 263(2):988-993.
Coulson et. al., 1999, Collagen and a thermally reversible poloxamer deliver demineralized bone matrix (DBM) and biologically active proteins to sites of bone regeneration In: Portland Bone Symposium, Jeffrey O Hollinger: Proceedings from Portland Bone Symposium, Oregon Health Sciences University, US, 619-637.
Crameri et. al.,1997, Molecular evolution of an arsenate detoxification pathway by DNA shuffling, Nature Biotech, 15:436-438.
Cuenco et. al., 2001, Cooperation of BCR-ABL and AML1/MDS1/EVI1 in blocking myeloid differentiation and rapid induction of an acute myelogenous leukemia, Oncogene, 20:8236-8248.
Dahlberg et. al., 1991, Demineralized Allogeneic Bone Matrix for Cartilage Repair, Journal of Orthopaedic Research, 9:11-19.
Danilenko et. al., 1999, Recombinant rat fibroblast growth factor-16: structure and biological activity, Arch. Biochem. Biophys, 361:34-46.
De Jagereta et. al., 2003, Simultaneous detection of 15 human cytokines in a single sample of stimulated peripheral blood mononuclear cells, Clin & Diagn Lab Immunol, 10:133-139.
DeKoter et. al.,1998, EMBO 17:4456-4468.
Delezoide et. al., 1998, Spatio-temporal expression of FGFR 1, 2 and 3 genes during human embryo-fetal ossification, Mech Dev 77(1):19-30.
Dell' Accio et. al., 2001, Molecular markers predictive of the capacity of expanded human articular chondrocytes to form stable cartilage in vivo, Arthritis Rheum, 44(7):1608-19.
Dellow, et. al., 2001, Cardiovasc Res 50:3-6.
Deng et. al., 1996, Fibroblast Growth Factor Receptor 3 is a Negative Regulator of Bone Growth, Cell 84:911-921.
Denissen et. al., 1994, Bone Miner, 25:123-134.
Denissen, et. al., 2000, J Periodontol, 71:279-86.
Diduch et. al., 2002, Joint Repair: Treatment Options for Articular Cartilage Injury Orthopedic Technology Review, 4:24-27.
Dinser et. al., 2001, Comparison of long-term transgene expression after non-viral and adenoviral gene transfer into primary articular chondrocytes, Histochem Cell Biol, 116(I):69-77.
Dionne et. al., 1990, Cloning and expression of two distinct high-affinity receptors cross-reacting with acidic and basic fibroblast growth factors, The EMBO Journal, 9(9):2685-2692.
Doerks, 1998, Protein annotation: detective work for function prediction, Trends Genet., 14(6):248-250.
Dreyfus et. al., 1995, Expression of the Evi-1 gene in myelodysplastic syndromes, Leukemia, 9:203-205.
Dvorakova et. al., 2001, Changes in the Expression of FGFR3 in Patients With Chronic Myeloid Leukaemia Receiving Transplants of Allogeneic Peripheral Blood Stem Cells, British Journal of Haematology, 113:832-835.
Eliopoulos et. al., 2002, Human cytidine deaminase as an ex vivo drug selectable marker in gene-modified primary bone marrow stromal cells, Gene Ther, 9:452-462.
Elroy-Stein et. al., 1989, Cap-independent translation of mRNA conferred by encephalomyocarditis virus 5' sequence improves the performance of the vaccinia virus/bacteriophage T7 hybrid expression system, Proc. Natl. Acad. Sci., 86:6126-6130.

(56) References Cited

OTHER PUBLICATIONS

Eriksson et. al., 1991, Three-Dimensional structure of human basic fibroblast growth factor Proceedings of the National Academy of Science of USA, National Academy of Science, Washington, DC, US, 88:3441-3445.
Erlebacher et. al., 1995, Toward a Molecular Understanding of Skelet.al Development, Cell, 80:371-378.
European Search Report and Opinion for EP1119081.17 dated Feb. 14, 2012, 10 pages.
Evans et. al., 2004, Osteoarthritis gene therapy Gene Ther, 11(4):379-89.
Extended European Search Report for European Patent Application No. 06814983.0, dated Apr. 19, 2012, 7 pages.
Ezzat et. al., 2002, Targeted Expression of a Human Pituitary Tumor-Derived Isoform of FGF Receptor-4 Recapitulates Pituitary Tumorigenesis, The Journal of Clinical Investigation, 109:69-78.
F Lincoln Avery, Anterior Cruciate Ligament (ACL) Graft Options, http://wwworthoassociatescom/ACL_graftshtm, Internet. Article, The Sports Medicine Center, 1-15, Downloaded Jan. 9, 2007.
Faham et. al., 1998, Diversity Does Make a Difference: Fibroblast Growth Factor—Heparin Interactions, Current Opinion in Structural Biology, 8:578-586.
Faller et. al., 1984, Liposome encapsulation of retrovirus allows efficient superinfection of resistant cell lines, J Virol, 49(1):269-272.

\* cited by examiner

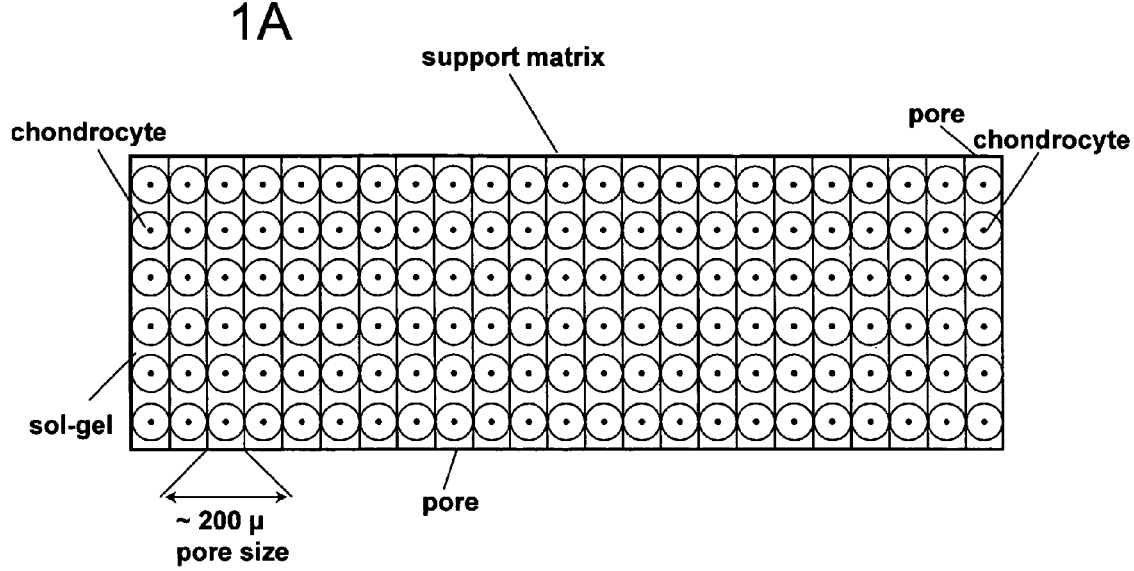
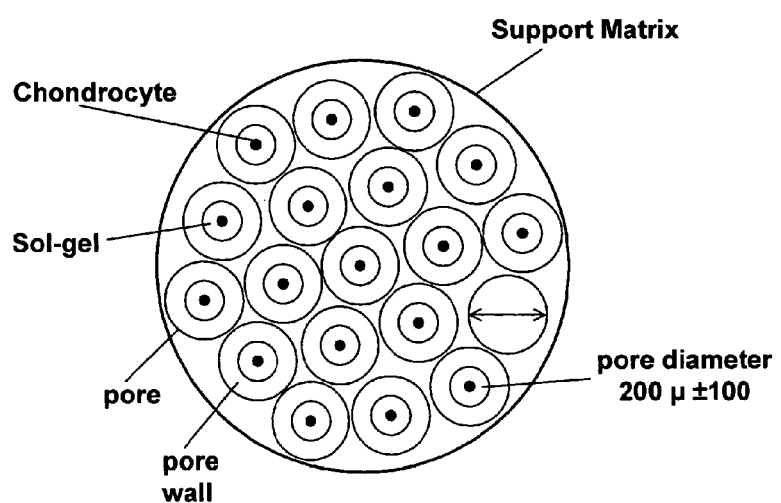
Fig. 1A-B

1C (Actual size)

1D
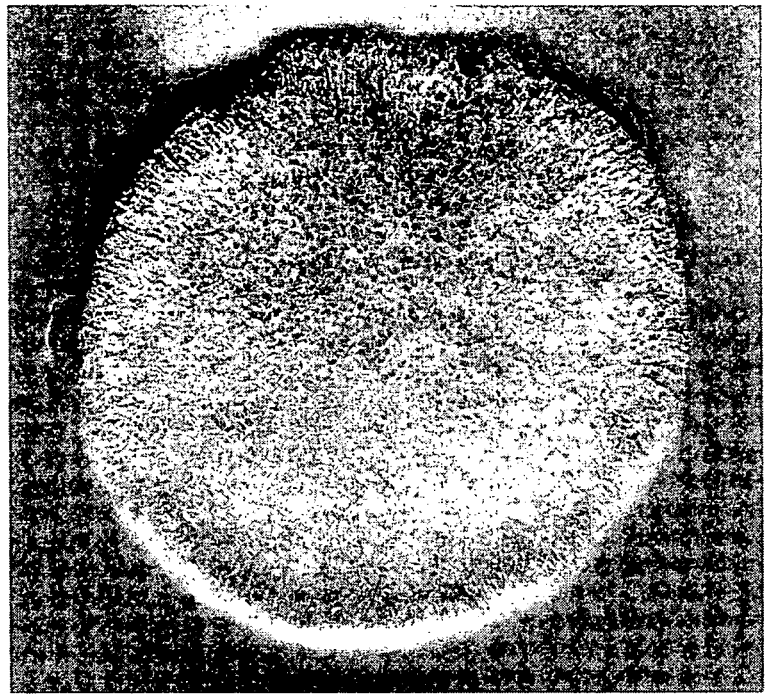
1E
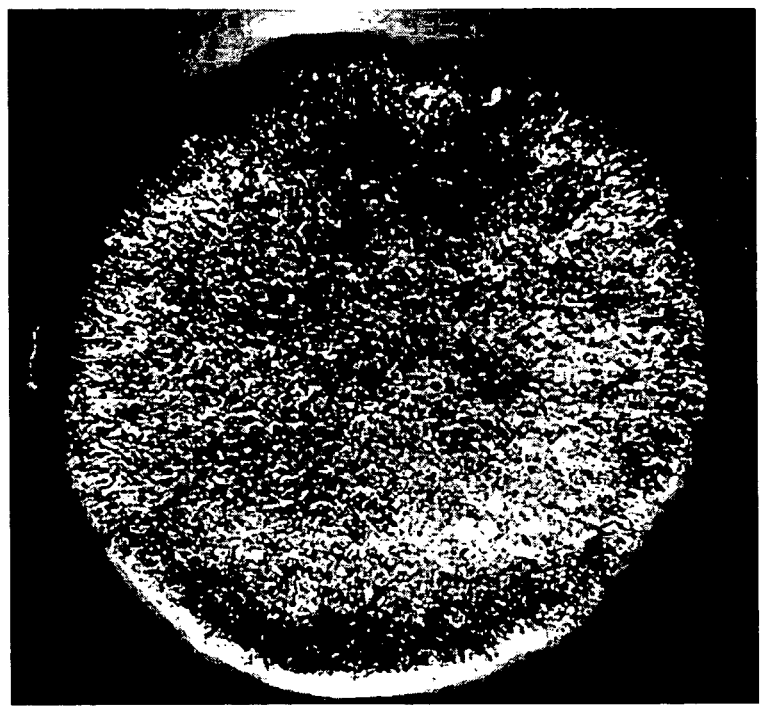
Fig. 1D-E

4mg/ml collagen, 5ml NH$_3$, pore size: 259±48

4mg/ml collagen, 6ml $NH_3$, pore size:
334±89

6mg/ml collagen, 2ml NH$_3$, pore size: 233±55

6mg/ml collagen, 4ml NH$_3$, pore size: 235±67

5mg/ml collagen, 1ml NH$_3$, in N$_2$ atmosphere (3 torr), pore size: 253±59

B

5mg/ml collagen, 1ml $NH_3$, in $N_2$ atmosphere (10 torr), pore size: 323±82

5mg/ml collagen, 3ml NH$_3$, in N$_2$ atmosphere (10 torr), pore size: 538±135

4mg/ml collagen, with surfactant (pore size: 198 ± 47) - surface

6mg/ml collagen, with surfactant (pore size: 256 ±59) - surface

8mg/ml collagen, with surfactant (pore size: 380 ±100) - surface

7A
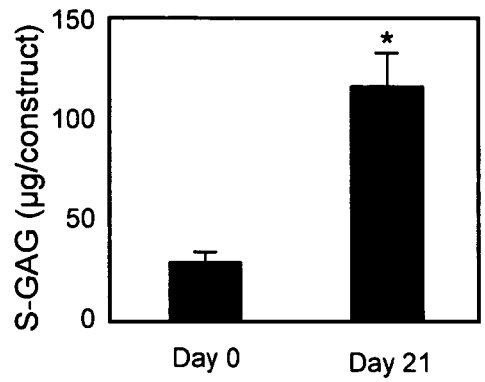
7B
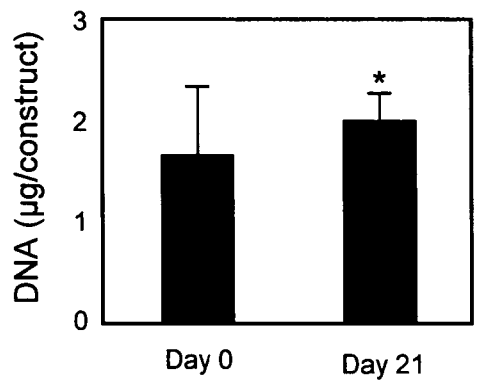
Fig. 7A-B

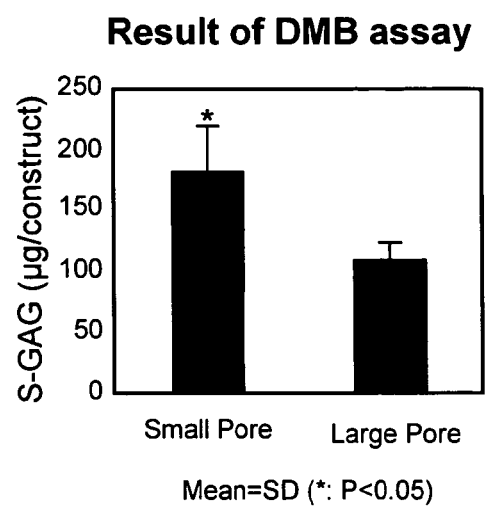
8A
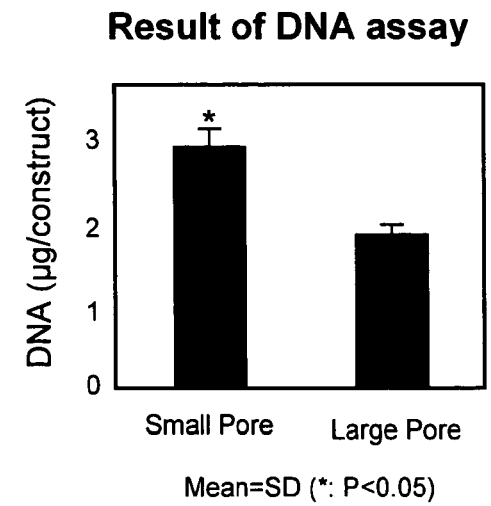
8B
Fig. 8A-B

CELL-SUPPORT MATRIX HAVING NARROWLY DEFINED UNIFORMLY VERTICALLY AND NON-RANDOMLY ORGANIZED POROSITY AND PORE DENSITY AND A METHOD FOR PREPARATION THEREOF

This application is a continuation of U.S. patent application Ser. No. 11/523,833, filed Sep. 19, 2006, now U.S. Pat. No. 8,921,109, which is based on and claims priority of the provisional application Ser. No. 60/718,714 filed on Sep. 19, 2005.

BACKGROUND OF THE INVENTION

Field of Invention

The current invention concerns a biocompatible cell-support matrix having narrowly defined and uniformly vertically and non-randomly organized porosity and a pore density and a method for preparation thereof. In particular, the invention concerns a biocompatible cell-support matrix or support substrate having substantially the same size pores said matrix or substrate providing a support structure for live-cell suspension. The matrix has vertically non-randomly oriented open pores of substantially homogeneous pore size and narrowly defined diameter.

The support matrix seeded with the chondrocyte suspension is suitable for initiation of growth and de novo formation of hyaline or hyaline-like cartilage in vitro and in vivo as well as for preparation of cellular or acellular implants for implantation into articular cartilage in situ.

The invention additionally concerns a collagen-matrix composite system comprising of said support matrix seeded with chondrocyte suspension, said system being capable of induction of hyaline or hyaline-like cartilage from chondrocytes in vitro or in vivo when introduced into the articular cartilage in situ.

BACKGROUND AND RELATED DISCLOSURES

Collagen matrices for use as an implant for repair of cartilage defects and injuries are known in the art. Of particular interest is a honeycomb structure developed by Koken Company, Ltd., Tokyo, Japan, under the trade name Honeycomb Sponge, described in the Japanese patent JP3170693. Other patents related to the current subject disclose collagen-based substrate for tissue engineering (U.S. Pat. No. 6,790,454) collagen/polysaccharide bilayer matrix (U.S. Pat. No. 6,773,723), collagen/polysaccharide bilayer matrix (U.S. Pat. No. 6,896,904), matrix for tissue engineering formed of hyaluronic acid and hydrolyzed collagen (U.S. Pat. No. 6,737,072), method for making a porous matrix particle (U.S. Pat. No. 5,629,191) method for making porous biodegradable polymers (U.S. Pat. No. 6,673,286), process for growing tissue in a macroporous polymer scaffold (U.S. Pat. No. 6,875,442), method for preserving porosity in porous materials (U.S. Pat. No. 4,522,753), method for preparation of collagen-glycosaminoglycan composite materials (U.S. Pat. No. 4,448,718), procedures for preparing composite materials from collagen and glycosaminoglycan (U.S. Pat. No. 4,350,629) and a crosslinked collagen-mucopolysaccharide composite materials (U.S. Pat. No. 4,280,954).

However, many of the above disclosed structures have uncontrolled parameters such as uneven and uncontrolled porosity, uneven density of pores, uneven sizes of the pores and random distribution of pores within the support matrix. Such uncontrolled parameters lead to structures that are sterically unstable to provide support for cartilage matrix producing cells as these structures easily collapse upon contact with a solution or suspension containing cartilage producing cells.

There is, therefore, a need for a more uniform and sterically stable support matrix preferably prepared from a biocompatible material, such as collagen, wherein said matrix has narrowly defined size and density of pores and the pores are uniformly distributed, vertically oriented and non-randomly organized.

It is, therefore, a primary object of this invention to provide a sterically stable biocompatible, preferably collagen based matrix, having properties enabling chondrocyte attachment in numbers needed for induction and formation of hyaline or hyaline-like cartilage.

The current invention provides such matrix and/or a method for fabrication thereof by providing a sterically stable and biocompatible matrix, preferably made of Type I collagen, having narrowly defined pore sizes and density with said pores organized vertically wherein said matrix permits seeding and attachment of chondrocytes suspended in collagen, gel, sol-gel or hydrogel that gels at the body temperature, in sufficiently high numbers to induce formation of new hyaline or hyaline-like cartilage. The matrix according to the invention has a substantially narrowly defined pore size in diameter and pore density in vertically organized manner that creates an apical (top or synovial) or basal (bottom or bone) surface to the implant where the sizes and diameters of the pores on both the apical or basal surface are substantially the same. The gel system according to the invention provides conditions for a sterically-enhanced enablement of chondrocytes to produce extracellular matrix comprising glycosaminoglycan and Type II collagen and its deposition within said matrix in ratios characteristic for normal healthy articular hyaline cartilage.

All patents, patent applications and publications cited herein are hereby incorporated by reference.

SUMMARY

One aspect of the current invention is a biocompatible support matrix having narrowly defined uniformly and vertically and non-randomly organized porosity and a pore density and a method for preparation thereof.

Another aspect of the current invention is a collagen-based support matrix having narrowly defined uniformly and vertically and non-randomly organized porosity and a pore density and a method for preparation thereof.

Another aspect of the current invention is a Type I collagen-based support matrix suitable for seeding with chondrocytes suspension, said matrix having vertically oriented open pores of substantially homogeneous pore size of narrowly defined diameter of about 200±100 μm.

Still another aspect of the current invention is the support matrix suitable for growth and de novo formation of a hyaline-like cartilage in vitro and for preparation of cellular or acellular implants for in situ implantation in vivo.

Yet another aspect of the current invention is a collagen-matrix composite system comprising a Type I collagen matrix and a suspension of chondrocytes seeded into said matrix wherein said system is capable of induction of hyaline or hyaline-like cartilage from chondrocytes in vitro or in vivo when said matrix is implanted with or without cells in situ.

Another aspect of the current invention is a method for preparation of an uniform and sterically stable support matrix prepared from a biocompatible collagen material wherein said matrix has narrowly defined porosity and uniformly distributed vertically oriented and non-randomly organized pores of substantially the same size in diameter.

Still yet another aspect of the current invention is a method for preparation of a sterically stable colagen-based matrix having properties, such as a pore size of about 200±100 μm in diameter, density of about 25±10/mm², and uniform pore distribution enabling chondrocyte attachment in numbers needed for induction of formation of hyaline or hyaline-like cartilage.

Still yet another aspect of the current invention is a method for fabrication of a sterically stable type I collagen-based matrix that permits seeding of chondrocytes suspended in a Type-I collagen or in a synthetic sol-gel that gels at the body temperature, wherein said matrix has a substantially narrowly defined pore size of about 200±100 μm and a pore density 25±10/mm² in a vertically organized manner that assures that pores at a top (apical) and bottom (basal) surface of the implant have substantially the same size.

Yet another aspect of the current invention is collagen, gel, sol-gel or hydrogel comprising a system that provides conditions for a sterically-enhanced induction of chondrocytes into said matrix enabling said chondrocytes to produce extracellular matrix comprising glycosaminoglycan and Type II collagen and its deposition within said matrix in the ratios characteristic for normal healthy articular hyaline cartilage.

Yet another aspect of the current invention is a method for producing a Type I collagen-based matrix for seeding chondrocytes wherein said method comprises preparation of said matrix from collagen suspension of defined collagen amount in the presence of ammonia, surfactant, at reduced pressure or in inert atmosphere or any combination of all these parameters.

Still another aspect of the current invention is a gel-matrix composite system capable of inducing cartilage production comprising a collagen-based matrix seeded with a suspension of chondrocytes in collagen or a sol-gel polymer able to gel at a body temperature.

BRIEF DESCRIPTION OF FIGURES

FIG. 1A is a schematic side view of the collagen-based matrix having a substantially homogeneous pore size of about 200±100 μm and narrowly defined porosity with chondrocytes shown as if seeded in matrix pores in a substantially same distribution pattern within the matrix.

FIG. 1B is a schematic top view of a collagen-based matrix showing a distribution of as if seeded chondrocytes within the collagen-based matrix to be substantially homogeneous within the pores having a defined diameter of about 200±100 μm.

FIG. 1D is a photograph of approximately 2.5× magnified actual Type I collagen matrix showing pore distribution within the matrix.

FIG. 1E is photograph of approximately 2.5× magnified actual Type I collagen matrix with darkened background for better contrast showing pore distribution within the matrix.

FIG. 7A is a graph showing results of determination of a content of S-GAG, measured by DMB assay, at day zero and day 21, obtained with seeding chondrocytes into the matrix having 200±50 pore sizes. FIG. 7B is a graph showing a content of DNA measured by DNA assay at day zero and day 21.

FIG. 8A is a graph showing a content of S-GAG produced by chondrocytes seeded in the support matrix having small pores (153±39 μm) or large pores (435±60 μm). FIG. 8B is a graph showing a content of DNA in the small and large pores, measured by DNA assay at day zero and day 21.

DEFINITIONS

Figure 1C:
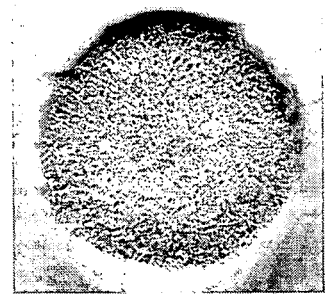
FIG. 1C is a photograph of the actual Type I collagen matrix produced according to the method of the invention without magnification.

"Sterically stable supporting structure" means non-random vertical orientation of collagen-fibrillar structure.

"Sterically unstable supporting structure" means random orientation mesh-like collagen-fibrillar structure.

"The matrix porosity" means a pore size defined by the diameter of holes within the support matrix or substrate as well as density of the pore distribution as a function of cross-sectional area in millimeters.

"Substantially homogeneous" means at least 85-99% homogeneity, that is at least 85% of all pores have sizes within the given range of 200±100 μm. Preferable homogeneity is between 95 and 99%.

"Substantially homogeneous porosity" means that a pore size and diameter is within pore size range of about 200±100 μm, preferably 200±50 μm, in diameter.

"Top surface" means an apical or synovial side of the matrix turned toward the joint.

"Bottom surface" means basal, closest to bone surface of the matrix.

"Chondrocytes" means the cells naturally residing in articular cartilage.

"About 200±100 μm" means and is intended to include also pores where the mean average is within additional 10-20 μm on the upper side.

"S-GAG" means sulfated glycosaminoglycan.

DETAILED DESCRIPTION OF THE INVENTION

The current invention is directed to a collagen-based matrix of defined porosity having substantially homogeneous pore sizes as well as to a method for preparation thereof. The collagen-based matrix prepared according to the method of the invention has uniformly defined vertically non-randomly organized porosity and a defined pore density.

The support matrix or substrate is generally prepared from a biocompatible material such as collagen, particularly Type I collagen, and has vertically non-randomly oriented open pores of substantially homogeneous pore size of a narrowly defined diameter. The matrix is suitable for preparation of acellular implants or cellular implants seeded with chondrocytes, as well as for growth and de novo formation of hyaline or hyaline-like cartilage in vitro and in vivo.

The invention additionally concerns a collagen-matrix composite system comprising said matrix seeded with a suspension of chondrocytes in collagen, gel, sol-gel or thermoreversible hydrogel, said system being capable of enabling formation of hyaline or hyaline-like cartilage by supporting said chondrocytes in vitro or in vivo when said system is implanted into damaged or injured cartilage in situ to produce extracellular matrix and its components Type II collagen and S-GAG.

The Type I collagen-based matrix of the invention has substantially homogeneous pore size range of about 200±100 μm, preferably about 200±50 μm, in diameter. This pore size has been shown to provide the largest attachment of the chondrocytes to the pores of the matrix.

The support matrix is ultimately useful for treatment of articular cartilage injuries and lesion by providing means for growing a new hyaline or hyaline-like cartilage for treatment, replacement or regeneration of the damaged or injured articular cartilage. Such treatment is currently difficult because of the unique properties of the articular cartilage that is not the same as and does not behave as other soft tissues.

I. Articular Cartilage

Articular cartilage covers the ends of bones in synovial joints. Articular cartilage is an unique tissue in that is it is avascular, aneural and alymphatic and in mature state contains a very small number of cells. These properties are the main reason why articular cartilage has such a poor intrinsic capacity to heal (Install, J. N. and Scott, W. N., *Surgery of the Knee*, 3$^{rd}$ Edition, p. 341 (2001).

Articular cartilage is known as a relatively acellular tissue whose extracellular space is occupied by interstitial fluid (60-80%) and organic extracellular matrix (ECM) components, primarily proteoglycans and collagens.

Immature chondrocytes are the articular cartilage cells that are present in large numbers in cartilage of young individuals. The immature chondrocytes are metabolically active cells that are responsible for growth of cartilage in the young individuals. In adult individuals, where the growth of the bones has stopped, cartilage contains mature chondrocytes that are limited in number in mature quiescent cartilage and those present are mainly metabolically inactive.

The mechanical function of articular cartilage is determined by its high water content and by the particular architecture of the collagen network. This network consists of cross-linked fibrils that extend perpendicular from the subchondral bone and curve gradually to a course parallel to the articular surface in the superficial zone ("Form and Bau der Gelenkknorpel in ihren Beziehungen zur Funktion", *Z. Zellforsch.*, Vol. 2, pp. 783-862 (1925)).

Any replacement support structure should thus have orientation and organization similar to that observed naturally. Consequently, a vertical orientation of a porous structure, preferably one made of a biodegradable material used in lieu of the cartilage matrix, would seem to be an important aspect for a cartilage regeneration in vivo due to the similar structure of the native articular cartilage. Consequently, a combination of the vertical porous structure providing the necessary support combined with chondrocytes suspended in collagen, gel, sol-gel or another hydrogel would likewise seem to be beneficial for cartilage treatment in vivo or regeneration of cartilage in vitro because collagen, gel, sol-gel or another hydrogel in which the chondrocytes are suspended are biodegradable materials native or biocompatible with articular cartilage and therefore can maintain chondrocytic phenotype and stimulate cartilage extracellular matrix synthesis in vitro or in in vivo when the support matrix seeded with chondrocytes is implanted in situ.

II. Collagen-Based Matrix and a Method for Preparation Thereof

The collagen-based matrix of the invention is an essential component of a gel-matrix composite system capable of initiating the induction of hyaline-like cartilage from chondrocytes.

A. Design of the Matrix

The matrix of the invention has been designed to meet requirements of properties needed for the support matrix.

The first requirement is that the support matrix is prepared from the biocompatible and preferably biodegradable materials that are the same or similar to those observed in the articular cartilage.

The second requirement is that the support matrix has a spatial organization and orientation similar to that of the articular cartilage.

The third requirement is that the support matrix has a porosity permitting the seeding of the chondrocytes into said matrix in a number of cells that are sufficient for initiation of a formation of new hyaline or hyaline-like articular cartilage in vitro and/or in vivo.

The fourth requirement is that the support matrix has sufficient number of pores for the number of cells needed for initiation of articular cartilage formation and that the pore sizes are such that the majority of chondrocytes seeded into said support matrix are suspended within the support matrix in numbers that would result in formation of new hyaline or hyaline-like cartilage.

The fifth requirement is that the pores have substantially the same size in a range from about 200±100 μm, preferably between about 200±50 μm in pore diameter and that such size is substantially the same from the top apical to the bottom basal surface of the pores, said pores being organized vertically from the top to the bottom.

B. Support Matrix

Typically, the support matrix, preferably the collagen-based support matrix, of the invention is a three-dimensional structure made of a biocompatible and/or biodegradable material of defined density and porosity.

Typically, the support matrix is prepared from a collagenous gel or gel solution containing Type I collagen, Type II collagen, Type IV collagen, gelatin, agarose, hyaluronin, a cell-contracted collagen containing proteoglycan, glycosaminoglycan or glycoprotein, fibronectin, laminin, a bioactive peptide growth factor, cytokine, elastin, fibrin, a synthetic polymeric fiber made of a poly-acid such as polylactic, polyglycolic or polyamino acid, polycaprolactone, polyamino acid, polypeptide gel, copolymers thereof, each alone or in a combination. Additionally, the support matrix may be prepared from the collagen precursors. For example, the collagen precursors may be used to reconstitute collagen fibrillar structure for matrix protection. These precursors are, for example peptide monomers, such as alpha 1 (type I), and alpha 2 (type I) collagen peptide or alpha 1 (type I) alpha 2 (type I) peptides, in combination, or 2 (alpha 1, type I) and 1 (alpha 2, type I) peptides.

Preferably, the support matrix of the invention is prepared from collagen and most preferably from Type I collagen, containing a plurality of narrowly defined uniformly vertically and non-randomly organized pores. The pores have substantially homogeneous narrowly defined size and diameter and are uniformly distributed through the matrix dividing the matrix space into a fluid-filled column or network.

In preferred embodiments the Type I collagen-based matrix is a collagen-based sponge-like structure or honeycomb-like lattice of defined porosity having a vertically organized pores of substantially same sizes.

a. Defined Porosity

The support matrix of the invention has a certain thickness and vertically organized pores of a defined diameter oriented to create an apical (top or synovial) or basal (bottom or bone) surface of the matrix for implantation. The diameter of said pores is chosen such that the matrix in conjunction with the chondrocyte-containing gel, preferably a sol-gel, facilitates a sterically-enhanced induction of extracellular matrix glycosaminoglycan and type II collagen deposition in ratios characteristic of hyaline articular cartilage.

b. Pore Sizes

The vertically oriented cellular or acellular support matrix made of the biocompatible material having a predetermined pore size filled with chondrocytes suspension is important aspect of the quality of the repair tissue in vivo and for production of the articular cartilage in vitro.

Consequently, it is important to determine the optimal pore size for the porous matrix because the size of the pores of the matrix affects the chondrocyte attachment to the matrix walls and assures the presence of chondrocytes within the matrix needed for cartilage regeneration in vitro and in vivo. Sizes of the pores are substantially homogeneous with homogeneity above 85%, preferably 95%, most preferably about 98-99% of pores having a diameter size of about 200±100 µm, preferably 200±50 µm.

The pores of the collagen-based matrix are homogeneously distributed within said matrix to form a sponge-like structure able to taking in and evenly distributing the chondrocytes suspended in a gel solution and providing conditions conducive to producing extracellular matrix by the suspended chondrocytes.

The defined and substantially homogeneous pore size diameter of the collagen-based matrix is an important aspect of the invention. Collagen-based matrices of defined pore sizes according to the invention having different pore size diameter permit faster or slower infiltration of the chondrocytes into said matrix, faster or slower growth and propagation of the cells and, ultimately, the higher or lower density of the cells in gel-matrix system. Such pore size may be adjusted by varying the pH of the gel solution, collagen concentration, lyophilization conditions, temperature, degree of cross-linking of collagen, etc.

Generally, in the prior art structures, the pore sizes are not defined and not limited to one substantially homogeneous size. the collagen-based matrices known in the prior art are mostly structures containing pores having mixed pore sizes of from about 50 to about 2000 µm.

The support matrix of the invention has the spatial organization and orientation similar to that of the articular cartilage. The spatial organization and orientation of support matrix is schematically depicted in FIGS. 1A and 1B.

FIG. 1A is a schematic side view of the support matrix showing the vertical organization and orientation of support matrix pores seeded hypothetically with chondrocytes suspended in sol-gel.

As seen in FIG. 1A, the pores are of substantially the same size in diameter and the number of cells in each pore is also substantially the same. The cells shown here are round and touching the walls of the pores illustrating the attachment requirement for the support matrix.

Suspending solution for chondrocytes is any gel solution, preferably one containing collagen, gel, sol-gel or thermoreversible hydrogel that can change its state from sol to gel depending on the temperature.

FIG. 1B is a schematic top view, showing hypothetically the ideally homogeneous distribution of pores through the support matrix, where the pores have the same sizes and chondrocytes are evenly distributed within the pores. The pores walls that separate individual pores are also seen.

FIG. 1B is a schematic top view of a gel-matrix composite system comprising the collagen-based matrix component made of Type I collagen and embedded with chondrocytes suspended in a sol-gel showing a distribution of chondrocytes within said collagen-based matrix to be substantially homogeneous within the pores having a defined diameter of about 200 µm. The outer circle defines a size of the whole matrix wafer. Smaller circles are pores having a substantially the same size. Inside of the pore circles are chondrocytes deposited there in a sol-gel solution.

FIG. 1C is the photograph of the actual Type I collagen matrix produced according to the method of the invention without magnification. The matrix pores are visible as a black dots. The matrix can be cut to order in both directions to obtain a perfect fit, if used, for example, for an articular cartilage implant.

FIG. 1D is the photograph of 4× magnified actual Type I collagen matrix showing the pore distribution within the matrix.

FIG. 1E is photograph of approximately 4× magnified actual Type I collagen matrix with darkened background for better contrast showing the pore distribution within the matrix.

Chondrocytes suspended in a collagen, gel, sol-gel or thermoreversible hydrogel solution are introduced into narrowly defined pores of a substantially the same size and distribution within the matrix. Vertically separated columns have substantially the same diameter and defined sizes of the pores. The pores are filled with the chondrocyte suspension.

This arrangement provides sterically advantageous conditions for homogeneous distribution of chondrocyte deposition within the pores that lead to enhanced production of proteoglycans and type II collagen in ratios corresponding to the ratios observed for these compounds in the healthy hyaline cartilage.

The structural macromolecules and cartilage account for 20 to 30% of the wet weight of cartilage and includes type II collagen, large aggregating proteoglycans and non-collagenous proteins or glycoproteins. With maturation, collagen contributes over 50% and proteoglycans contribute 30-35% of the matrix dry weight.

The matrix is typically prepared as a composite cylindrical wafer seen in FIGS. 1C-1E or as a rectangular block structure cut into a wafer-like matrix construct having from about 4 mm to about 25 mm in diameter and thickness of from 0.5 to about 5 mm. The seeding density of this construct is about 25,000-300,000 chondrocytes per 25 μl of collagen solution corresponding to about 1-12 millions cells/mL. The above density numbers are exemplary only and even lesser seeding density is possible and has been shown to lead to the production of the hyaline or hyaline-like cartilage. The cell density range for seeding is preferably from about 1 to about 30 million/mL. Chondrocytes are preferably suspended in a type I or Type II collagen or in a synthetic gel, sol-gel or hydrogel and such suspension, in combination with the support matrix, forms a gel-matrix composite system of the invention.

C. Preparation of the Support Matrix

The current invention additionally concerns a novel method for preparation of the support matrix that meets the requirements stated in section IIA.

The method for preparation of the support matrix meeting such criteria involves process for standardizing the pore size, vertical orientation and organization, homogeneity and uniformity of the collagen-based matrix of the invention.

The fabrication method for preparation of the current support matrix is based on investigation of various parameters comprising the biocompatible components and/or additives and their amounts, or reaction conditions, such as, for example, pH, temperature, pressure, reduced pressure, presence of inert gasses and an apparatus for testing these parameters all alone or in various combinations.

1. Apparatus for Preparation of the Support Matrix

Fabrication set-up for preparation of the support matrix of the invention comprises variable components depending on the conditions selected for the processing.

It typically comprises a sealed container containing the biocompatible material or a precursor thereof, preferably Type I collagen, selected for the preparation of the support matrix wherein said material may be subjected to various conditions for testing and optimization or for final preparation of the support matrix. Added features may contain means for increasing or decreasing pressure, temperature, adjusting pH, adding other components, pumps, gas tanks, valves, etc.

Figure 2:
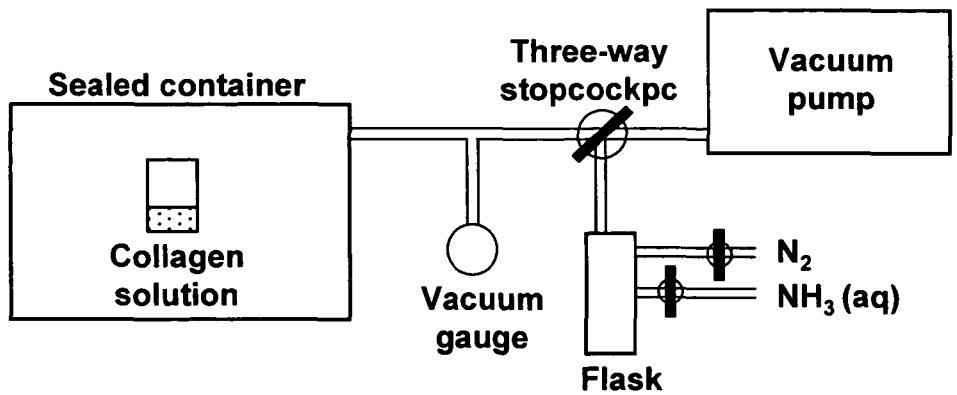
FIG. 2 is a scheme of an experimental set-up for preparation of a support matrix of the invention, providing means for storing and introduction of aqueous ammonia, introduction of inert atmosphere and creating reduced pressure.

One illustrative set-up for preparation of the support matrix is shown in FIG. 2.

FIG. 2 is schematic representation of one experimental set-up used for preparation of a support matrix of the invention, providing means for introduction of aqueous ammonia, means for reducing pressure and means for providing an inert atmosphere. Typically, the starting material, in this case the collagen solution, is placed into a sealed container having an outlet connected to a vacuum gauge that is further connected to a vacuum pump and a source of an inert gas. In FIG. 2, two sources are shown for supplying the aqueous ammonia and for storing nitrogen with a means for introducing nitrogen into the system. The starting material is then subjected to ammonia vapors by introducing a predetermined amount of aqueous ammonia into said container, and/or further introducing the inert gas, such as nitrogen or argon, or in one alternative, air, and optionally performing the reaction under reduced pressure, in the presence of a surfactant or under other reaction conditions. All these may be performed and/or tested in any combination to achieve the optimal expected results.

2. Method for Preparation of the Support Matrix

The selected criteria for the pore size of the support matrix were set to prepare the support matrix having substantially homogeneous population of pores within said matrix wherein said pores have substantially the same size in diameter of about 200±100 μm.

The preliminary studies determined that these parameters may be best met with utilizing the Type I collagen in concentrations from about 2 to about 10 mg/ml of collagen in solution, and these solutions were, therefore, further investigated for optimization of conditions for preparation of the support matrix meeting the above set criteria.

The process for optimization of conditions for preparation of the support matrix meeting these criteria involved testing of Type I collagen in 2, 4, 6, 8, and 10 mg per ml of solution, and its polymerization in the presence of 3% aqueous ammonia added in 1, 2, 3, 4, 5, and 6 ml volume. The same collagen preparations were tested with added non-ionic surfactant (Pluronic® F86, 0.3 weight/%), and the same collagen solutions were polymerized in an inert atmosphere and under reduced pressure. Various combinations of the above conditions were further tested to obtain the support matrix with the smallest and most homogeneous pore sizes.

Results are summarized in Tables 1-3 and in representative FIGS. 3-6.

a. Effect of the Ammonia Presence on Pore Sizes

In one embodiment, the support matrix was prepared from bovine Type I atelocollagen (2.9 mg/ml, pH 2.1), obtained from Inamed Corporation, Fremont, Calif. The collagen was concentrated by a precipitation followed by centrifugation and then dissolved in aqueous HCl in order to reach the desired concentration. The procedure for preparation of the support matrix in the presence of ammonia is described in Example 3.

The pore sizes of the support matrix obtained under these conditions are expressed as a function of collagen concentration and volume of ammonia solution/concentration, is seen in Table 1.

TABLE 1

| Collagen conc. | Volume of 3% aqueous ammonia | | | | |
|---|---|---|---|---|---|
| | 2 ml | 3 ml | 4 ml | 5 ml | 6 ml |
| 2.8-2.9 mg/ml | — | — | No pores | — | No Pores |
| 4 mg/ml | — | 256 ± 68 | 274 ± 87 | 259 ± 48* | 334 ± 89 |
| 6 mg/ml | 233 ± 55 | 365 ± 107 | 235 ± 67* | — | — |
| 8 mg/ml | 284 ± 90* | 299 ± 73 | 1195 ± 294 | — | — |
| 10 mg/ml | 474 ± 108* | — | Few pores | — | — |

Pore size was measured within 1 mm of the surface of the formed matrix.

As seen in the Table 1, polymerization of collagen solution containing between 2.8 and 2.9 mg/ml did not result in a porous matrix formation regardless how much ammonia was added. Collagen at 4 mg/ml and at 3 ml or 5 ml ammonia polymerized into the matrix having a preferred and/or acceptable pore sizes in the range of 256±68 µm and 259±48 µm, respectively. At 6 ml of ammonia, the matrix formed with pore sizes in the range of 334±89 µm.

Figure 3A:
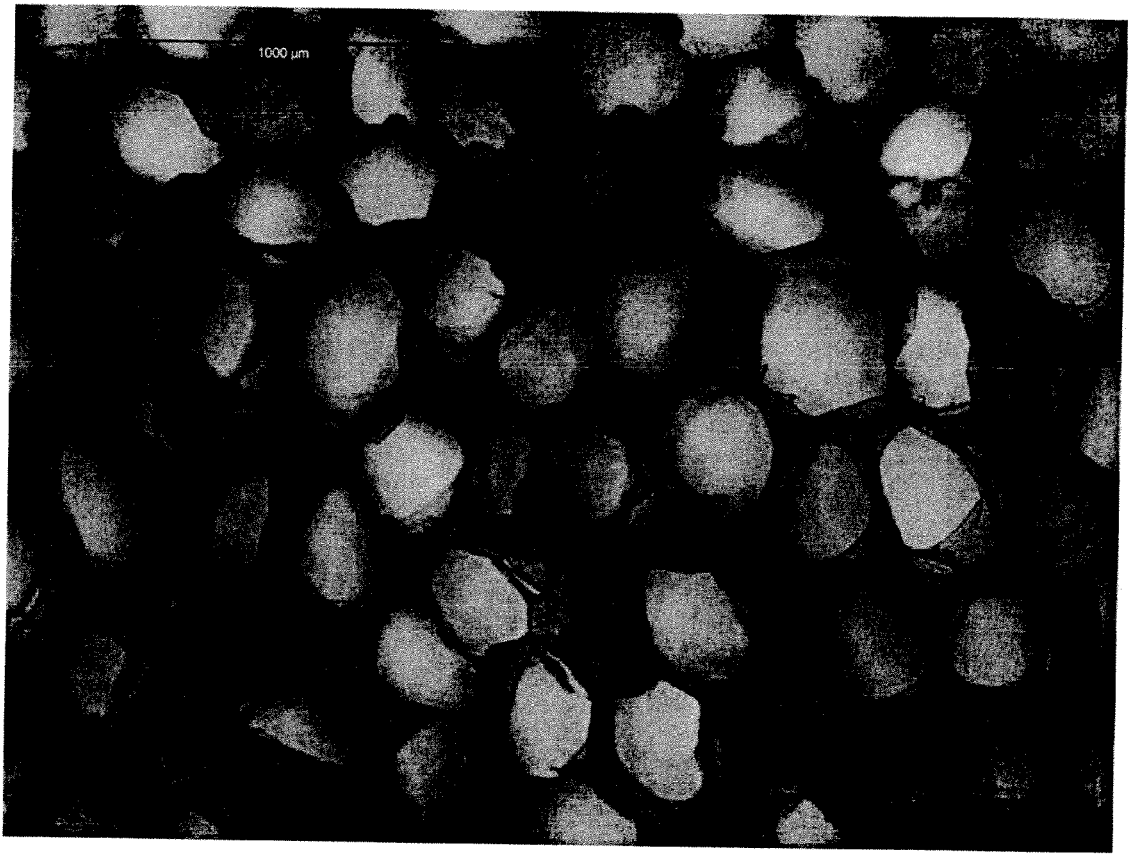
FIG. 3A is a microphotograph of a Type I collagen-based matrix prepared from 4 mg/ml of collagen in the presence of 5 ml of 3% ammonia, showing the pore size about 259±48 μm. The FIG. 3A clearly shows that the matrix has pores of substantially the same size and an equal distribution throughout the matrix. When the ammonia volume was increased to 6 ml, the pore size increased to 334±89 μm, as seen in FIG. 3B. Scale (1000 μm, i.e. 1 cm) is shown in upper left corner.
Figure 3B:
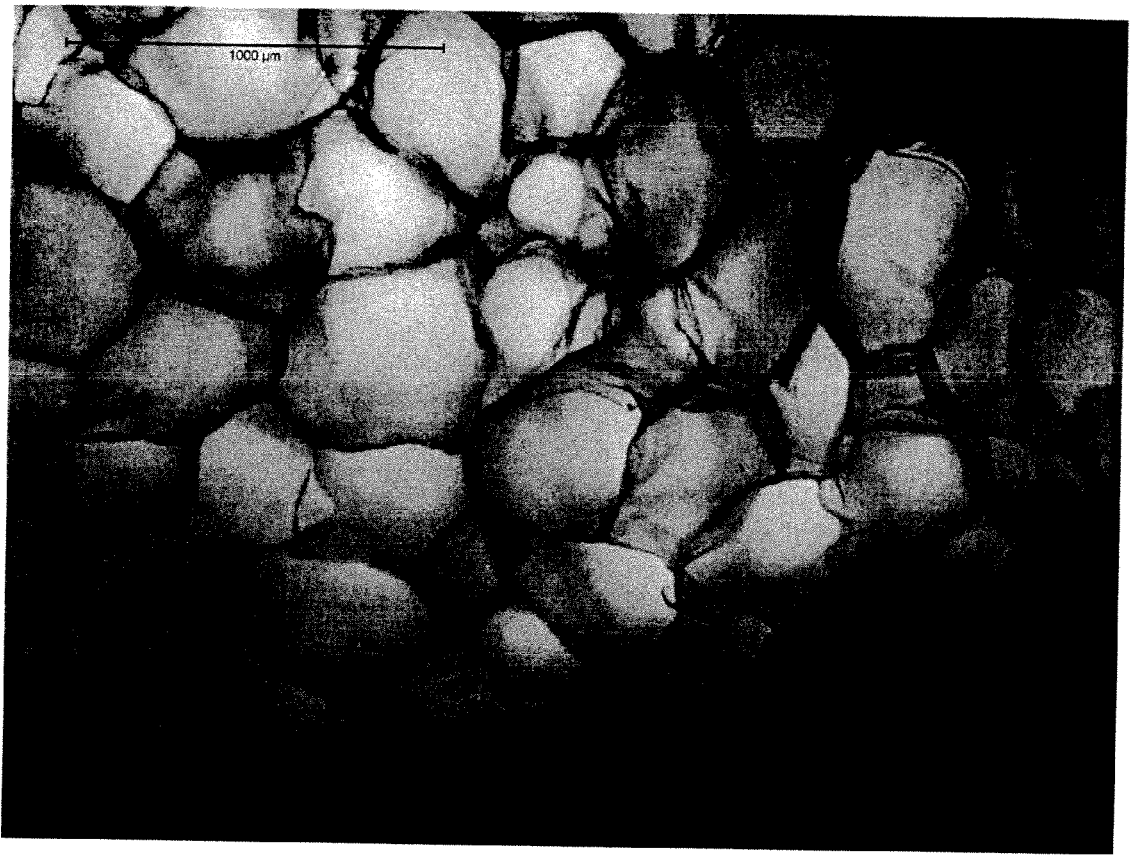

FIG. 3A and FIG. 3B are representative microphotographs of support matrices prepared from 4 mg/ml collagen in the presence of 5 or 6 ml of ammonia resulting in pore sizes ranges of about 259±48 µm and about 334±89 µm, respectively. Both microphotographs are on the same scale (scale 1000 µm) and the difference in their sizes is clearly visible.

Collagen in concentration of 6 mg/ml polymerized in the presence of 2 ml or 4 ml ammonia yielded the support matrix having pore sizes in the optimal range of about 233±55 µm and about 235±67 µm, respectively. At 6 ml of ammonia, the matrix formed with pore sizes in the range of 334±89 µm.

Figure 4A:
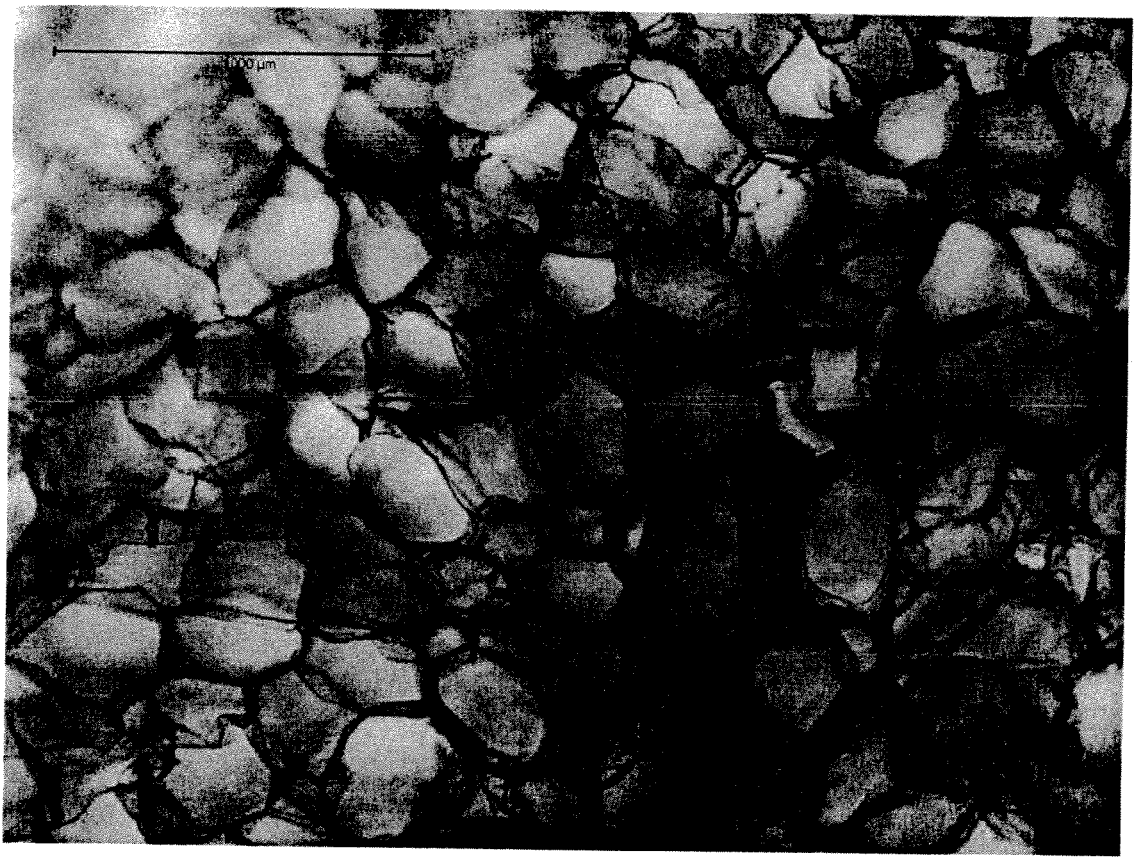
FIG. 4A is a microphotograph of a Type I collagen-based matrix prepared from 6 mg/ml of collagen in the presence of 2 ml of 3% ammonia, showing the pore size 233±55 μm, where the pore size and distribution of pores through the matrix is substantially the same. When under the same conditions, the ammonia volume was increased to 4 ml, the pore size increased only slightly to 235±67 μm, as seen in FIG. 4B. Scale (1000 μm, i.e. 1 cm) is shown in upper left corner.
Figure 4B:
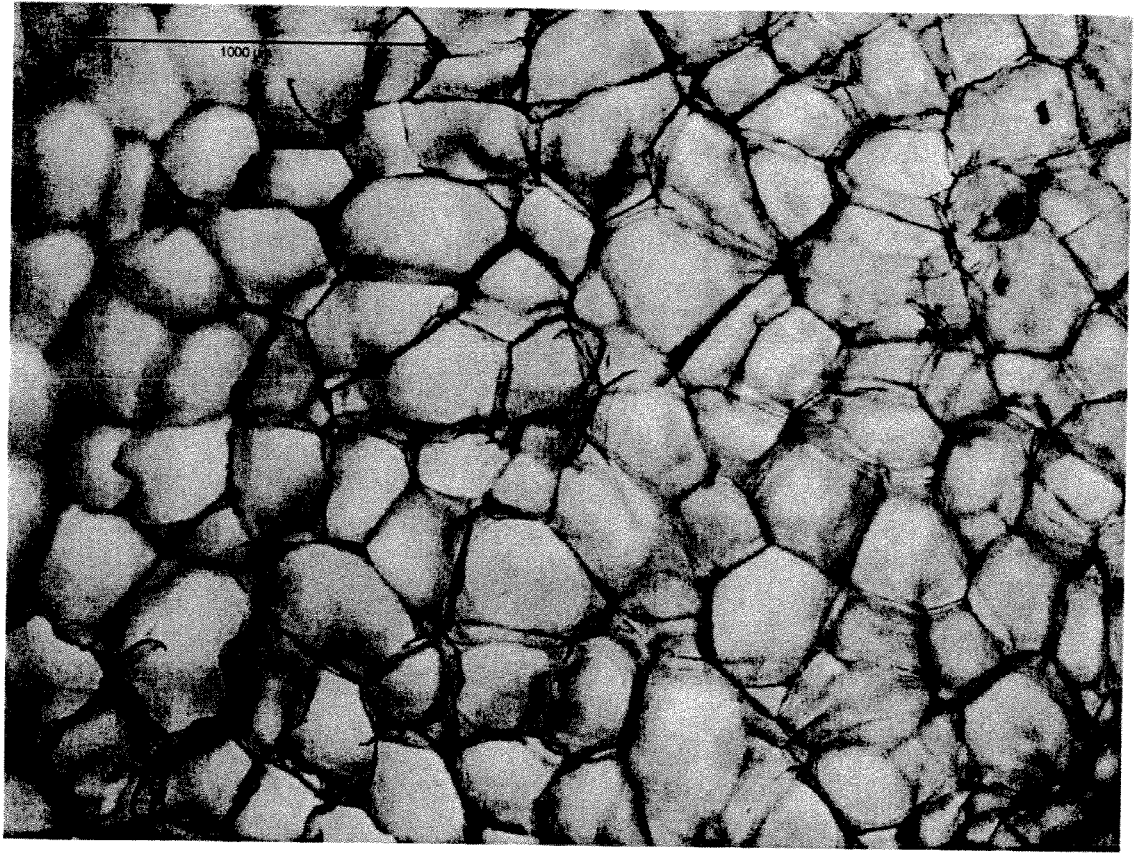

FIG. 4A and FIG. 4B are representative microphotographs of support matrices prepared from 6 mg/ml collagen and 2 or 4 ml of ammonia resulting in pore sizes ranges of about 233±55 µm and about 235±67 µm. Both microphotographs are on the same scale (scale 1000 µm). Both microphotograps show the pores to be of approximately the same size. Homogeneity of their distribution is clearly visible.

Polymerization of collagen at 8 mg/ml collagen and at 2, 3, and 4 ml of ammonia resulted in the support matrix having larger pores in ranges 284±90 µm, 299±73 µm and 1195±294 µm, respectively. At 10 mg/ml polymerization yielded a matrix with pores in the range of 474±108 µm exemplifying inherent variability occurring with higher concentrations of collagen.

As seen from these results, the support matrix prepared with a moderate amount of collagen between 4 and preferably 6 mg/ml, in the presence of moderate volume of ammonia, between 2 and 4 ml resulted in the matrix having the pore sizes within the optimal range of about 200±100 µm.

b. Effect of the Inert Atmosphere and Reduced Pressure

In another embodiment, the support matrix was prepared from bovine Type I atelocollagen, as already described above and the support matrix was prepared in the inert nitrogen atmosphere and at reduced pressure. The procedure conditions for preparation of the support matrix in the presence of ammonia and at inert atmosphere and reduced pressure is described in Example 5.

The support matrix obtained under these conditions and the pore sizes expressed as a function of collagen concentration and volume of ammonia solution/concentration are seen in Table 2.

TABLE 2

| Volume 3%/NH3 | Final pressure | Pore size (µm) |
|---|---|---|
| 1 ml | 10 torr | 323 ± 82* |
| 1 ml | 3 torr | 253 ± 59* |
| 3 ml | 10 torr | 538 ± 135 |
| 6 ml | 3 torr | 557 ± 148 |

Table 2 shows the pore size as a function of volume of ammonia solution/concentration and reduced pressure. Pore size is measured within 1 mm of the surface of the formed scaffold.

As seen at Table 2, at a collagen concentration of 5 mg/ml in all instances, and with presence of 1, 2 or 3 ml ammonia, the smallest pores were obtained in an inert atmosphere combined with reduced pressure at three torr. In that instance, the pore sizes were in the range from 253±59 µm. All other combinations resulted in larger pore sizes above 300 µm.

Figure 5A:
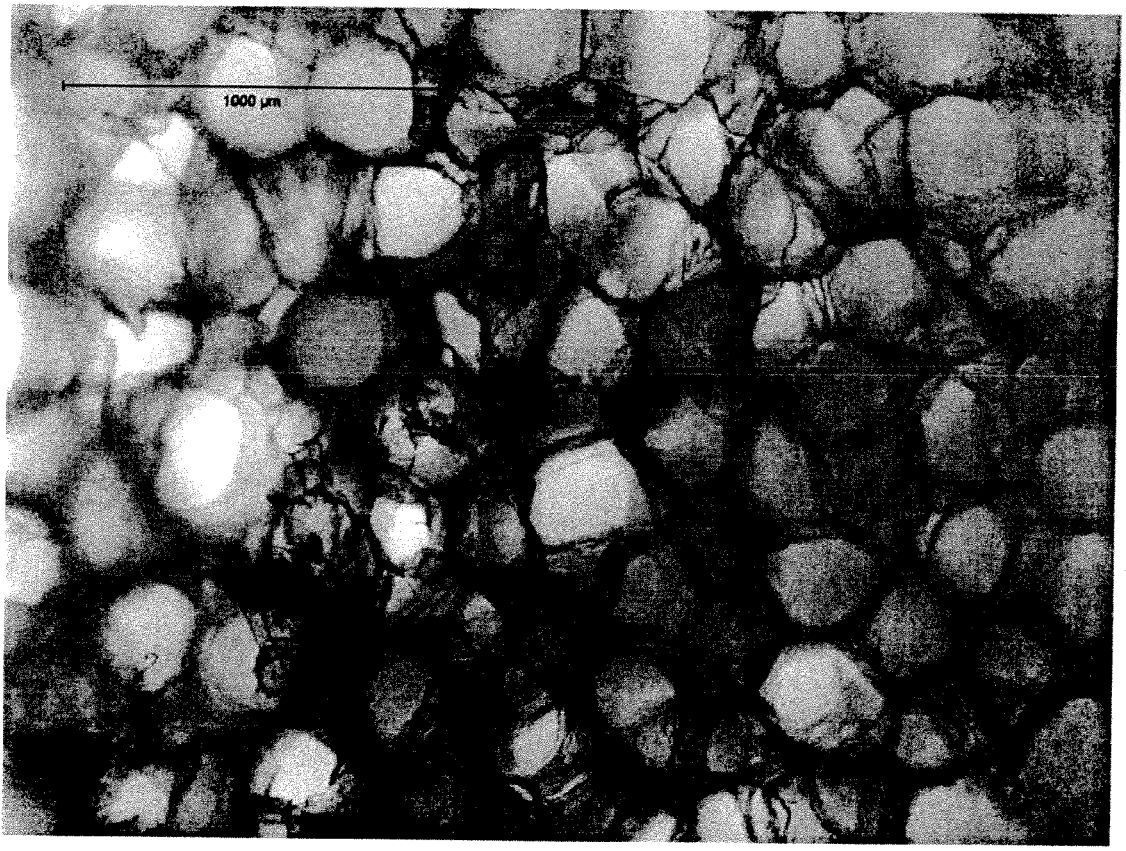
FIG. 5A is a microphotograph of a Type I collagen-based matrix prepared from 5 mg/ml of collagen in the presence of 1 ml of 3% ammonia prepared in an inert (nitrogen) atmosphere under reduced pressure (3 torr), showing the pore size 253±59 μm, wherein the pore size and distribution of pores through the matrix are substantially the same. When under the same conditions, the nitrogen atmosphere pressure was further decreased to 10 torr, the pore size increased to 323±82 μm, as seen in FIG. 5B. When under the same conditions the ammonia volume was increased to 3 ml, the size of pores increased to 538±135 μm, as seen in FIG. 5C. Scale (1000 μm, i.e. 1 cm) is shown in upper left corner.

FIG. 5A shows the pore size of 253±59 µm of the matrix made of the polymerization of 5 mg/ml collagen with 1 ml of ammonia in nitrogen atmosphere at reduced pressure to three torr.

Figure 5B:
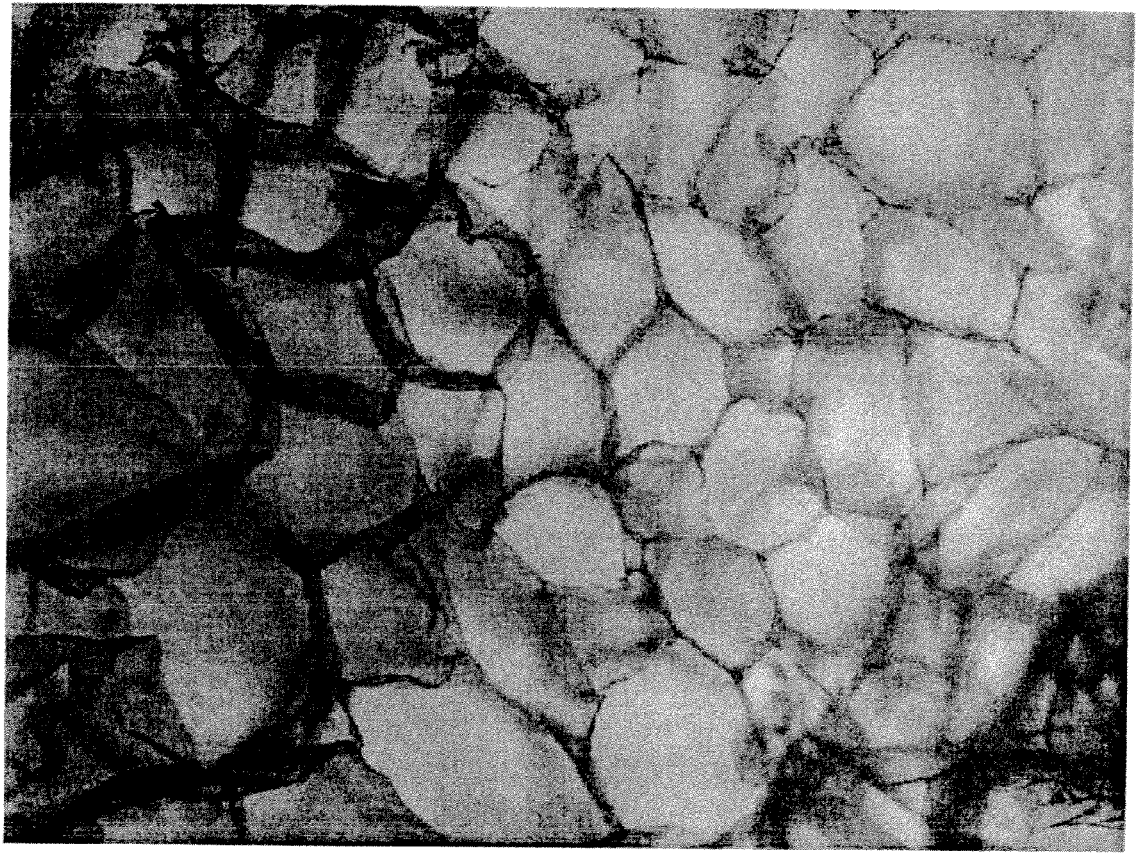

FIG. 5B shows the matrix having a pore size of 323±82 µm made of the polymerization of 5 mg/ml collagen with 1 ml of ammonia in nitrogen atmosphere at reduced pressure to 10 torr.

Figure 5C:
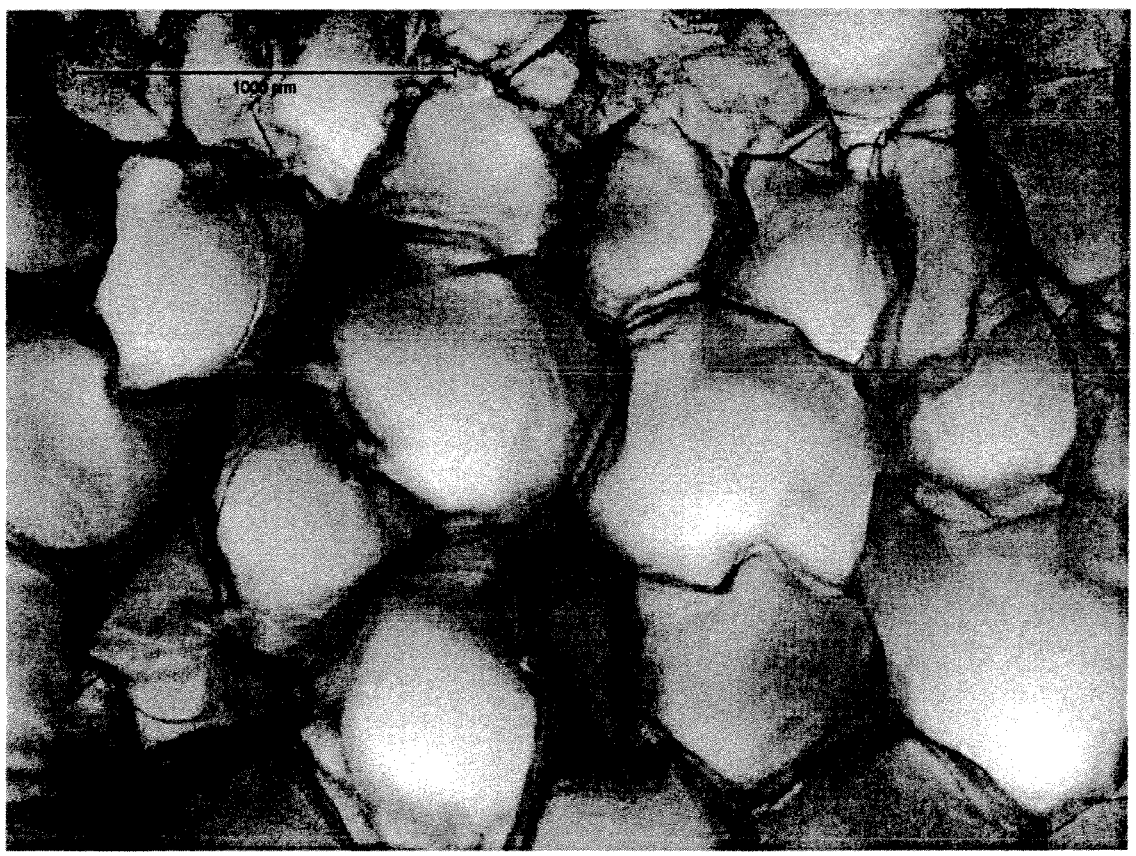

FIG. 5C shows the pore size of 538±135 µm of the matrix made by polymerization of 5 mg/ml collagen with 3 ml of ammonia in nitrogen atmosphere at reduced pressure to 10 torr.

As seen from these results, the support matrix prepared with a small volume of ammonia combined with a moderate reduction of pressure performed in an inert atmosphere resulted in the matrix having the pore sizes within the optimal range of about 200±100 µm.

c. Effect of a Surfactant on Pore Sizes

In another embodiment, the support matrix was prepared from bovine Type I atelocollagen, as described above. The procedure for preparation of the support matrix in the presence of surfactant is described in Example 4.

The support matrix obtained under these conditions and the pore size is expressed as a function of collagen concentration in the presence of the 0.3% by weight of Pluronic® surfactant is seen in Table 3.

TABLE 3

| Collagen Conc. | Pores size (µm) |
|---|---|
| 4 mg/ml | 198 ± 47* |
| 6 mg/ml | 256 ± 59* |
| 8 mg/ml | 380 ± 100* |

Pore size seen in Table 3 is expressed as a function of collagen concentration. Pore size is measured within 1 mm of the surface of the formed matrix.

As seen in Table 3, at a concentration of collagen at 4 mg/ml and in the presence of the surfactant, the pore size of the support matrix was about 198±47 µm. At 6 mg/ml and at 8 mg/ml of collagen, the support matrix had pore sizes in the range from about 256±59 µm and about 380±100 µm.

Figure 6A:
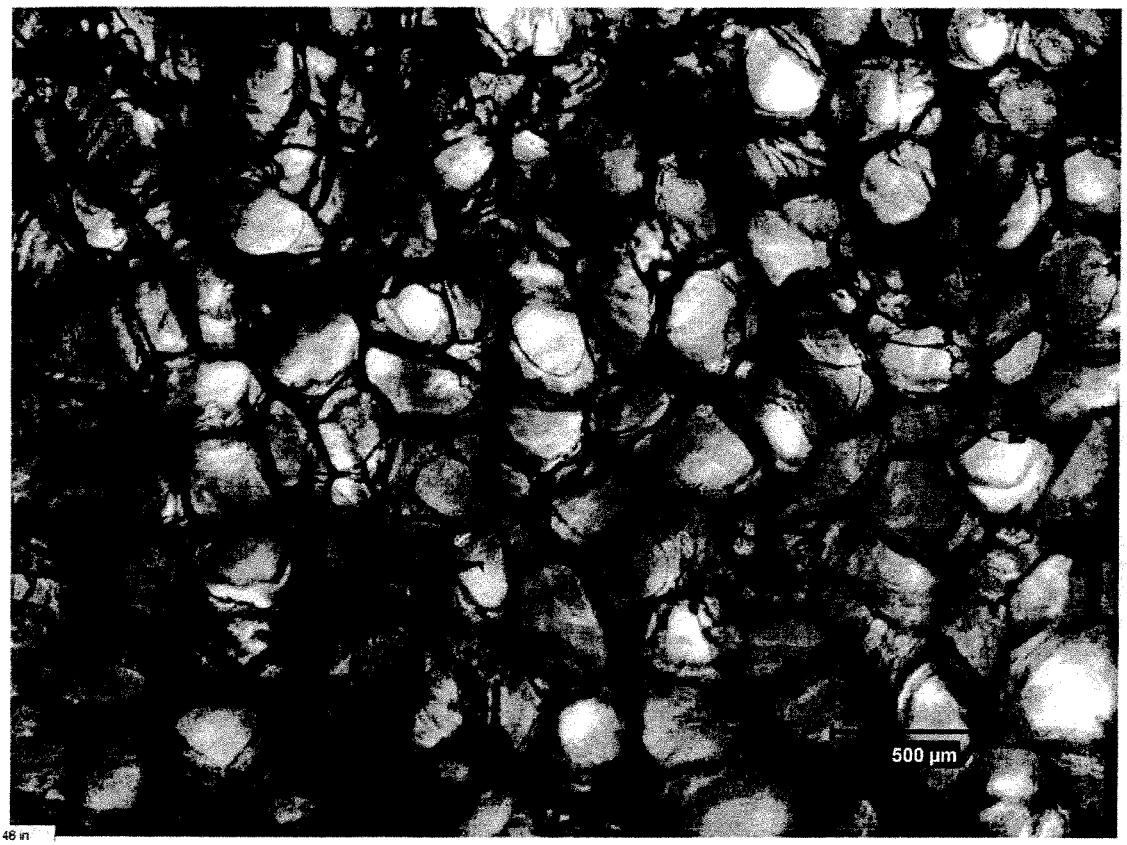
FIG. 6A is a microphotograph of a Type I collagen-based matrix prepared from 4 mg/ml of collagen in the presence of 5 ml of 3% ammonia prepared in the presence of non-ionic surfactant (Pluronic® F68; 0.3% weight/%). The pore size at the surface of the matrix was 198±47 μm, showing the pore size and distribution of pores through the matrix to be homogeneous and the pore sizes substantially the same. When under the same conditions, the amount of collagen was increased to 6 mg/ml, the pore size increased to 256±59 μm, as seen in FIG. 6B. When under the same conditions the collagen was increased to 8 mg/ml, the size of pores rose to 380±100 μm, as seen in FIG. 6C. Scale is 500 μm shown in lower right corner.
Figure 6B:
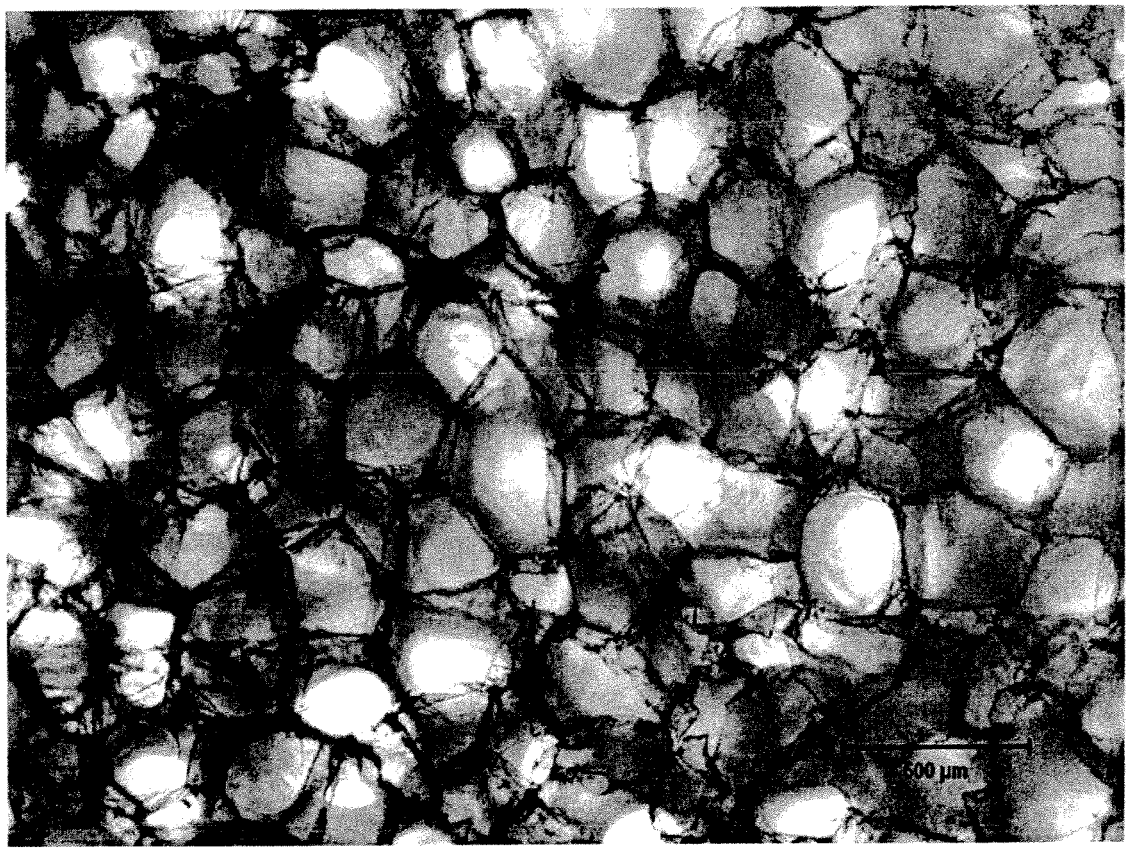
Figure 6C:
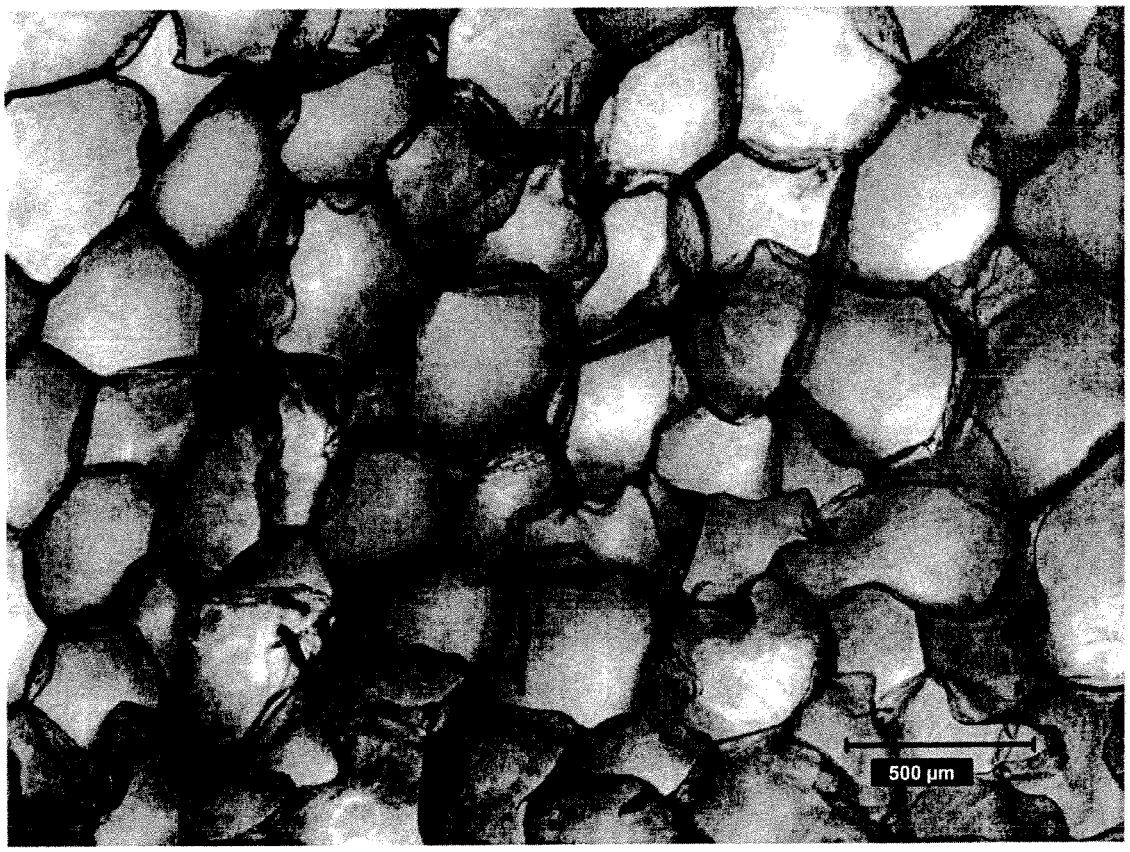

FIGS. 6A, 6B and 6C, having the same scale, are the microphotographs of matrices resulting from polymerization of 4, 6 and 8 mg/ml of collagen in the presence of the surfactant. These figures again clearly show the uniformity and homogeneity of the resulting pores as well as their uniform sizes.

Presence of the surfactant in the collagen pre-polymerization mixture clearly affects the formation of pore sizes within the optimal ranges, particularly when combined with lower concentration of collagen, polymerization of collagen (4 mg/ml) resulted in matrix having optimally sized pores of about 198±47 µm.

d. Other Factors

Some other factors may also positively affect the pore sizes similarly to the above described ones.

For example, the collagen precursors may be used to reconstitute collagen fibrillar structure for matrix protection. These precursors are, for example peptide monomers, such as alpha 1 (type I), and alpha 2 (type I) collagen peptides or in combination of 2 (alpha 1, type I) and 1 (alpha 2, type I) peptides, or 3 (alpha I, type II) peptides.

The other factors that may be manipulated are the selective vortical shearing of the peptide monomer, the chemical composition and pH of the solubilization buffer.

The vortical shearing step determines the dispersion and alignment of the associated collagen fibrils of alpha I (type I) and alpha II (type I) peptides. During this procedure equilibration in a nitrogen or argon atmosphere controls pH.

Other factors that may be used are the neutralization reactants for polymerization, temperature, rate and percentage of water removal.

Exemplary conditions for preparation of the collagen-based matrix are as follows.

The concentration of Type I collagen for fabrication of the collagen-based matrix is about from about 2 to about 10, preferably from about 4 to about 8, most preferably about 4 to about 6 mg/ml. Such concentration of collagen is critical for the initial polymerization resulting in fibrillogenesis, that is for formation of fibrils. Prior and current studies show that at the concentration of collagen below 3 mg/ml there is no fibrillogenesis, and thus no pore formation, unless such is promoted by addition of some other components.

The suitable buffers for solubilization of the Type I collagen are, for example, a formic acid containing buffer at pH 4.8, acetic acid containing buffer at pH 5.0 or a diluted hydrochloric acid at pH 3.0.

The shearing of the collagen solution is set, for example, to be for about 10-60 seconds at 10-100 dynes/cm$^2$.

The sheared peptides are equilibrated in an inert gas atmosphere such as nitrogen or argon gas for about 30 minutes to about 2 hours at about 4° C. The use of the inert gas displaces air containing oxygen that may act as an oxidant and decrease fibrillogenesis. This factor was found to positively affect the polymerization and pore formation.

Neutralization is typically carried out in a vapor of about 0.3% ammonia over about 12 to about 24 hour period. This factor has also been found to affect the collagen polymerization and formation of pores having homogeneous pore size.

Freezing, if there is, is carried out at −40° C. to about −60° C. over a period of about 2 to about 12 hours.

Water removal is achieved by exposure to an anhydrous atmosphere from −20° C. to about 50° C. preferably at 37° C. for about 24 to about 48 hours.

The gradual nature of the polymerization and slow process of water removal typically maintains the architectural elements of the scaffold collagen-based to achieve the proper orientation and diameter of the longitudinal pore structure necessary for hyaline cartilage extracellular matrix deposition by the cells.

The organization of the newly synthesized cartilage specific matrix within the porous type I collagen is visualized and quantified by, for example, ELISA/Western blot methods for determination of protein levels or quantitative RT-PCR or real-time PCR for m-RNA level.

III. Sterically-Enhanced Induction of Hyaline Cartilage

A main aspect of the current invention is a finding that when the pore sizes are substantially homogeneously restricted to a narrowly defined diameter, preferably to a pore size diameter of about 200±100, preferably 200±50 μm, and when such pores are vertically organized, such diameter of said pores in conjunction with the chondrocyte suspension facilitates a sterically-enhanced enablement of hyaline cartilage leading to formation of extracellular matrix. Such sterically-enhanced enablement leads to a deposition of collagen Type II and proteoglycans within the matrix in ratios characteristic of articular cartilage.

IV. Gel-Matrix Composite System Capable of Inducing Cartilage Production

In one embodiment, the invention concerns a collagen-based matrix prepared from Type I collagen seeded with chondrocytes suspended in synthetic sol-gel, which gels at body temperature.

The gel-matrix composite system comprises a matrix having pore diameters of about 200±100 μm, preferably 200±50 μm, that permit uniform infusion of chondrocyte/gel suspensions into the pores, and induces deposition of collagen Type II and proteoglycans (glycosaminoglycans) within the matrix in ratios characteristic of articular cartilage.

The collagen-based matrix of the current invention acts like a porous sponge when infiltrated with the suspended chondrocytes by, for example, wicking or infusion, wherein the cells are distributed within the matrix pores.

This arrangement permits chondrocytes to migrate and settle in the support matrix in a sterically-enhanced fashion and enables them to proliferate and secrete materials for generation of new extracellular matrix and eventually producing a hyaline cartilage.

Suspending solution for chondrocytes is any gel solution, preferably one containing collagen, gel, sol-gel or theromorversible hydrogel that can change its state from sol to gel depending on the temperature, and is preferably a thermoreversible gelation hydrogel (TRGH) material in which the sol-gel transition occurs on the opposite temperature cycle of agar and gelatin gels. Consequently, the viscous fluidic phase is in a sol stage and the solid phase is in a gel stage. TRGH has very quick sol-gel transformation which requires no cure time and occurs simply as a function of temperature without hysteresis. The sol-gel transition temperature for embedding chondrocytes within the collagen-based matrix is set at a temperature where the sol-gel is in a sol state whereas the temperature for stabilizing the chondrocytes within the matrix is set at a body temperature in the range of about 37° C.

V. Comparative Experimental Studies

Comparative experimental studies were performed in order to biochemically evaluate a porous matrix seeded with a chondrocyte suspension in collagen and to further evaluate the effect of pore size of the porous support matrix on the chondrocytes proliferation and extracellular matrix formation.

These studies were performed using human chondrocytes. Healthy human articular cartilage (hAC) tissue was obtained from the Tissue Bank, The National Disease Research Interchange, Philadelphia, Pa. The cartilage tissue was digested, isolated chondrocytes were seeded on culture dishes and precultured for monolayer cell expansion. Isolated chondrocytes were seeded in a 3D culture, according to a procedure described in Examples 7 and 8.

A. Cell Seeding and Time-Dependent Production of Proteoglycan

For this study, the production of total sulfated glycosaminoglycan (S-GAG) content was measured by DMB assay after 0 and 21 days of culture.

The experimental set-up is described in Example 6. Briefly, the cells were seeded into the support matrix and cultured over night and their S-GAG content and DNA (showing a number of cells) was determined at days zero and 21.

Results are summarized in Table 4 and FIGS. 7A and 7B.

TABLE 4

Results of Biochemical Evaluation

| Biochemical | Day 0 | | Day 21 | |
| --- | --- | --- | --- | --- |
| Results | Mean | SD | Mean | SD |
| S-GAG accumulation | 28.53 | ±4.35 | 117.42* | ±16.55 |
| DNA contents | 1.69 | ±0.66 | 1.98 | ±0.30 |

*$P < 0.05$

At day 0, the average of S-GAG content was 28.53±4.35 μg. At day 21, the amount of S-GAG was 117.42±16.55 μg (Table 4 and FIG. 7A). The S-GAG accumulation in the matrix at day 21 was significantly increased as compared to that at day 0. Results are seen in Table 4 and in FIG. 7A.

At day 21, the S-GAG accumulation was 4.2 fold greater than that at day 0 ($P < 0.01$). No statistical difference of the DNA content between day 0 and 21 was observed, however tendency of increasing DNA content was observed at day 21 as compared to day 0.

FIG. 7A shows results of the DMB assay where the S-GAG content was determined on day zero and day 21. As seen in FIG. 7A, culturing of the composite for 21 days led to a substantially increased production of S-GAG. In contrast, the production of DNA did not increase under these conditions, as seen in FIG. 7B, where DNA in μg/composite was determined.

In the novel composite of collagen-based porous matrix comprising chondrocytes suspended in a collagen hydrogel, chondrocyte proliferation and enhanced cartilage accumulation was observed. This finding indicates that the composite of the collagen-based porous matrix and hydrogel suspension of chondrocytes is beneficial for cell adherence and proliferation and accumulation of the cartilage specific Extracellular Matrix in vitro.

B. Evaluation of the Effect of Pore Size of the Collagen-Based Support on Extracellular Matrix Production For the evaluation of the effects of the pore size on biochemical parameters, the total S-GAG content was measured by DMB assay after 21 days of culture. Experimental procedure is described in Example 8.

The average of S-GAG content in constructs with a small pore size was 183.01±39.78 μg (Table 5 and FIG. 8A). AS seen in Table 5 in FIG. 8A, the amount of S-GAG in constructs with a large pore size was 115.56±13.50 μg (Table 4 and FIG. 8A). The S-GAG accumulation in constructs with small pore size was significantly greater than that with large pore size (Table 5 and FIG. 8A).

The S-GAG accumulation in constructs with small pore size was 1.6-fold greater than that with large pore size (Table 5 and FIG. 8A) ($P<0.05$).

The DNA content in constructs with a small pore size was significantly greater than for constructs with a large pore size (Table 5 and FIG. 8A). The DNA content in constructs with a small pore size was 1.5-fold greater than that with a large pore size (Table 5 and FIG. 8A) ($P<0.05$).

TABLE 5

Results of Biochemical Evaluation

| Biochemical | Small Pore | | Large Pore | |
| --- | --- | --- | --- | --- |
| Results | Mean | SD | Mean | SD |
| S-GAG accumulation | 183.01* | ±39.78 | 115.56 | ±13.50 |
| DNA Contents | 2.78* | ±0.21 | 1.81 | ±0.10 |

*$P < 0.05$

Results of this study are illustrated in FIGS. 8A and 8B. FIG. 8A shows results obtained in DMB assay where the S-GAG content per/composite is shown for a composite having large or small pores. As seen in FIG. 8A, small pores composites produced approximately one half more of S-GAG than the composite having large pores. Similar results were seen in FIG. 8B illustrating a DNA content in composite having a large or small pores. As observed for S-GAG. The DNA content in the composite having smaller pores was significantly higher then in the composite having a large pores.

As clearly seen in FIG. 8A, the production of S-GAG provides evidence that the cartilage ECM formation was significantly higher in composites having the small pores when compared to composites having the large pores. FIG. 8B is a graph showing a content of DNA, measured by DNA assay, in composites having small pores (153±39 μm) or large pores (435±60 μm). As clearly seen in FIG. 8B, the production of DNA was significantly higher in the composites having smaller pores as compared to that with larger pores.

Small pore size of the composite porous matrix shows significant cell proliferation and cartilage specific accumulation in the matrix as compared to that of large pore size.

C. Viability Determination

To establish biocompatibility of the support matrix of the invention, viability studies were performed. Experimental procedure is described in Example 9.

The matrices prepared with different collagen concentrations in the presence of surfactant readily absorbed the chondrocyte-laden gel. As seen in Table 6 below, the cell counts were consistent with the pore size distribution present in FIG. 6, with a cell viability of 98-99%.

TABLE 6

| Group | Mean cell count ±SD | Mean % Viability | Comments |
| --- | --- | --- | --- |
| Table 6: 4 mg/ml collagen with Pluronic | 100,800 ± 41,692 | 98.7 | |
| Table 6: 6 mg/ml collagen with Pluronic | 103,500 ± 15,679 | 99% | |
| Table 6: 8 mg/ml collagen with Pluronic | 88,350 ± 2,758 | 99.0 | |

VI. Method for Use of Gel-Matrix Composite System

The matrix and a system of the invention are useful for production of hyaline cartilage in situ or in vitro. In both cases, the collagen-based matrix is prepared as a matrix wafer. For in situ use that is achieved by way of an implant, the matrix wafer is cut into a size of the cartilage defect and introduced into the cartilage defect or lesion or the cartilage with some bone loss such as osteochondral defects.

The chondrocytes suspension is then introduced as a sol under colder than body temperature into said matrix emplaced in the lesion or defect thereby generating a gel-matrix composite system in situ and the temperature is raised to the body temperature whereby the sol is transitionally changed into a gel.

In alternative, the invention works in the same way for acellular implant where the collagen-based matrix filled with the sol-gel is introduced without chondrocytes. The implant is left in the body until the new hyaline cartilage is generated and the matrix which is biodegradable self-degrades.

For in vitro use, the process is similar but proceeds in the tube or Petri dish under the same conditions until the hyaline cartilage is produced. Such cartilage may then be used as an implant into the cartilage defect or lesion.

Example 1

Preparation of the Collagen-Based Matrix

This example describes one exemplary method for preparation of the collagen-based matrix.

Type I collagen is dissolved in a formic acid buffer at pH 4.8 and its concentration is adjusted to about 5.2 mg/ml. The solution is subjected to a vortical shearing for 10 seconds at 10 dynes per cm. The sheared peptides is then equilibrated in nitrogen gas for 30 minutes at 4° C. to displace air. Neutralization is carried out in a vapor of 0.3% ammonia over a 24 hour period. The solution is then subjected to freezing at −40° C. over a period of 2 hours. Water is removed by exposing the frozen solution to an anhydrous atmosphere at 37° C. for 24 hours.

The organization of the newly synthesized cartilage specific matrix within the porous type I collagen is visualized and quantified using immunohistochemical methods and matrix-specific gene expression quantified by in situ mRNA hybridization.

Example 2

Preparation of Collagen-Based Matrix

This example illustrates another exemplary method for preparation of the collagen-based matrix.

300 grams of a 1% aqueous atelocollagen solution (VITROGEN®), maintained at pH 3.0, is poured into a 10×20 cm tray. This tray is then placed in a 5 liter container. A 50 mL open container containing 30 mL of a 3% aqueous ammonia solution is then placed next to the tray, in the 5 liter chamber, containing 300 grams of said 1% aqueous solution of atelocollagen. The 5 liter container containing the open trays of atelocollagen and ammonia is then sealed and left to stand at room temperature for 12 hours. During this period the ammonia gas, released from the open container of aqueous ammonia and confined within the sealed 5 liter container, is reacted with the aqueous atelocollagen resulting in gelling said aqueous solution of atelocollagen.

The collagenous gel is then washed with water overnight and, subsequently, freeze-dried to yield a sponge like matrix. This freeze dried matrix is then cut into squares, sterilized, and stored under a sterile wrap.

Example 3

Effect of Ammonia on Preparation of Porous Honeycomb Scaffold

This example illustrates a general procedure utilizing ammonia for preparation of porous honeycomb scaffold having substantially the same size and distribution of pores.

About 30 g collagen solution (concentrations listed in table 1) with a pH of 3.0-4.8 was added to a 100 ml glass beaker. The solution was centrifuged for 5-10 minutes at 800×g to remove air bubbles. After centrifugation the beaker with collagen solution was sealed in a 7.1 dm$^3$ container together with 3% aqueous ammonia. The collagen solution was precipitated in the presence of ammonia gas for 3-14 h, forming vertical cone shaped pores where the diameter increased with the depth. After precipitation the collagen gel was washed with deionized water for 1-3 days in order to remove excess ammonia and formed salts. The washed collagen was then slowly frozen and lyophilized.

Example 4

Effect of Surfactant on Pore Size

This example illustrates preparation of porous honeycomb scaffold in the presence of a surfactant.

20 g of collagen solution with 0.3 weight % of Pluronic® F68 (BASF), a non ionic surfactant with a pH of 3.5-3.8, was added to a 100 ml glass beaker. The collagen concentration versus the final pore size is listed in the table below. The solution was centrifuged for 5-10 minutes at 800×g to remove air bubbles. After centrifugation the beaker with collagen solution was sealed in a 7.1 dm$^3$ container together with 3% aqueous ammonia. The collagen solution was precipitated in the presence of ammonia gas for 2 h, forming vertical cone shaped pores where the diameter increased with the depth. After precipitation the collagen gel was washed with deionized water for 1 day in order to remove excess ammonia and formed salts. The washed collagen was then slowly frozen and lyophilized.

Example 5

Effect of Inert Atmosphere and Reduced Pressure on Pore Size

This example illustrates preparation of honeycomb porous scaffold in inert atmosphere ($N_2$) and under reduced pressure. 15 g of bovine type 1 atelocollagen dissolved in aqueous HCl with a concentration of 5 mg/ml and pH of 3.3 was added to a 100 ml glass beaker. The solution was centrifuged for 5-10 minutes at 800×g to remove air bubbles. After centrifugation the collagen solution was placed in 9.1 dm$^3$ container. The container was sealed and the air evacuated using a vacuum pump to a pressure of about 2 torr (water almost boiled). The pump was turned off and the system was filled with nitrogen to about torr. Evacuation and filling was repeated three times. Before the addition of ammonia the pressure was again reduced to about 2 torr and the vacuum pump and flask were closed off. Aqueous ammonia was charged to the flask and after 30 seconds the connection to the container was opened and nitrogen was used to flush the ammonia gas into the container with the collagen solution. The final pressure in the container was in the range of 3-15 torr. The precipitation and formation of pores was complete in 40 minutes.

The formed pores were vertical and cone shaped and the diameter increased with increasing distance from the surface of the collagen gel. The precipitated collagen was washed with deionized water for 1 day in order to remove excess ammonia and formed salts. The washed collagen was then slowly frozen and lyophilized.

Example 6

Evaluation of Time-Dependent Production of Proteoglycan

This example describes a study performed for evaluation of the importance of the pore size for induction of production of a hyaline articulate cartilage.

To evaluate the effect of the pore size of through porous matrix, 2 different pore sized matrices were prepared. Large pore matrix had pores of an average size of 435 μm. Small pore matrix had pores of an average size of 153 μm.

Cells were harvested with trypsin-EDTA (Invitrogen). Three hundred thousand chondrocytes obtained from human articulate cartilage (hACs) were suspended in hydrogel (collagen gel) and seeded into a composite of a porous sponge matrix having an average pore size 435 μm or an average pore size 153 μm. The composites were then transferred into the culture medium. After 12 hours pre-incubation, cell constructs were cultured in medium comprising 5% $CO_2$, 2% $O_2$ and 37° C. in a multigas incubator using DMEM/F-12 medium with 10% FBS, 1% ITS, 0.1% gentamycin (Invitrogen). After 21 days of culture, constructs were harvested for biochemical evaluation.

Example 7

Biochemical Evaluations

This example describes methods used for biochemical evaluation of collagen-based composites.

For biochemical analysis, composites were digested in papain at 60° C. for 18 hours. DNA was measured using the Hoechst 33258 dye method described in *Anal. Biochem.*, 174:168-176 (1988). Sulfated-glycosaminoglycan (S-GAG) content was measured using a modified dimethylmethylene blue (DMB) microassay described in *Connect. Tissue Res.*, 9:247-248 (1982).

Example 8

Cell Seeding in a Three-Dimensional Collagen-Based Matrix

This example describes the procedure used for cell harvesting and seeding in the collagen-based matrix according to the invention.

Cells were harvested with trypsin-EDTA (Invitrogen). Three hundred thousand human articular chondrocytes (hACs) were suspended in a collagen hydrogel and seeded into the composite of porous collagen-based matrix having a predetermined average pore size 435 μm or 153 μm. The cell constructs were incubated at 37° C. for about one hour collagen gelation and then transferred into the culture medium. After 12 hours pre-incubation, the composites comprising chondrocytes were cultivated. After zero and 21 days of culture, constructs were harvested for biochemical evaluation.

Example 9

Viability Determination

This example illustrates determination of cell viability.

Collagen-based matrices prepared by the surfactant method were seeded with approximately 200,000 chondrocytes in a collagen gel by absorption and incubated for 3 days. An n=3 was used for each group. At termination, the chondrocyte-contained matrices were placed in 1.5 ml microcentrifuge tubes and incubated overnight in 0.15% collagenase. The digest was spun at 2000 rpm for 5 minutes and the supernatant aspirated. An aliquot of culture medium (0.1 ml) was added to the cell pellets and an aliquot taken for counting. Cell viability and total cell count was measured using trypan blue.

The invention claimed is:

1. An implant comprising:
   a collagen scaffold comprising pores, having a basal surface and an apical surface each with openings to the pores, wherein at least 85% of the pores in the scaffold are vertically oriented; and
   a suspension of chondrocytes seeded into the scaffold.

2. The implant of claim 1, wherein at least 85% of the openings of the apical surface have a diameter of 200±100 micrometers.

3. The implant of claim 2, wherein the apical surface has a pore density of 25±10 pores per $mm^2$.

4. The implant of claim 1, wherein at least 85% of the openings of the basal surface have a diameter of 200±100 micrometers.

5. The implant of claim 4, wherein the basal surface has a pore density of 25±10 pores per $mm^2$.

6. The implant of claim 1, wherein at least 95% of the basal and apical openings have diameters of 200±100 micrometers.

7. The implant of claim 6, wherein at least 98% of said basal and apical openings have diameters of 200±100 micrometers.

8. The implant of claim 1, wherein the collagen scaffold comprises Type I collagen, Type II collagen, Type IV collagen or a combination thereof.

9. The implant of claim 1, wherein the scaffold is formed by polymerizing a collagen solution in the presence of ammonia vapor.

10. The implant of claim 9, wherein the collagen solution is polymerized at a reduced pressure.

11. The implant of claim 10, wherein the collagen solution is polymerized at between 3 Torr and 10 Torr of pressure.

12. The implant of claim 9, wherein the collagen solution comprises between 4 mg/ml and 8 mg/ml of Type I collagen in aqueous solution.

13. The implant of claim 12, wherein the aqueous solution is acidic.

14. The implant of claim 12, wherein the collagen solution comprises a non-ionic surfactant.

15. The implant of claim 14, wherein the non-ionic surfactant comprises a polyoxyethylene-polyoxypropylene block copolymer.

16. The implant of claim 9, further comprising freeze-drying the scaffold prior to seeding the scaffold with chondrocytes.

17. The implant of claim 1, wherein the chondrocytes are seeded as a suspension of chondrocytes in a collagen solution.

18. The implant of claim 17, wherein the collagen chondrocyte suspension has a concentration of 1 million to 12 million chondrocyte cells per mL of collagen solution.

19. The implant of claim 1, wherein the chondrocytes comprise human articular chondrocytes.

* * * * *